US012629415B2

(12) United States Patent
Lavelle et al.

(10) Patent No.: US 12,629,415 B2
(45) Date of Patent: May 19, 2026

(54) VACCINE ADJUVANTS

(71) Applicants: THE PROVOST, FELLOWS, FOUNDATION SCHOLARS, AND THE OTHER MEMBERS OF BOARD, OF THE COLLEGE OF THE HOLY AND UNDIVIDED TRINITY OF QUEEN ELIZABETH NEAR DUBLIN, Dublin (IE); TEAGASC, THE AGRICULTURE AND FOOD DEVELOPMENT AUTHORITY, Carlow (IE)

(72) Inventors: Edward Lavelle, Dublin (IE); Sarah Doyle, Dublin (IE); Ciaran Harte, Dublin (IE); Kiva Brennan, Dublin (IE); Kieran Meade, Meath (IE)

(73) Assignees: THE PROVOST, FELLOWS, FOUNDATION SCHOLARS, AND THE OTHER MEMBERS OF BOARD, OF THE COLLEGE OF THE HOLY AND UNDIVIDED TRINITY OF QUEEN ELIZABETH NEAR DUBLIN, Dublin (IE); TEAGASC, THE AGRICULTURE AND FOOD DEVELOPMENT AUTHORITY, Carlow (IE)

( * ) Notice: Subject to any disclaimer, the term of this patent is extended or adjusted under 35 U.S.C. 154(b) by 966 days.

(21) Appl. No.: 17/056,826

(22) PCT Filed: May 29, 2019

(86) PCT No.: PCT/EP2019/063989
§ 371 (c)(1),
(2) Date: Nov. 19, 2020

(87) PCT Pub. No.: WO2019/229137
PCT Pub. Date: Dec. 5, 2019

(65) Prior Publication Data
US 2021/0187104 A1     Jun. 24, 2021

(30) Foreign Application Priority Data
May 29, 2018    (EP) .................................... 18174947

(51) Int. Cl.
*A61K 39/39*        (2006.01)
*A61K 39/00*        (2006.01)
*A61P 37/04*        (2006.01)

(52) U.S. Cl.
CPC .............. *A61K 39/39* (2013.01); *A61P 37/04* (2018.01); *A61K 2039/55* (2013.01); *A61K 2039/552* (2013.01); *A61K 2039/55561* (2013.01); *A61K 2039/57* (2013.01)

(58) Field of Classification Search
None
See application file for complete search history.

(56) References Cited

U.S. PATENT DOCUMENTS

2006/0223742 A1* 10/2006 Salazar .................. A61K 39/12
                                                          514/19.5
2008/0193468 A1*  8/2008 Levy .................. A61K 31/4745
                                                          514/44 A

FOREIGN PATENT DOCUMENTS

DE     102011000036 A1 *  4/2012 ......... A61K 31/7088
WO        WO9944634 A1    9/1999

OTHER PUBLICATIONS

Pott, Johanna, et al. "Age-dependent TLR3 expression of the intestinal epithelium contributes to rotavirus susceptibility." PLoS pathogens 8.5 (2012): e1002670. (Year: 2012).*

Futata, Eliana Akemi, et al. "The neonatal immune system: immunomodulation of infections in early life." Expert review of anti-infective therapy 10.3 (2012): 289-298. (Year: 2012).*

Hafner, Annina M., Blaise Corthésy, and Hans P. Merkle. "Particulate formulations for the delivery of poly (I: C) as vaccine adjuvant." Advanced drug delivery reviews 65.10 (2013): 1386-1399. (Year: 2013).*

Lantier, Louis, et al. "Poly (I: C)-induced protection of neonatal mice against intestinal Cryptosporidium parvum infection requires an additional TLR5 signal provided by the gut flora." The Journal of infectious diseases 209.3 (2014): 457-467. (Year: 2014).*

Morris, Matthew C., and Naveen Surendran. "Neonatal vaccination: challenges and intervention strategies." Neonatology 109.3 (2016): 161-169. (Year: 2016).*

Matsumoto, Misako, and Tsukasa Seya. "TLR3: interferon induction by double-stranded RNA including poly (I:C)." Advanced drug delivery reviews 60.7 (2008): 805-812. (Year: 2008).*

Longhi, M. Paula, et al. "Dendritic cells require a systemic type I interferon response to mature and induce CD4+ Th1 immunity with poly IC as adjuvant." The Journal of experimental medicine 206.7 (2009): 1589-1602. (Year: 2009).*

(Continued)

*Primary Examiner* — Bethany P Barham
*Assistant Examiner* — Peter Anthopolos
(74) *Attorney, Agent, or Firm* — Greer, Burns & Crain, Ltd.

(57)                ABSTRACT

The present application relates to an adjuvant which is suitable to be used in vaccines or other immunogenic compositions. Specifically, the adjuvant promotes the induction of interleukin-1 (IL-1), type 1 interferons (IFNs), such as IFNα, and IFNβ, type 2 interferons, such as IFNγ and/or tumour necrosis factor (TNF) response, such as TNFα, and elicits or enhances an immune response, preferably in neonatal, juvenile or paediatric animal and/or human populations.

13 Claims, 31 Drawing Sheets

Specification includes a Sequence Listing.

(56)                    References Cited

OTHER PUBLICATIONS

Nguyen, Tan A., et al. "SIDT2 transports extracellular dsRNA into the cytoplasm for innate immune recognition." Immunity 47.3 (2017): 498-509. (Year: 2017).*

Wu, Jiaxi, and Zhijian J. Chen. "Innate immune sensing and signaling of cytosolic nucleic acids." Annual review of immunology 32.1 (2014): 461-488. (Year: 2014).*

Pollack, I. et al., "Immune responses and outcome after vaccination with glioma-associated antigen peptides and poly-ICLC in a pilot study for pediatric recurrent low-grade gliomas", Neuro-Oncology, Mar. 15, 2016, pp. 1157-1168, vol. 18, No. 8.

Martins K., et al., "Vaccine adjuvant uses of poly-Ic and derivatives", Expert Reviews, Mar. 1, 2015, pp. 447-459, vol. 14, No. 3.

Ma, F., et al., "Positive feedback regulation of type 1 IFN production by the IFN-inducible DNA sensor cGAS", National Institute of Health, Journal of Immunology, Feb. 15, 2015, pp. 1545-1554, vol. 194, No. 4.

Toussi, D., et al., "Immune Adjuvant Effect of Molecularly-defined Toll-Like Receptors Ligands", Vaccines, Apr. 25, 2014, pp. 323-353, vol. 2.

Brennan, K. et al., "Type 1 IFN Induction by Cytosolic Nucleic Acid Is Intact in Neonatal Mononuclear Cells, Contrasting Starkly with Neonatal Hyporesponsiveness to TLR Ligation Due to Independence from Endosome-Mediated IRF3 Activation", The Journal of Immunology, Jul. 6, 2018, pp. 1-18, vol. 201, No. 4.

Kollmann, T., et al., "Neonatal Innate TLR-Mediated Responses are Distinct from Those of Adults", The Journal of Immunology, (2009), pp. 7150-7160, vol. 183.

Basha, S., et al., "Immune Responses in Neonates", Expert Rev Clin Immunol., Sep. 2014, pp. 1171-1184, vol. 10, No. 9.

Bliss, J., et al., "Editorial: The Neonatal Immune System: A Unique Host-Microbial Interface", Frontiers in Pediatrics, Dec. 21, 2017, pp. 1-3, vol. 5.

Saso, A., et al., "Vaccine responses in newborns", Semin Immunopathol, (2017), pp. 627-642, vol. 39.

PCT Notification Concerning Transmittal of International Preliminary Report on Patentability dated Dec. 1, 2020 for PCT Application No. PCT/EP2019/063989.

De Brito, C., et al., "Immune adjuvants in early life: targeting the innate immune system to overcome impaired adaptive response", Future Medicine Ltd., Sep. 1, 2009, vol. 1, No. 5, pp. 883-895.

Brennan, K. et al., "Type 1 IFN Induction by Cytosolic Nucleic Acid Is Intact in Neonatal Mononuclear Cells, Contrasting Starkly with Neonatal Hyporesponsiveness to TLR Ligation Due to Independence from Endosome-Mediated IRF3 Activation", The Journal of Immunology, Jul. 6, 2018, pp. 1-18.

Brennan, K., et al., "Cytosolic dsRNA improves neonatal innate immune responses to adjuvants in use in pediatric vaccines", Journal of Leukocyte Biology, Jan. 6, 2022; pp. 523-537, vol. 112.

Brennan, K., et al., "Nucleic acid cytokine responses in obese children and infants of obese mothers", Cytokine, Mar. 20, 2019, pp. 152-158, vol. 119.

Kollmann, T., et al., "Neonatal innate TLR-mediated responses are distinct from those of adults", J Immunol, Dec. 1, 2009, pp. 7150-7160, vol. 183, No. 11.

Levy, O., et al., "Unique efficacy of Toll-like receptor 8 agonists in activating human neonatal antigen-presenting cells", Blood, American Society of Hematology, Apr. 25, 2006, pp. 1284-1290, vol. 108.

Adkins, B., et al., "Neonatal Adaptive Immunity Comes of Age", Nature Reviews | Immunology, Jul. 2004, pp. 553-564, vol. 4.

Levy, O., "Selective Impairment of TLR-Mediated Innate Immunity in Human Newborns: Neonatal Blood Plasma Reduces Monocyte TNF-α Induction by Bacterial Lipopeptides, Lipopolysaccharide, and Imiquimod, but Preserves the Response to R-8481", The Journal of Immunology, Oct. 1, 2004, pp. 4627-4634, vol. 173, No. 7.

* cited by examiner

D

E

A

B

SEQUENCE LISTING

```
<160> NUMBER OF SEQ ID NOS: 22

<210> SEQ ID NO 1
<211> LENGTH: 22
<212> TYPE: DNA
<213> ORGANISM: Artificial Sequence
<220> FEATURE:
<223> OTHER INFORMATION: IFN-alpha forward primer (Table 2.7)

<400> SEQUENCE: 1
acctagagag caggttcaca ga                                          22

<210> SEQ ID NO 2
<211> LENGTH: 20
<212> TYPE: DNA
<213> ORGANISM: Artificial Sequence
<220> FEATURE:
<223> OTHER INFORMATION: IFN-alpha reverse primer (Table 2.7)

<400> SEQUENCE: 2
cagctgagca gcaacaggat                                             20

<210> SEQ ID NO 3
<211> LENGTH: 20
<212> TYPE: DNA
<213> ORGANISM: Artificial Sequence
<220> FEATURE:
<223> OTHER INFORMATION: IFN-beta forward primer (Table 2.7)

<400> SEQUENCE: 3
```

-continued tccagcacat cttcggcatt                                           20

<210> SEQ ID NO 4
<211> LENGTH: 20
<212> TYPE: DNA
<213> ORGANISM: Artificial Sequence
<220> FEATURE:
<223> OTHER INFORMATION: IFN-beta reverse primer (Table 2.7)

<400> SEQUENCE: 4
aaggaggtcc tcgatgatgg                                           20

<210> SEQ ID NO 5
<211> LENGTH: 24
<212> TYPE: DNA
<213> ORGANISM: Artificial Sequence
<220> FEATURE:
<223> OTHER INFORMATION: IFI-16 forward primer (Table 2.7)

<400> SEQUENCE: 5
ggaagtcgtg gtttatggac agcg                                      24

<210> SEQ ID NO 6
<211> LENGTH: 28
<212> TYPE: DNA
<213> ORGANISM: Artificial Sequence
<220> FEATURE:
<223> OTHER INFORMATION: IFI-16 reverse primer (Table 2.7)

<400> SEQUENCE: 6
ccttggtgac cttgatgaaa ctatgaat                                  28

<210> SEQ ID NO 7
<211> LENGTH: 19
<212> TYPE: DNA
<213> ORGANISM: Artificial Sequence
<220> FEATURE:
<223> OTHER INFORMATION: PPIA forward primer (Table 2.7)

<400> SEQUENCE: 7
ccaccgtgtt cttcgacat                                            19

<210> SEQ ID NO 8
<211> LENGTH: 18
<212> TYPE: DNA
<213> ORGANISM: Artificial Sequence
<220> FEATURE:
<223> OTHER INFORMATION: PPIA reverse primer (Table 2.7)

<400> SEQUENCE: 8
tctgtgaagc aggaacct                                             18

<210> SEQ ID NO 9
<211> LENGTH: 20
<212> TYPE: DNA
<213> ORGANISM: artificial
<220> FEATURE:
<223> OTHER INFORMATION: CXCL10 forward primer (Table 1)

<400> SEQUENCE: 9
agcagaggaa cctccagtct                                           20

<210> SEQ ID NO 10
<211> LENGTH: 20
<212> TYPE: DNA
<213> ORGANISM: Artificial Sequence -continued

```
<220> FEATURE:
<223> OTHER INFORMATION: CXCL10 reverse primer (Table 1)

<400> SEQUENCE: 10
atgcaggtac agcgtacagt                                                   20

<210> SEQ ID NO 11
<211> LENGTH: 22
<212> TYPE: DNA
<213> ORGANISM: Artificial Sequence
<220> FEATURE:
<223> OTHER INFORMATION: IFN alpha forward primer (Table 1)

<400> SEQUENCE: 11
tgaaggacag acatgacttt gg                                                22

<210> SEQ ID NO 12
<211> LENGTH: 22
<212> TYPE: DNA
<213> ORGANISM: Artificial Sequence
<220> FEATURE:
<223> OTHER INFORMATION: IFN alpha reverse primer (table 1)

<400> SEQUENCE: 12
tcctttgtgc tgaagagatt ga                                                22

<210> SEQ ID NO 13
<211> LENGTH: 20
<212> TYPE: DNA
<213> ORGANISM: Artificial Sequence
<220> FEATURE:
<223> OTHER INFORMATION: Rab5 forward primer (Table 1)

<400> SEQUENCE: 13
acgggccaaa tacgggaaat                                                   20

<210> SEQ ID NO 14
<211> LENGTH: 20
<212> TYPE: DNA
<213> ORGANISM: Artificial Sequence
<220> FEATURE:
<223> OTHER INFORMATION: Rab5 reverse primer (Table 1)

<400> SEQUENCE: 14
agaaaagcag ccccaatggt                                                   20

<210> SEQ ID NO 15
<211> LENGTH: 20
<212> TYPE: DNA
<213> ORGANISM: Artificial Sequence
<220> FEATURE:
<223> OTHER INFORMATION: Rab7 forward primer (Table 1)

<400> SEQUENCE: 15
cagacaagtg gccacaaagc                                                   20

<210> SEQ ID NO 16
<211> LENGTH: 20
<212> TYPE: DNA
<213> ORGANISM: Artificial Sequence
<220> FEATURE:
<223> OTHER INFORMATION: Rab7 reverse primer (Table 1)

<400> SEQUENCE: 16
aagtgcattc cgtgcaatcg                                                   20
```

-continued

```
<210> SEQ ID NO 17
<211> LENGTH: 20
<212> TYPE: DNA
<213> ORGANISM: Artificial Sequence
<220> FEATURE:
<223> OTHER INFORMATION: Rab10 forward primer (Table 1)

<400> SEQUENCE: 17
cctcagaaag cccgagtgag                                              20

<210> SEQ ID NO 18
<211> LENGTH: 20
<212> TYPE: DNA
<213> ORGANISM: Artificial Sequence
<220> FEATURE:
<223> OTHER INFORMATION: Rab 10 reverse primer (Table 1)

<400> SEQUENCE: 18
gtcgtacgtc ttcttcgcca                                              20

<210> SEQ ID NO 19
<211> LENGTH: 20
<212> TYPE: DNA
<213> ORGANISM: Artificial Sequence
<220> FEATURE:
<223> OTHER INFORMATION: Rab11 forward primer (Table 1)

<400> SEQUENCE: 19
cttcggccct agactctaca                                              20

<210> SEQ ID NO 20
<211> LENGTH: 20
<212> TYPE: DNA
<213> ORGANISM: Artificial Sequence
<220> FEATURE:
<223> OTHER INFORMATION: Rab11 reverse primer (Table 1)

<400> SEQUENCE: 20
cactgcacct ttggcttgtt                                              20

<210> SEQ ID NO 21
<211> LENGTH: 20
<212> TYPE: DNA
<213> ORGANISM: Artificial Sequence
<220> FEATURE:
<223> OTHER INFORMATION: TNFalpha forward primer (Table 1)

<400> SEQUENCE: 21
ctgggcaggt ctactttggg                                              20

<210> SEQ ID NO 22
<211> LENGTH: 20
<212> TYPE: DNA
<213> ORGANISM: Artificial Sequence
<220> FEATURE:
<223> OTHER INFORMATION: TNFalpha reverse primer (Table 1)

<400> SEQUENCE: 22
ctggaggccc cagtttgaat                                              20
```

VACCINE ADJUVANTS

REFERENCE TO A SEQUENCE LISTING SUBMITTED VIA EFS-WEB

The content of the ASCII text file of the sequence listing named "1717999.txt" which is 4810 bites in size and was created on Nov. 18, 2020 and electronically submitted via EFS-Web during the filing of this application, is incorporated herein by reference in its entirety.

CROSS-REFERENCE TO RELATED APPLICATIONS

This application is the U.S. National phase application corresponding to PCT/EP2019/063989 which was assigned an international filing date of May 29, 2019 and associated with publication WO2019/229137A1 and which claims priority to EP18174947.4, filed May 29, 2018, the disclosures of which are expressly incorporated herein by reference.

FIELD OF THE INVENTION

The present application relates to an adjuvant which is suitable to be used in vaccines or other immunogenic compositions. Specifically, the adjuvant promotes the induction of interleukin-1 (IL-1), type 1 interferons (IFNs), such as IFNα, and IFNβ, type 2 interferons IFNγ and/or TNF response, such as TNFα, and elicits or enhances an immune response in neonatal, juvenile or paediatric animal and/or human populations.

BACKGROUND OF THE INVENTION

Defence against infection, is mediated by the early reactions of innate immunity and the later responses of adaptive immunity. As adults, we rely heavily on our adaptive immune system, which has had previous exposure to infectious agents and can therefore generate an effective challenge in a short time. It is this ability to "remember" infectious agents and mount an efficient, swift and targeted response to eradicate the pathogen that forms the basis of vaccination.

However, neonates and young infants are more vulnerable to certain infectious agents than older children and adults and are especially susceptible to infections with intracellular pathogens.

Due to the requirement of the adaptive immune system for immunological experience, the innate immune system, and its pattern recognition receptors (PRRs), represent the critical front-line defence against these pathogens. An increasing body of evidence suggests that neonatal innate immune responses are not fully developed and, furthermore, that the innate immune system does not resemble that of an adult until puberty.

Two million children die each year from infectious diseases before they reach 1 year, many of these diseases are vaccine preventable and many infants could be saved if it were possible to vaccinate at birth, or shortly thereafter, against infections that pose the greatest danger. Unfortunately, current vaccines for many of these infections do not work until a child is at least 9 months or older and can require numerous "booster" doses. As a result, a child must cross a dangerous "window of vulnerability" that opens when levels of maternal antibodies drop below a protective level and only closes when the child's immune system is mature enough to respond effectively to vaccination. Closing this "window of vulnerability" has the potential to save hundreds-of-thousands of infants worldwide. The challenge to early-life vaccination is that immune-responsiveness varies with age with evidence suggesting that responses elicited by the immune system of infants and young children are compromised, when compared with those in adults.

This problem is not limited to human populations but also prevalent in animal populations, including domestic animals and farm animals such as cattle, horses, pigs and sheep. For example, cattle in the first 6 months after birth are highly susceptible to a number of infectious diseases including para tuberculosis (Johne's disease) caused by the bacterium *Mycobacterium avium* subspecies *paratuberculosis* (MAP) and which results in a major economic burden on the agricultural sector. Combined with other enteric and respiratory bacterial and viral infections (see table later), the mortality can amount to 7% of calves per annum.

At its simplest, vaccine formulations comprise an antigen and an adjuvant. The antigen is a component unique to a particular pathogen that can be recognized by the highly variable antigen receptors of the adaptive immune system. A successful antigen will cause a T-cell mediated response and/or the activation of B-cells to produce antibodies. When the body meets that particular infection again, the memory cells that were made in response to the signature antigen in the vaccine will be activated to efficiently fight the infection. However, the immune system will not respond to a foreign antigen and mount a response in the absence of an adjuvant.

Adjuvants are essential substances that kick-start the immune response by indicating the presence of "danger". Adjuvants may exert their effects through different mechanisms, augmenting the activities of immune cells by mimicking natural infection. Some function as depots allowing antigen persistence at the site of injection and encouraging antigen uptake by antigen presenting cells. Others mimic specific sets of evolutionarily conserved molecules, so called "PAMPs" (Pathogen Associated Molecular Patterns) and "DAMPs" (Damage Associated Molecular Patterns). These are recognized by the Pattern Recognition Receptors (PRRs) of the innate immune system. An effective vaccine stimulates both arms of the immune system; innate and adaptive immunity leading to immune memory.

Five major classes of pattern recognition receptors (PRR) have been described; the membrane bound, TLRs and CLRs, and the cytoplasmic, NLRs, RLRs, and dsDNA sensors. PRRs are the principal effectors of innate immunity, involved in stimulating the adaptive immune response. Activation is triggered when PRRs recognise components that are conserved among broad groups of microorganisms, so called "PAMPs", or when damaged, injured or stressed cells send out alarm signals, so called "DAMPs". Once activated PRRs instruct and regulate both innate and adaptive immunity to ensure an effective and coordinated immune response is established. In the case of the TLRs, the RLRs and some NLRs, this occurs through the initiation of complex signalling pathways that result in the activation of mitogen activated protein kinases (MAPKs), pro-inflammatory transcription factors, such as Nuclear factor κB (NFκB) and Interferon Regulatory Factors (IRFs), and the induction of pro-inflammatory and anti-viral gene expression. Other PRRs such as the dsDNA sensor AIM2 and AIM2-like receptors (ALRs) and some RLRs and NLRs form multi-protein oligomeric platforms known as "inflammasomes". Inflammasomes consist of a PRR seed, the adapter protein ASC and pro-caspase-1, and control the maturation of two major pro-inflammatory cytokines, namely IL-1β and IL-18, by allowing for their cleavage from inactive pro-forms into mature cytokines. Both PRR-induced signal transduction cascades and inflammasome activation have been shown to be essential to mount an effective host response to various pathogens including those mentioned above to which neonates and infants are susceptible.

The production of pro-inflammatory cytokines, chemokines and Type 1 Interferons (IFN) in response to activation of PRRs increases the body's ability to eliminate infection through the priming, expansion and polarization of lymphocytes. This response is mediated by two main types of lymphocytes, B- and T-cells. T-cells can be stratified according to the cytokines they produce. Th17 cells help defend against extracellular pathogens, T follicular helper cells support antibody responses and Th2 cells are required for defence against certain parasites. A Th1 response also supports B-cell responses, including the production of opsonizing antibodies, but importantly a Th1 response leads mainly to cell-mediated immunity, which is vital in the fight against intracellular pathogens, such as invasive bacteria and viruses. These are the infections to which neonates and children are highly susceptible. Adjuvants currently in clinical use enhance humoral responses but new adjuvants that stimulate intracellular PRR-responses would effectively mimic a natural infection, biasing the immune response towards a Th1 cell mediated response. The most effective vaccines against intracellular infection generate Th1-polarising signals. For this reason a number of TLR agonists are at various stages of development for use in vaccines. Of note a TLR4 derivative MPLA (monophosphoryl lipid A), which formulated with alum triggers a Th1 response and is approved for use in Europe, and much effort is being expended on similarly combining alum with TLR9 agonists.

The technique of targeting dendritic cells, which are highly specialized antigen presenting cells, with an antigen has been the basis of research for more than a decade in the context of immunotherapy and vaccination e.g. Cohn L, Delamarre L. 'Dendritic cell-targeted vaccines' Front Immunol. 2014 May 30; 5:255; Barbuto et al, 'Induction of innate and adaptive immunity by delivery of poly dA:dT to dendritic cells', Nature Chemical Biology volume 9, pages 250-256 (2013), studied the delivery of antigens in the context of human monocyte derived dendritic cells and mouse dendritic cells in combination with a monoclonal antibody.

However, despite these advances and the fact that the majority of the human global vaccine market is paediatric; the current adjuvants and those in the pipeline have been designed in adult cells. As adjuvants are essential for enabling the response to vaccine antigens and pattern recognition receptor (PRR)-mediated responses to adjuvants vary with age, it follows that not all adjuvants will elicit the same responses in children as they do in adults. In fact, the lack of an efficient response to a vaccine adjuvant results in a 'window of vulnerability' to certain vaccine-preventable infections, which all infants must traverse. In most cases infants are left vulnerable to infection until they are 1 year old due to the late age at which the first immunization can be administered and the requirement for up to three booster vaccinations before full protection is assumed. In some cases, further boosters are required into early adolescence. Thus, there is a need to improve vaccine efficacy, reduce the need for later boosters which would improve both compliance with childhood immunisation programmes and protective immunisation in human populations. This would also be of significant benefit in the agriculture sector.

Approximately 2.5 million calves are born in the beef and dairy herds nationally in Ireland per year. All these calves require multiple vaccinations for protection during the early neonatal window of disease susceptibility. However, despite the widespread availability of vaccinations, sub-optimal formulations contribute to poor efficacy and almost 7% of these calves succumb to disease representing a major cost to the industry and a threat to sustainability Even where disease outbreaks in adult cattle, eradication schemes can be costly and are prohibitive to implement unless strict criteria of sensitivity and specificity are met for vaccine formulations. Cross-reactivity could lead to false-positives in other diagnostic tests (e.g. TB) and have implications for economic trade. In order to ensure specificity, next-generation vaccines are being designed based on pathogen sub-units which although safe, provide less immunological protection. As a result, the use of adjuvants to enhance and direct adaptive immune responses has become the focus of much targeted bovine vaccine research. Ideal new effective adjuvants will be targeted in their mechanisms of action to drive tailored protective immune responses, and are immunostimulatory enough to reduce the requirement for repeat administrations. Adjuvant delivery mechanisms are also required to overcome sequesterisation of the antigen by maternal antibodies.

Thus, the present invention aims to address the need for new and improved vaccines against existing and emerging infections, specifically in neonatal and/or paediatric human and/or animal populations.

SUMMARY OF THE INVENTION

In a general context, the present invention provides an adjuvant which targets intracellular nucleic acid sensors, so called cytosolic nucleic acid (CNA) sensors, for use in eliciting or enhancing a type 1 interferon response in a neonatal, juvenile or paediatric animal subject. One main objective is to stimulate the innate immune system in the neonatal, juvenile or paediatric animal subject by targeting these CNA sensors and stimulate the pattern recognition receptors (PRR) response via intracellular PRRs. For example, by targeting intracellular CNA sensors a type1 IFN response or Th1 response can be elicited to stimulate the innate immune response.

Accordingly, a first embodiment of the application provides an adjuvant as defined in claim 1 which promotes the induction of cytokines such as interleukin-1 (IL-1), type 1 interferons (IFNs), such as IFNα, and IFNβ, and type 2 interferons, such as IFNγ, and/or tumour necrosis factor (TNF) response, such as TNFα, for use in eliciting or enhancing an immune response in an animal subject, preferably a neonatal, juvenile or paediatric animal subject. In all embodiments of the invention, the adjuvant may induce the cytokines directly or indirectly via AIM2, AIM-like receptors (ALRs) or IFI16.

A second embodiment of the invention provides an immunogenic pharmaceutical composition comprising an adjuvant which promotes the induction of cytokines such as interleukin-1 (IL-1), type 1 interferons (IFNs), such as IFNα and IFNβ, type 2 interferons, such as IFNγ, and/or TNF response, such as TNFα; and a pharmaceutically acceptable carrier or excipient.

A third embodiment of the invention provides a vaccine composition comprising an antigen and an adjuvant which promotes the induction of cytokines such as interleukin-1, type 1 interferons (IFNs), such as IFNα, and IFNβ, type-2 interferons such as IFNγ and/or TNF response, such as TNFα.

A fourth embodiment provides an immunogenic composition or vaccine composition as defined in herein for use in eliciting or enhancing an immune response in a neonatal, juvenile or paediatric animal subject; preferably for use in prevention of bacterial, viral and/or parasitic infections in a neonatal, juvenile or paediatric animal subject.

A fifth embodiment provides a method of eliciting or enhancing an immune response in a subject, the method comprising administering to a neonatal, juvenile or paediatric animal subject a composition comprising an adjuvant which promotes the induction of cytokines such as interleukin-1, type 1 interferons (IFNs), such as IFNα, IFNγ and IFNβ, type-2 interferons such as IFNγ and/or TNF response, such as TNFα.

A sixth embodiment provides an adjuvant which targets intracellular nucleic acid sensors for use in eliciting or enhancing a type 1 interferon response in a non-human neonatal or juvenile animal subject; preferably a non-human neonatal animal. Ideally, the adjuvant is one which promotes the induction of cytokines selected from interleukin-1 (IL-1), type 1 interferons (IFNs), such as IFNα, IFNβ, and type 2 interferons, such as IFNγ, and/or tumour necrosis factor (TNF) response, such as TNFα, to elicit or enhance an immune response.

A seventh embodiment provides the use of the adjuvant of the invention for the manufacture of a medicament for eliciting or enhancing an immune response in an animal subject; or for the prophylaxis and/or treatment of infections, such as bacterial, viral and/or parasitic infections.

Advantageous embodiments of each aspect of the invention are provided in the dependent claims.

DETAILED DESCRIPTION OF THE INVENTION

In this specification, the term 'neonatal' will be understood to understood to cover the time period when the innate immune system is not fully developed. Due to the unique nature of the neonatal immune system which is specifically adapted to postnatal life, but simultaneously susceptible to infection and suboptimal vaccine responses, the burden of disease is high during this time period. Specifically, neonatal covers the time period post-transfer of maternal immunoglobulins. This is typically up to week 4, for example from day 0 to day 28 in cattle or other animals, and from day 0 to day 30 in humans. Furthermore, in the same manner that the neonatal innate immune responses are not fully developed, it has been established that the paediatric or juvenile innate immune system does not resemble that of an adult until puberty and have quantitatively distinct immune systems to that of mature immune systems (Vaccine responses in newborns' Anja Saso & Beate Kampmann, Semin Immunopathol (2017) 39:627-642; Neonatal innate TLR-mediated responses are distinct from those of adults' Kollmann et al J Immunol. 2009 Dec. 1; 183(11):7150-60; Immune responses in neonates' Basha et al Expert Rev Clin Immunol. 2014 September; 10(9):1171-84; Editorial: The Neonatal Immune System: A Unique Host-Microbial Interface Bliss J. and Wynn J. Front. Pediatr., 21 Dec. 2017).

In this specification, it will be understood that the terms 'paediatric' and 'juvenile' which refer to human and non-human animals are interchangeable.

As defined in the claims the present invention is directed to an adjuvant which promotes the induction of cytokines such as interleukin-1 (IL-1), type 1 interferons (IFNs), such as IFNα, and IFNβ, type 2 interferons, such as IFNγ, and/or tumour necrosis factor (TNF) response, such as TNFα, for use in eliciting or enhancing an immune response in an animal subject, preferably a neonatal, juvenile or paediatric animal subject. In all embodiments of the invention, the adjuvant may induce the cytokines directly or indirectly via AIM2, AIM-like receptors (ALRs) or IFI16.

The following passages describing the adjuvant of the invention in more detail will be understood to be all embodiments of the invention described above.

Ideally, the adjuvant of the invention aims to elicit or enhance an innate or adaptive immune response, including an antigen-specific immune response, eliciting or enhancing T helper 1 (Th1) immune response, gamma-interferon-inducible (IFI-16) gene expression, Ifi-16 protein expression, AIM2 gene or protein expression or AIM-like receptor (ALR) gene or protein expression or enhancing an IL-1 response.

The adjuvant of the invention promotes, either directly or indirectly via an upstream pathway (such as via ALRs, AIM-2, IFI16), the induction of interleukin-1 (IL-1), type 1 interferons (IFNs), such as IFNα, and IFNβ, type 2 interferons, such as IFNγ, and/or tumour necrosis factor (TNF) response, such as TNFα.

Thus, by targeting intracellular CNA sensors a type1 IFN response or Th1 response can be elicited to stimulate the innate immune response.

According to a preferred embodiment of the invention, the adjuvant is a cytosolic nucleic acid (CNA) sensor agonist or synthetic analog or mimic thereof, preferably selected from:

double stranded DNA (dsDNA);

double stranded RNA (dsRNA);

cyclic guanosine monophosphate-adenosine monophosphate (cGAMP); or a synthetic analog or mimic thereof.

According to a still preferred embodiment, the adjuvant is dsRNA mimic polyinosinic-polycytidylic acid (Poly(I:C));

dsDNA mimic poly(deoxyadenylic-thymidylic) acid (Poly(dA:dT));

5' triphosphate double stranded RNA (ppp-dsRNA); or

3'-haripin RNA (hpRNA).

According to a still preferred embodiment of the invention, there is provided an adjuvant comprising a dsDNA sensing receptor agonist or synthetic analog or mimic thereof, ideally Poly(deoxyadenylic-thymidylic) acid (Poly (dA:dT)), for use in eliciting or enhancing an immune response in a neonatal, juvenile or pediatric animal subject.

Ideally, the adjuvant is packaged in a delivery system, preferably a nanoparticle, cationic or polymeric delivery system, for delivery into cytoplasm of a cell (to form a so called cytosolic nucleic acid). Any alternative suitable conventional delivery system may be used.

The adjuvant of the invention may ideally be used in the prophylaxis and/or treatment of infections, such as bacterial, viral and/or parasitic infections.

Additionally, there is also provided the use of the adjuvant of the invention for the manufacture of a medicament for the prophylaxis and/or treatment of infections, such as bacterial, viral and/or parasitic infections.

The adjuvant of the invention has both human and non-human animal applications. For example, the adjuvant of the invention may advantageously be used in the prophylaxis and/or treatment of bovine tuberculosis and paratuberculosis (Johne's disease) in cattle and sheep.

The invention also provides an immunogenic pharmaceutical composition comprising an adjuvant, as described above, which promotes the induction of cytokines such as interleukin-1 (IL-1), type 1 interferons (IFNs), such as IFNα and IFNβ, type 2 interferons, such as IFNγ, and/or TNF response, such as TNFα; and a pharmaceutically acceptable carrier or excipient; and a vaccine composition comprising an antigen and an adjuvant, as described above, which promotes the induction of cytokines such as type 1 interferons (IFNs), such as IFNα, IFNγ and IFNβ, type 2 interferons, such as IFNγ, and/or TNF response, such as TNFα.

It will be understood that the immunogenic composition or vaccine composition of the invention may be for use in eliciting or enhancing an immune response in an animal subject, preferably a neonatal, juvenile or paediatric animal subject. Advantageously, the immunogenic composition or vaccine composition of the invention may be for use in prevention of bacterial, viral and/or parasitic infections in a neonatal, juvenile or paediatric animal subject. Additionally, there is provided the use of the immunogenic composition or vaccine composition of the invention for the manufacture of a medicament for eliciting or enhancing an immune response in a neonatal or paediatric animal subject, preferably for use in prevention of bacterial, viral and/or parasitic infections in a neonatal, juvenile or paediatric animal subject.

The invention aso provides a method of eliciting or enhancing an immune response in a subject, the method comprising administering to a subject, preferably a neonatal, juvenile or paediatric animal subject a composition, such as an immunogenic composition or vaccine composition described above, comprising an adjuvant which promotes the induction of cytokines such as interleukin-1 (IL-1), type 1 interferons (IFNs), such as IFNα, IFNγ and IFNβ, type 2 interferons, such as IFNγ, and/or TNF response, such as TNFα.

It will be understood that the invention as defined above is ideally applicable to neonatal, juvenile and/or paediatric animal or human populations. In this manner, the adjuvant of the invention is applicable for use in population subset in which the innate immune system is not yet fully developed or mature, which in humans, for example, does not happen until puberty. Neonatal and/or paediatric populations cover age ranges up to 12 years including:

From 0 to 30 days (neonate)
From 1 month to 2 years (infant)
From 2 years to 6 years (young child)
From 6 years to 12 years (child)
Particularly preferred age ranges in include from 0 to 6 months, from 0 to 9 months, from 4 months to 24 months, from 2 years to 5 years and from 6 years to 11 years.

Further details on the invention are provided in the following human and animal population sections.

Human Population

A number of publications have identified that that the neonatal immune system has a diminished ability to generate a Th1-polarising environment in response to most TLR stimuli (e.g. Protecting the Newborn and Young Infant from Infectious Diseases: Lessons from Immune Ontogeny.

Kollmann T R, Kampmann B, Mazmanian S K, Marchant A, Levy O. Immunity. 2017 Mar. 21; 46(3):350-363). We have validated these findings and confirm that TLR agonists LPS and unmethylated CpG-rich DNA do not induce a robust IFN response in neonatal cord blood. Importantly, we have found that it is not simply that the neonatal immune system is immune-compromised, in terms of TLR responses, when compared with the adult system, but that it is in fact qualitatively different. Thus, the neonatal response, to TLR ligands at least, appears to enhance those cytokines that would be predicted to skew the immune system in favour of a Th2/Th17 response and away from a Th1 response.

We have identified that activation of intracellular cytoplasmic PRRs with nucleic acid formulations, such as
Poly(I:C) (double stranded RNA);
Poly(dA:dT) (double stranded DNA); or
direct STING ligand cGAMP
elicits a robust innate immune response in neonatal and/or paediatric blood that is not only equal to that observed in adult blood but is in fact enhanced when compared to that of the adult.

Based on our findings, we propose that activating a family of intracellular cytosolic nucleic acid sensors belonging to the innate immune system in a format that would allow the nucleic acid to gain access to the intracellular cytoplasmic PRRs during the formulation of vaccines, or other immunogenic compositions, will allow for effective vaccination in a neonatal and/or paediatric population, due to the ability of the neonatal and infant immune system to respond to such stimuli.

Known cytosolic DNA sensors include (but are not limited to):
DNA-dependent activator of IFN-regulatory factors (DAI), binds cytosolic double stranded DNA and leads to the production of type I IFNs through the Interferon Regulatory Factor 3 (IRF3) pathway;
IF116 and DDX41 which act through the endoplasmic reticulum (ER)-resident transmembrane protein stimulator of IFN genes (STING), an essential signaling adaptor activating IRF3 to trigger transcriptional induction of type I IFN genes and interferon inducible proteins.

Known cytosolic RNA sensors include (but are not limited to):
retinoic acid-inducible gene (RIG-I)-like receptors (RLRs), which include RIG-I and the melanoma differentiation associated gene 5 protein (MDA-5);
RIG-I and MDA-5 signal through TKK-binding kinase (TBK1) upon recognition of foreign cytosolic double-stranded RNA, leading to the activation of transcription factors such as IRF3 to control the transcription of genes encoding interferons and other cytokines;
the protein laboratory of genetics and physiology 2 (LGP2) has recently been described to facilitate RNA recognition by RIG-I and MDA-5.

We have found that use of the adjuvants of the present invention enhances cytokine (type 1 IFN, IL-12p70 and IFNgamma) production driving cell mediated immunity when compared with current adjuvants.

Advantageously, the use of these adjuvants in a format that will activate the intracellular cytosolic nucleic acid sensors in vaccine or other immunogenic formulations will provide age-appropriate "adjuvants" for vaccine-preventable diseases potentially eliminating the need for booster injections and preventing life-threatening invasive infection in early life. In this manner, the adjuvants of the invention are formulated to enter the cytosol so they can activate the intracelluar cytosolic nucleic acid (CNA) sensor target of interest. For example, the adjuvant, such as Poly(I:C) or Poly(dA:dT), may be packaged in a delivery system, preferably a nanoparticle, cationic or polymeric delivery system, for delivery into cytoplasm of a cell. This is discussed below.

In the face of rising antibiotic resistance, improving vaccine efficacy from birth and increasing vaccine compliance through reducing the need for booster doses, is of critical importance for safeguarding global health of human and animal populations.

In addition, these adjuvants can be used in an immunogenic composition to enhance or boost an immune response as an immunostimulant in cases where a child's immune system is suppressed and could benefit from it (e.g. chronic infection or cancer).

Nucleic acids are not very efficient when administered alone, which means that the use of appropriate methods for in-vivo transfection of these molecules into targeted cells is fundamental. Examples of these techniques are the use of viral and non-viral vectors to transfer the nucleic acid to the cells nucleus. While viral vectors have demonstrated superior effectiveness for nucleic acid transfer, viral vectors have many drawbacks. Non-viral carrier (synthetic vector) delivery systems offer several advantages that have significantly advanced their development. These include improved biosafety and flexibility. They are also simpler to manufacture and modify compared to viral vectors.

It will be understood that the adjuvant must be packaged for delivery to the cytoplasm of the cell. Suitable examples of delivery systems include Nanoparticle encapsulation;

Polymer based nucleic acid nanocarriers;

Cationic liposomes and polymers;

Rigidified liposomes;

Cell-penetrating peptide (CPP) complexes;

Receptor targeting methods; and

Ultra high affinity dsRNA binding protein carriers.

Preferably, the adjuvant may be packaged in a nanoparticle, cationic or polymeric delivery system to facilitate delivery into cytoplasm of a cell.

Cationic lipids and cationic polymers have been widely studied in the context of non-viral gene delivery systems. The discovery of lipofection has prompted the use of cationic lipids for nucleic acid delivery in-vitro and in-vivo. Cationic lipids form cationic liposomes that electrostatically bind to anionic nucleic acids, forming complexes (lipoplexes) that are taken up into cells by endocytosis.

According to a preferred embodiment, Poly(I:C) or Poly(dA:dT) is packaged in a polymeric system that efficiently delivers the nucleic acid into the cytoplasm.

The adjuvant of the invention is delivered to the cytoplasm of the target cell, which includes dendritic cells, monocytes and macrophages.

This aspect of the invention, will now be described by the following non-limiting sequentially numbered embodiments:

1. An adjuvant which promotes the induction of interleukin-1 (IL-1), type 1 interferons (IFNs), such as IFNα and IFNβ, type 2 interferons, such as IFNγ, and/or TNF response, such as TNFα, for use in eliciting or enhancing an immune response in neonatal or paediatric animals.

2. An adjuvant according to embodiment 1 for use in eliciting or enhancing a desired antigen-specific immune response in neonatal or paediatric animals.

3. An adjuvant according to embodiment 1 or 2 for use in eliciting or enhancing of T helper 1 (Th1) immune response.

4. An adjuvant according to any of the preceding embodiments for use in the prophylaxis and/or treatment of infection, such as bacterial or viral infections.

5. An adjuvant according to any of the preceding embodiments for use in eliciting or enhancing an immune response wherein the adjuvant is a cytosolic nucleic acid sensor agonist or synthetic analog or mimic thereof.

6. An adjuvant according to any of the preceding embodiments for use in eliciting or enhancing an immune response wherein the adjuvant is selected from:

double stranded DNA (dsDNA);

double stranded RNA (dsRNA);

cyclic guanosine monophosphate-adenosine monophosphate (cGAMP); or synthetic analog or mimic thereof.

7. An adjuvant according to any of the preceding embodiments for use in eliciting or enhancing an immune response wherein the adjuvant is selected from:

dsRNA mimic polyinosinic-polycytidylic acid (Poly(I:C));

dsDNA mimic poly(deoxyadenylic-thymidylic) acid (Poly(dA:dT)); or other suitable mimics of nucleic acid sensing receptor agonist.

8. An adjuvant according to any of the preceding embodiments for use in eliciting or enhancing an immune response wherein the adjuvant is Poly(deoxyadenylic-thymidylic) acid (Poly(dA:dT)).

9. An adjuvant according to any of the preceding embodiments for use in eliciting or enhancing an immune response wherein the adjuvant is adapted for delivery to the cytoplasm of a cell.

10. An adjuvant according to any of the preceding embodiments, preferably Poly(I:C) or Poly(dA:dT), for use in eliciting or enhancing an immune response wherein the adjuvant is packaged in a delivery system, preferably a nanoparticle, cationic or polymeric delivery system, for delivery into the cytoplasm of a cell.

11. An adjuvant according to any of the preceding embodiments for use in eliciting or enhancing an immune response in a human.

12. An adjuvant according to any of the preceding embodiments for use in eliciting or enhancing an immune response in a neonatal and/or paediatric population.

13. An adjuvant according to any of the preceding embodiments for use in eliciting or enhancing an immune response for a neonatal and/or paediatric human population up to 11 years, preferably up to 2 years, more preferably up to 24 months.

14. An adjuvant according to any of the preceding embodiments for use in eliciting or enhancing an immune response for a neonatal and paediatric human population from 6 to 11 years, preferably from 2 to 5 years, more preferably from 4 months to 24 months.

15. An immunogenic pharmaceutical composition comprising an adjuvant which promotes the induction of type 1 interferons (IFNs), such as IFNα, IFNγ and IFNβ, and/or TNF response, such as TNFα; and a pharmaceutically acceptable carrier or excipient.

16. A vaccine composition comprising an antigen; and an adjuvant for eliciting or enhancing an immune response in a neonatal or paediatric animal population which promotes the induction of interleukin-1, type 1 interferons (IFNs), such as IFNα, and IFNβ, type 2 interferons, such as IFNγ, and/or TNF response, such as TNFα

17. The vaccine composition according to embodiment 16 for the prevention of bacterial and/or viral infections in neonatal and paediatric human or animal populations.

18. A method of eliciting or enhancing an immune response, optionally a desired antigen-specific immune response, in a subject, the method comprising administering to a neonatal or paediatric animal subject a composition that comprises an adjuvant which promotes the induction of interleukin-1, type 1 interferons (IFNs), such as IFNα, and IFNβ, type-2 interferons such as IFNγ, and/or TNF response, such as TNFα.

Animal Population

Animals (i.e. non-human animals) in the first few months after birth are highly susceptible to a number of both bacterial and viral infectious diseases. For example, cattle in the first 6 months after birth are highly susceptible to paratuberculosius (Johne's disease). This imposes a major economic burden on the agricultural sector.

It is known that there is a deficiency in the induction of T helper 1 (Th1) cell responses over this period which may explain this increased susceptibility to intracellular bacteria and viruses. Th1 responses are an essential component of the immune response to many infections, particularly intracellular bacteria and viruses. Neonatal cattle are highly susceptible to a number of bacterial infections and the deficiency in producing interferon gamma is thought to underly this. We have found that stimulation of cells with the toll like receptor ligand LPS does not significantly enhance interferon gamma responses.

We have discovered that adjuvants which promote the induction of type 1 interferons can overcome the deficiency in interferon gamma production by peripheral blood mononuclear cells from animals over the first few months of life, preferably from 0-10 months. Specifically, we found that transfection of the adjuvant Poly (deoxyadenylic-thymidylic) acid (Poly(dA:dT)) promotes type 1 interferon dependent enhancement of interferon gamma production in PBMCs. This strategy provides a valuable means to enhance Th1 immune responses in neonatal cattle and facilitate the generation of improved vaccines/immunogenic compositions for animals in general.

Furthermore, as cattle (in contrast to humans) only have a single PYHIN gene, IFI16, it is likely that (Poly(dA:dT)) induction of interleukin 1 and type 1 IFN is IFI16 dependent. Our findings implicate IFI16 as a key target for the promotion of Th1 responses in neonatal animals such as cattle.

This discovery highlights the potential new adjuvants for use in vaccines or immunogenic compositions targeted to neonatal animals, such as cattle, for the treatment or prophylaxis of infections or other diseases outlined below.

Johne's or paratuberculosis disease is a bacterial disease of cattle and other ruminants. It is caused by the bacterium *Mycobacterium avium* subspecies *paratuberculosis* (MAP).

Other infectious diseases of cattle include:

| Bacterial | Viral | Parasites |
|---|---|---|
| Respiratory diseases | Respiratory diseases | Coccidiosis |
| *Mycoplasma bovis*; | RSV, PI3, IBR, BRCV and | Cryptosporidium |
| *Pasteurella, Haemophilus*; | BVDV | |
| *Mycoplasma bovis*; | | |
| *Mycobacterium bovis*; | | |
| Enteric bacteria | Enteric viruses | |
| *Mycobacterium avium* | Rotavirus | |
| subsp. *Paratuberculosis* | Coronavirus | |
| (MAP); | | |
| *Salmonella/E. coli*; | | |

According to a preferred embodiment of the invention any adjuvant which targets IFI-16 may be used including: -Poly (deoxyadenylic-thymidylic) acid (Poly(dA:dT)) and related adjuvants;

non-AT rich dsDNA of appropriate length; and adjuvants which drive type 1 IFN expression; promotes intracellular release of self nucleic acids, such as chitosan.

Adjuvants which drive type 1 IFN expression include chitin-derived polymers and other adjuvants that can release self DNA into the cytoplasm or toll like receptor agonists, agonists of TLR3, TLR7, TLR8, TRL9 or any suitable adjuvants that targets the cGAS-STING pathway (e.g. Carroll E C, Jin L, Mori A, Muñoz-Wolf N, Oleszycka E, Moran H B T, Mansouri S, McEntee C P, Lambe E, Agger E M, Andersen P, Cunningham C, Hertzog P, Fitzgerald K A, Bowie A G, Lavelle E C: The Vaccine Adjuvant Chitosan Promotes Cellular Immunity via DNA Sensor cGAS-STING-Dependent Induction of Type I Interferons' Immunity 2016 Mar. 15; 44(3):597-608).

A preferred adjuvant is Poly(dA:dT). Poly(dA:dT) is a synthetic analog of B-DNA and is a repetitive double-stranded DNA (dsDNA) sequence of poly(dA-dT)•poly(dT-dA). Poly(dA:dT) may be administered as a salt form such as a poly(deoxyadenylic-deoxythymidylic) acid sodium salt.

Any suitable conventional delivery system may be used which delivery the adjuvant into the cytoplasm of the cell (refer to human population section above). The skilled person will understand the adjuvant could be incorporated in liposomes, polymer nanoparticles or microparticles, solid lipid microparticles, emulsions, mineral salts for injection into the muscle or skin. Alternatively, nasal delivery sprays or other mucosal delivery systems to allow delivery by mucosal routes including the sublingual or oral route may also be considered.

This aspect of the invention, we now be described by the following non-limiting sequentially numbered embodiments:

1. An adjuvant which promotes the induction of type 1 interferons (IFNs), such as IFNα, and IFNβ, for use in eliciting or enhancing an immune response in animals.
2. An adjuvant according to embodiment 1 which promotes the induction of type 1 interferons (IFNs), such as IFNα, and IFNβ, for use in eliciting or enhancing an immune response in neonatal, juvenile or paediatric populations, including animals.
3. The adjuvant according to embodiment 1 or embodiment 2 for use in eliciting a desired antigen-specific immune response.
4. An adjuvant according to any of the preceding embodiments for use in eliciting or enhancing of T helper 1 (Th1) immune responses.
5. An adjuvant according to any of the preceding embodiments for use in eliciting or enhancing gamma-interferon-inducible (IFI-16) gene expression or Ifi-16 protein expression.
6. An adjuvant according to any of the preceding embodiments for use in eliciting or enhancing an IL-1 response.
7. An adjuvant according to any of the preceding embodiments for use in the prophylaxis and/or treatment of infections, including bacterial, viral and/or parasitic infections.
8. An adjuvant according to any of the preceding embodiments wherein the animal is an ungulate is selected from the group consisting of porcine, ovine, bovine, and caprine, preferably livestock, such as cattle, sheep, pigs, goats, horses, donkeys, mules, buffalo, oxen, and camels.
9. An adjuvant according to any of the preceding embodiments wherein the animal is cattle.

10. An adjuvant according to any of the preceding embodiments wherein the animal under 28 days old, preferably neonatal cattle.

11. An adjuvant according to any of the preceding embodiments for use in the prophylaxis and/or treatment of bacterial, viral and/or parasitic diseases, including paratuberculosis (Johne's disease) in cattle and sheep and bovine tuberculosis.

12. An adjuvant according to any of the preceding embodiments wherein the adjuvant targets IFI-16 and is selected from
Poly(deoxyadenylic-thymidylic) acid (Poly(dA:dT)) and related adjuvants.
non-AT rich dsDNA of appropriate length;
type 1 IFN adjuvants.

13. An immunogenic pharmaceutical composition comprising the adjuvant according to any of embodiments 1 to 12, preferably the adjuvant which promotes the induction of type 1 interferons (IFNs), such as IFNα, IFNγ and IFNβ, preferably poly(deoxyadenylic-thymidylic) acid (Poly(dA:dT)) and a pharmaceutically acceptable carrier or excipient.

14. A vaccine composition comprising an antigen and the adjuvant which promotes the induction of type 1 interferons (IFNs), such as IFNα, IFNγ and IFNβ, preferably poly(deoxyadenylic-thymidylic) acid (Poly(dA:dT)).

15. The vaccine composition according to embodiment 13 for the prevention of bacterial, viral and parasitic diseases in neonatal cattle.

16. A method of eliciting or enhancing a desired antigen-specific immune response in a subject, preferably an animal subject, the method comprising administering to the subject a composition that comprises an adjuvant which promotes the induction of type 1 interferons (IFNs), such as IFNα, IFNγ and IFNβ, preferably poly(deoxyadenylic-thymidylic) acid (Poly(dA:dT)).

BRIEF DESCRIPTION OF THE DRAWINGS

The present application will now be described with reference to the accompanying drawings.

(A-G) Adult Peripheral blood mononuclear cells (PBMCs) or neonatal cord blood mononuclear cells (CBMCs) were stimulated with (A) LPS, (B) CpG ODN, (C) CL075, (D) Poly(I:C) transfection or (E) Poly(dA:dT) transfection for 4, 8 or 24 h. Levels of IFNα/β were assayed via HEK-Blue™ IFNα/β SEAP assay. Cell viability, following 24 h stimulation with ligands, was assayed using (F) MTS assay or (G) LDH assay. Data in (A) to (E) are mean±SEM (n≥30 donors in each group). Data in (F) and (G) are mean±SEM (n=10 donors in each group). *P<0.05, P<0.01, *P<0.005. (A) to (E) Kruskal-Wallis non-parametric test with Dunn's post-test was used to compare groups. (F)-(G) P-value was determined by Analysis of variance (ANOVA) and Bonferroni's post-test.

Figure 2:
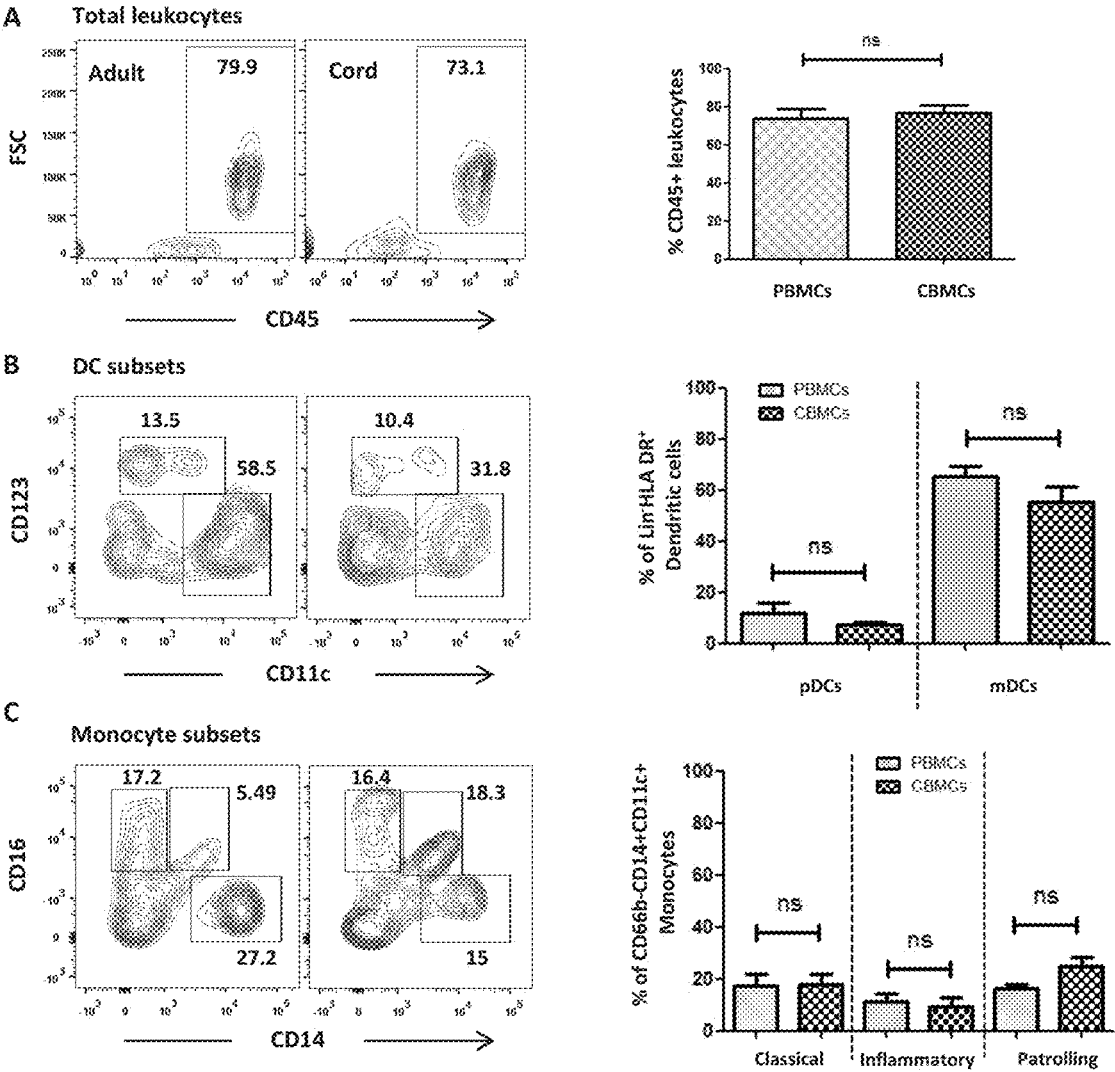
Figure 2:
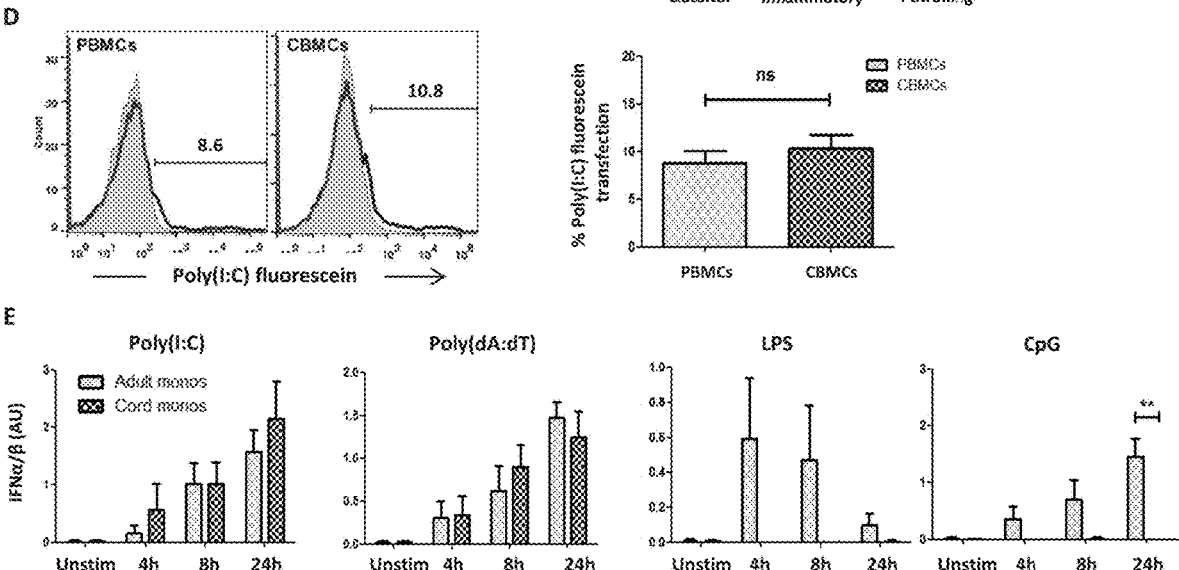

FIG. 2: Frequencies of IFN-producing leukocyte subsets are similar in adult and cord blood.

Adult PBMCs or neonatal CBMCs were isolated and stained with antibodies to distinguish between cell subsets (A) Leukocytes were gated on based on expression of CD45 and percentage leukocyte population was compared between PBMCs and CBMCs. (B) DCs were gated on as follows: CD45+Lin-HLA-DR+ and analysed for percentage frequency of CD11c+CD123− (cDCs) or CD11c-CD123+ (pDCs). (C) Monocytes were gated on as follows: CD45+ CD66b-CD11c+ and analysed for percentage frequency of CD14+CD16− (classical monocytes), CD14 intermediate CD16+ (patrolling monocytes) or CD14+CD16+ (inflammatory monocytes) (D) PBMCs or CBMCs were transfected with Poly(I:C) Fluorescein. Following 24 h incubation the percentage of Fluorescein+ cells was analysed. (E) Monocytes, isolated from adult or cord blood, were transfected with Poly(I:C) or Poly(dA:dT), or treated with LPS or CpG as indicated. Levels of IFNα/β were assayed via HEK-Blue™ IFNα/β SEAP assay. Dotplots & histograms in (A) to (D) are representative of ≥5 individual donors. Graphs in (A) to (E) are mean±SEM (n≥5 donors in each group). **P<0.01. (A)-(D) Student's t-test was used to test for significant difference between groups. (E) P-value was determined by Analysis of variance (ANOVA) and Bonferroni's post-test.

Figure 3:
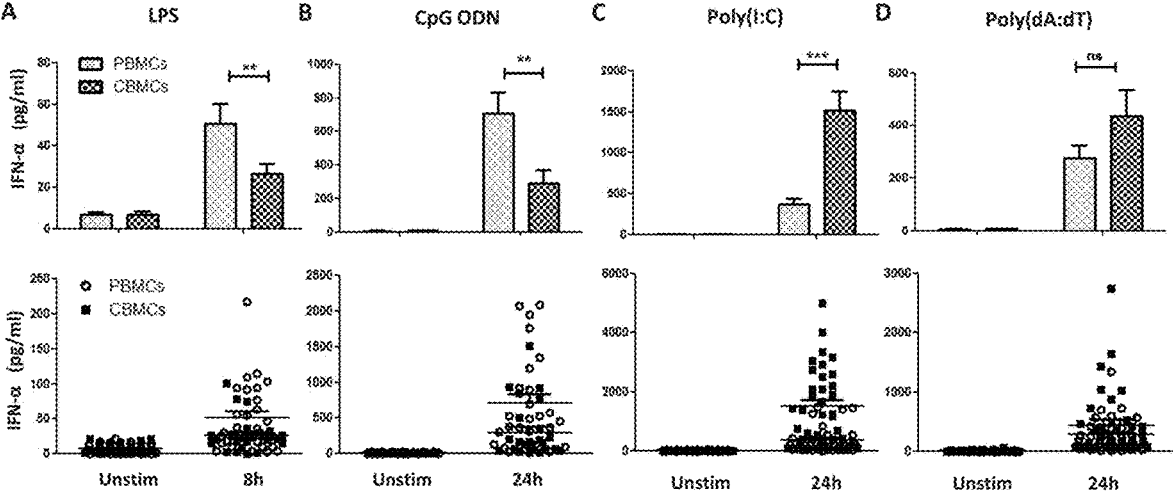
Figure 3:
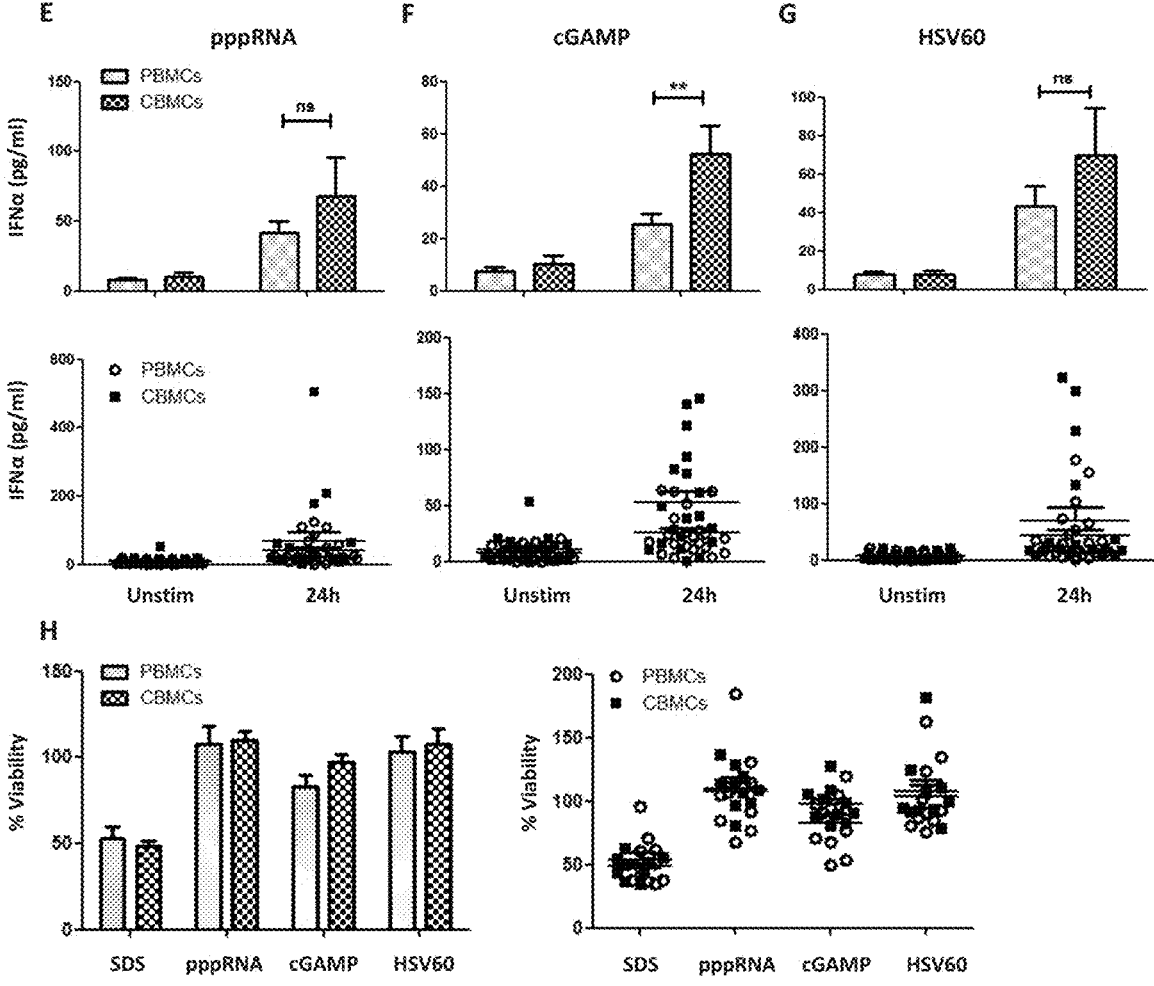

FIG. 3: Neonatal IFNα secretion is attenuated in response to TLR ligation but enhanced in response to cytosolic nucleic acid.

PBMCs or CBMCs were treated with (A) LPS, (B) CpG ODN or transfected with (C) Poly(I:C), (D) Poly(dA:dT), (E) 5' ppp dsRNA, (F) 2'3' cGAMP or (G) HSV60 for 8 or 24 h, as indicated, and IFN-α was measured by ELISA. (H) Cell viability following 24 h treatment was assayed using MTS assay. (A) to (G) graphs show mean±SEM (n≥18 donors in each group). (H) Graph compares mean±SEM of n=10 donors in each group P<0.01, *P<0.005. P-value was determined by Analysis of variance (ANOVA) and Bonferroni's post-test.

Figure 4:
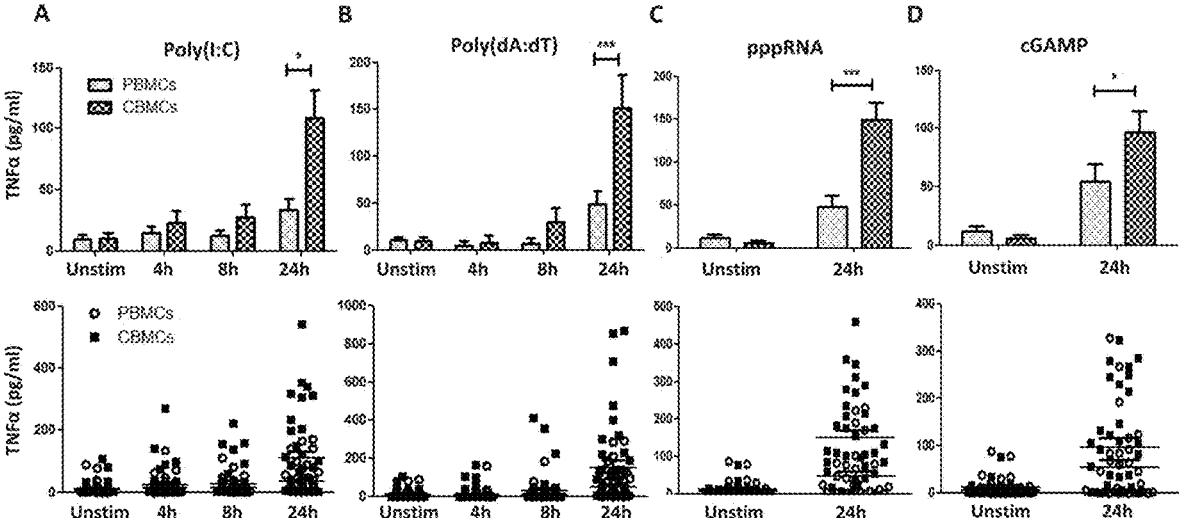
Figure 4:
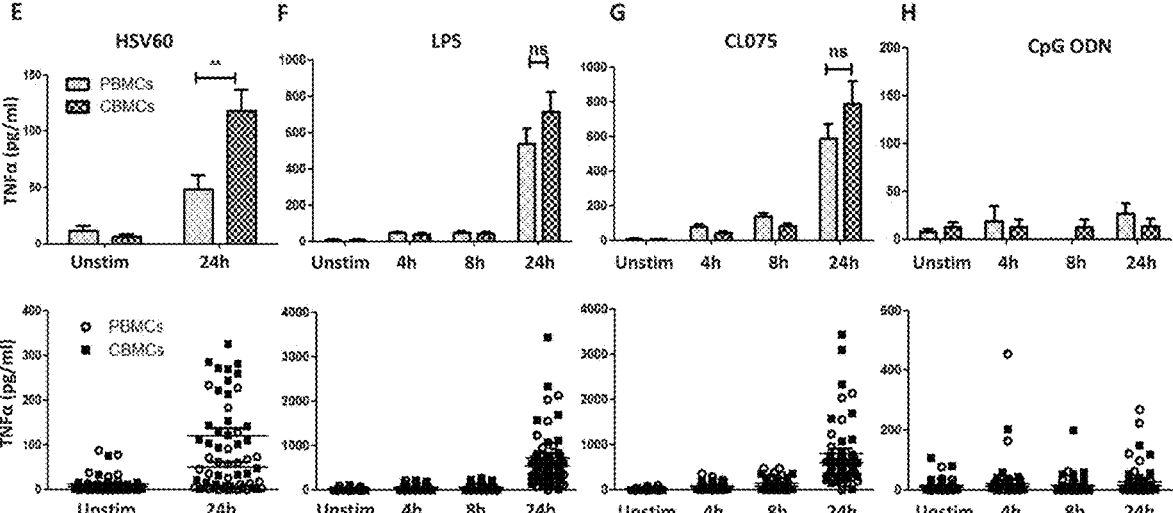

FIG. 4: TNFα secretion from CBMCs is enhanced compared to adult PBMCs in response to a range of cytosolic nucleic acid receptor agonists.

PBMCs or CBMCs were transfected with (A) Poly(I:C), (B) Poly(dA:dT), (C) 5' ppp dsRNA, (D) 2'3' cGAMP, (E) HSV60 or treated with (F) LPS, (G) CL075 or (H) CpG ODN for the indicated timepoints. Following stimulation, supernatant was harvested from the cells and TNFα was measured using HEK-Blue™ TNFα assay and made relative to 125 pg/ml TNFα. Graphs show means±SEM (n≥29 donors in each group). *P<0.05, ***P<0.005. Kruskal-Wallis non-parametric test with Dunn's post-test was used to test for significant difference between groups.

Figure 5:
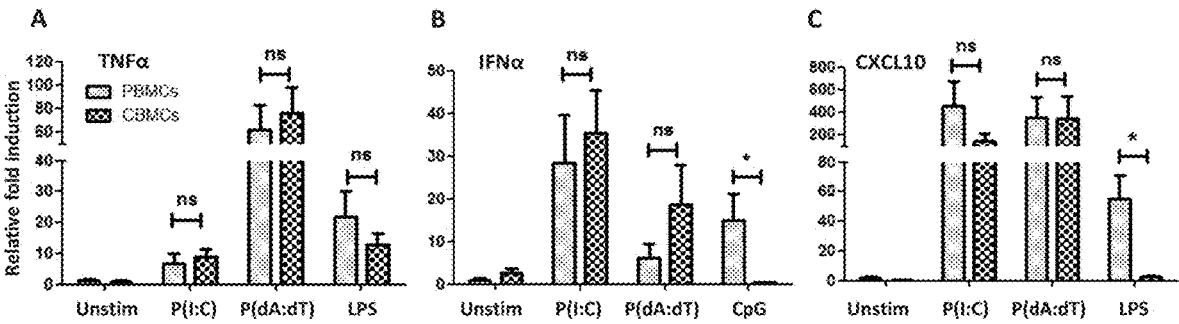
Figure 5:
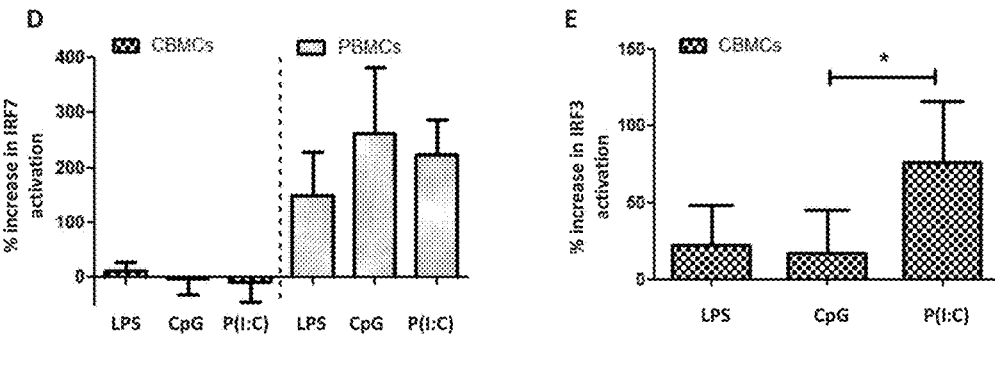
Figure 5:
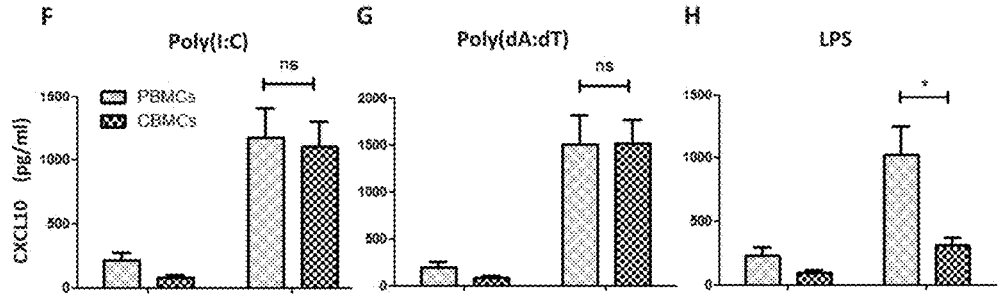

FIG. 5: Impaired TLR-induced IRF3 activation in CBMCs leads to attenuated IFN and ISG responses not observed in response to cytosolic nucleic acid.

PBMCs or CBMCs were transfected with Poly(I:C) or Poly(dA:dT) for 4 h, (A&C), or 24 h (B), or treated with LPS for 2 h (A) or 4 h (C), or CpG ODN for 24 h (B), as indicated. Following stimulation, Trizol extraction of RNA was carried out and induction of (A) TNF-α, (B) IFN-α and (C) CXCL10 mRNA expression was assayed by quantitative RT-PCR, normalized to β-actin and presented relative to untreated, unstimulated adult PBMCs. (D, E) PBMCs or CBMCs were treated with LPS for 15 min, CpG for 1 h or transfected with Poly(I:C) for 1 h, nuclear extracts were harvested and assayed for IRF7 or IRF3 activation via TransAM assays. (F-H) Cells were stimulated with Poly(I:C) or Poly(dA:dT) transfection or LPS as indicated and protein levels of CXCL10 were measured by ELISA. (A-E) Graphs show mean±SEM (n≥4 donors in each group). (F-H) graphs show mean±SEM (n≥29 donors in each group). *P<0.05. P-value was determined by Student's t-test or Kruskal-Wallis with Dunn's post-test.

Figure 6:
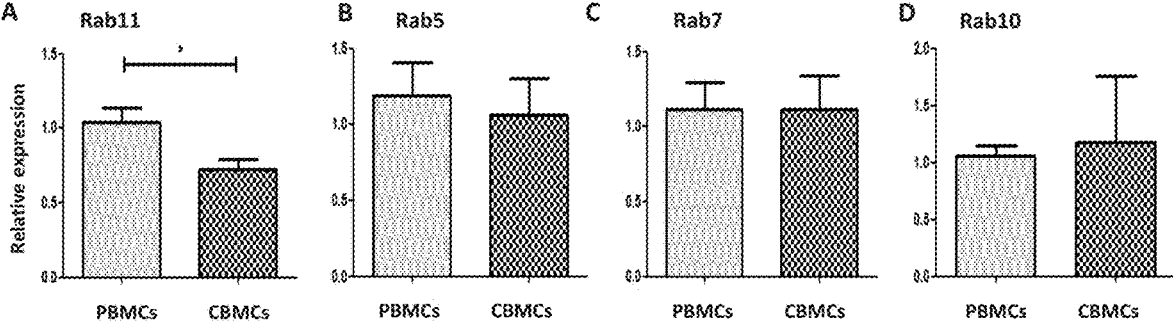
Figure 6:
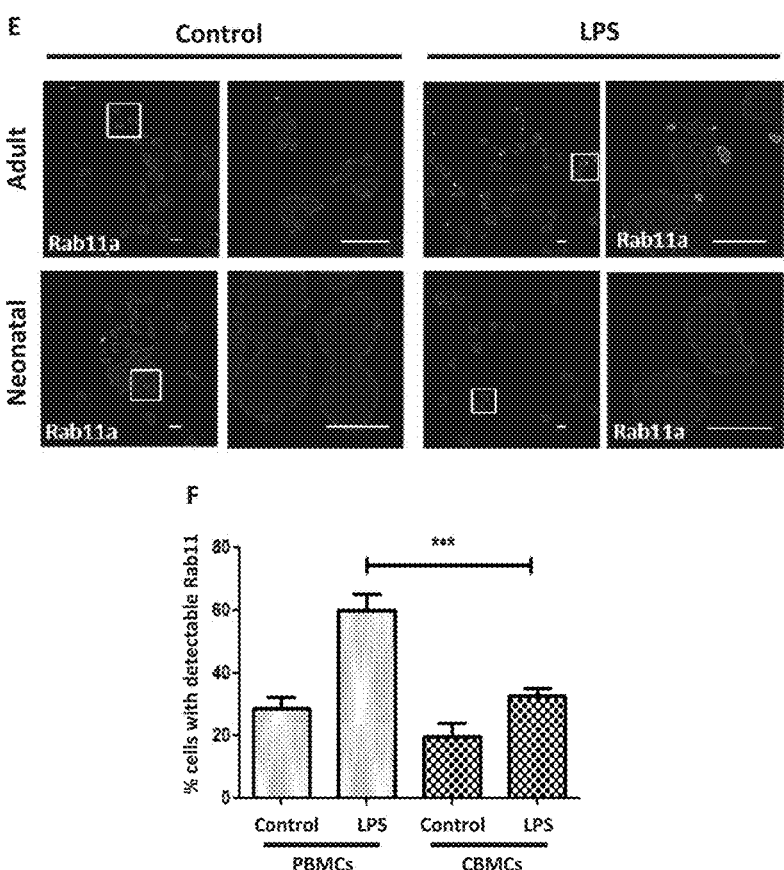
Figure 6:
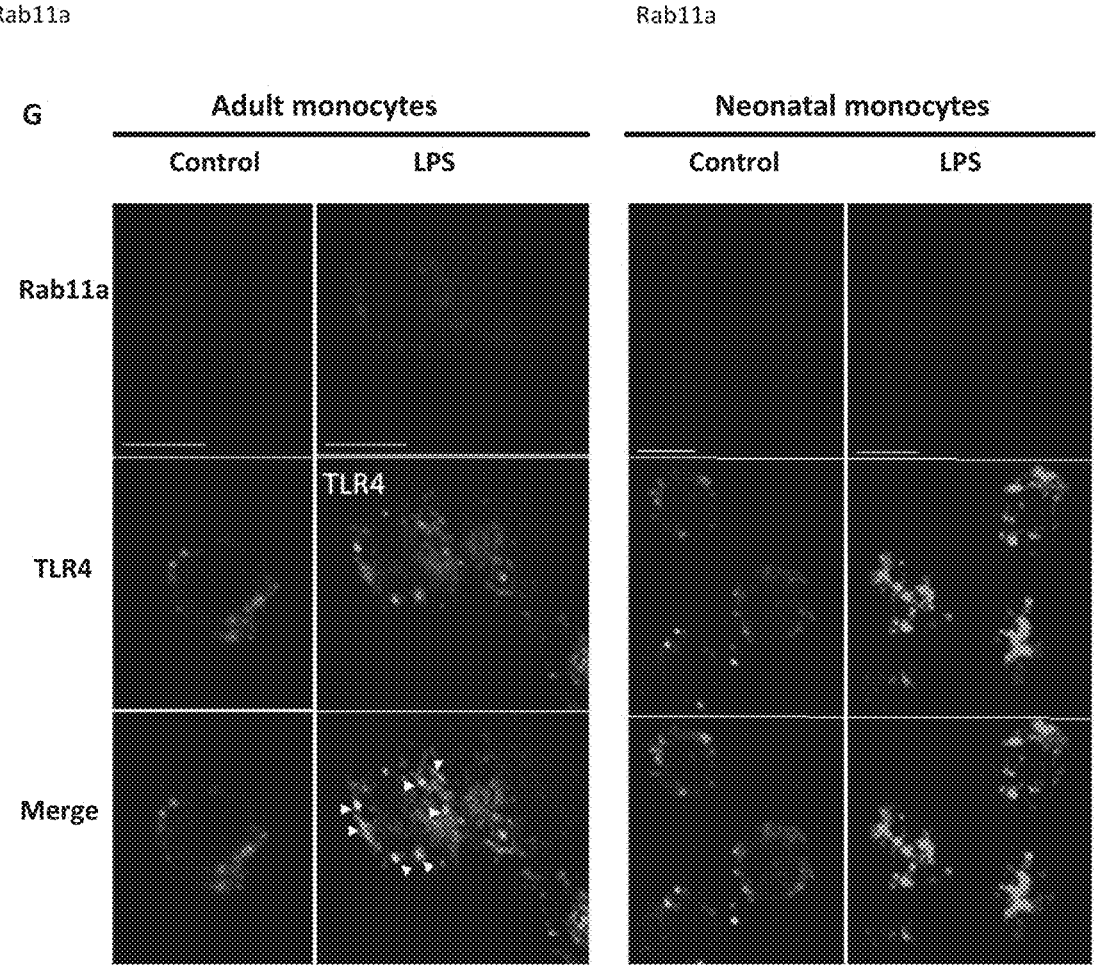

FIG. 6: Attenuation of Rab11-positive endosome formation in LPS-stimulated cord blood monocytes.

(A-D) Trizol extraction of RNA from PBMCs or CBMCs was carried out and expression of (A) Rab11, (B) Rab5, (C) Rab7 or (D) Rab10 mRNA was assayed by quantitative RT-PCR, normalized to β-actin and presented relative to adult PBMCs. (E&G) CD14 positive cells were isolated from adult PBMCs or neonatal CBMCs and left unstimulated or treated with 1 μg/ml LPS for 1 h, as indicated. Cells were stained for Rab11 expression (red) DAPI (blue) or TLR4 (green) as indicated. (F) Cells expressing detectable levels of Rab11 were counted and presented as a percentage of total cells (using >200 cells). (A-D) Graphs show mean±SEM (n≥9 donors in each group). (E&G) Images are representative of 3 separate experiments. All scale bars represent 10 μm (E) and 5 μm (G). (F) Graph shows mean % of cells expressing Rab11 of 200 cells from 3 individual donors (±SEM). *P<0.05, ***P<0.005. P-value was determined by unpaired Student's t-test (A)-(D) or Analysis of variance (ANOVA) and Bonferroni's post-test (F).

Figure 7:
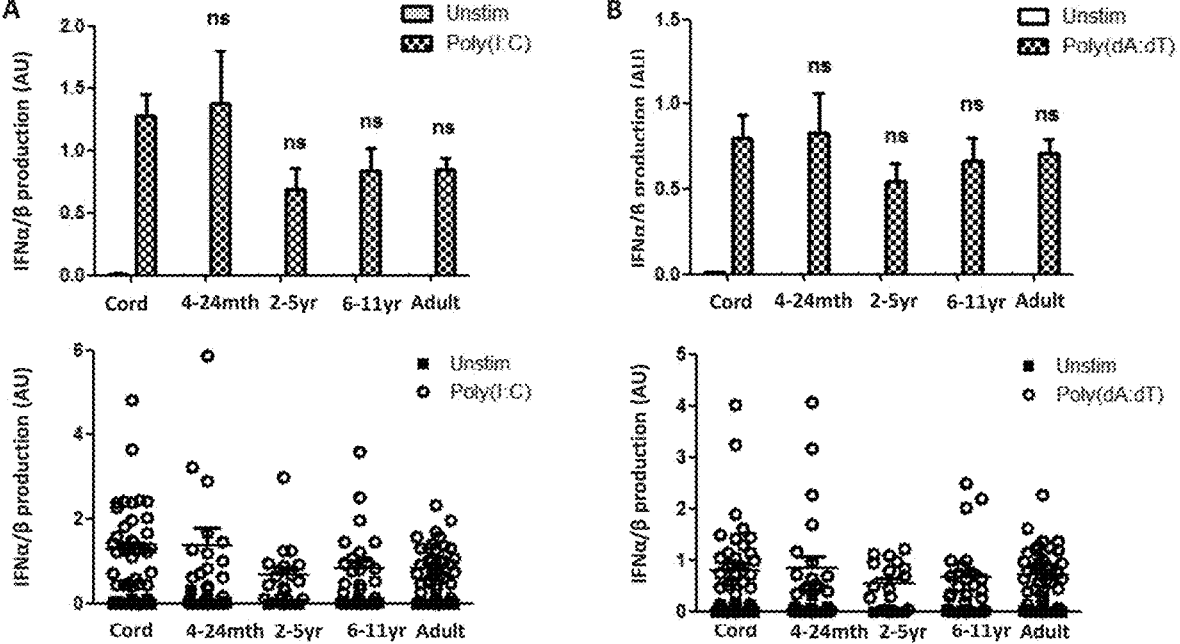
Figure 7:
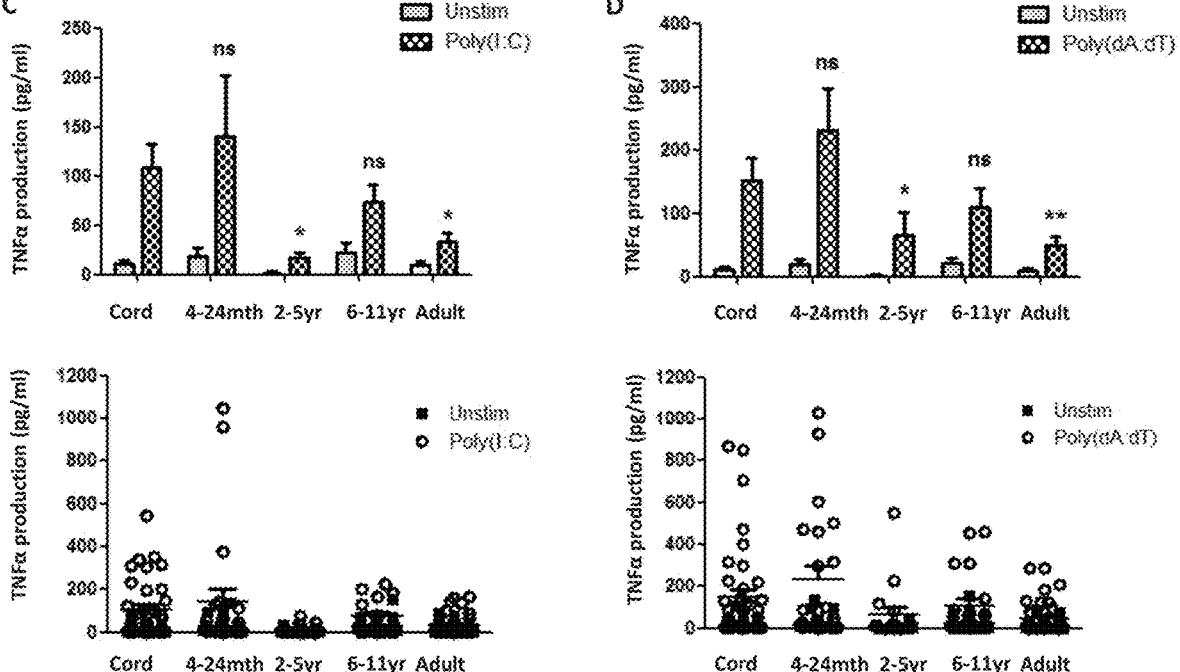

FIG. 7: Cytosolic Nucleic Acids maintain strong type I IFN and TNFα responses in healthy infants and children up to and beyond 24 months.

Mononuclear cells were isolated from cord blood, adult blood or from children's blood collected from otherwise healthy children undergoing surgery for hydrocele repair, umbilical hernia repair, onychocryptosis, orchipexy repair in OLCHC. Cells were transfected with Poly(I:C) or Poly(dA:dT) for 24 h. Following stimulation, supernatant was harvested from the cells and (A, B) IFNα/β and (C, D) TNFα were measured using HEK-Blue™ IFNα/β or TNFα assay and made relative to 25 U/ml IFNα or 500 pg/ml TNFα respectively. (A-D) show mean±SEM (Cord, n≥35; 4-24 mths, n=22; 2-5 yr, n≥16; 6-11 yr n≥18; adult, n≥35). Stimulated populations were compared to stimulated cord mononuclear cells by Mann-Whitney test.

Figure 8:
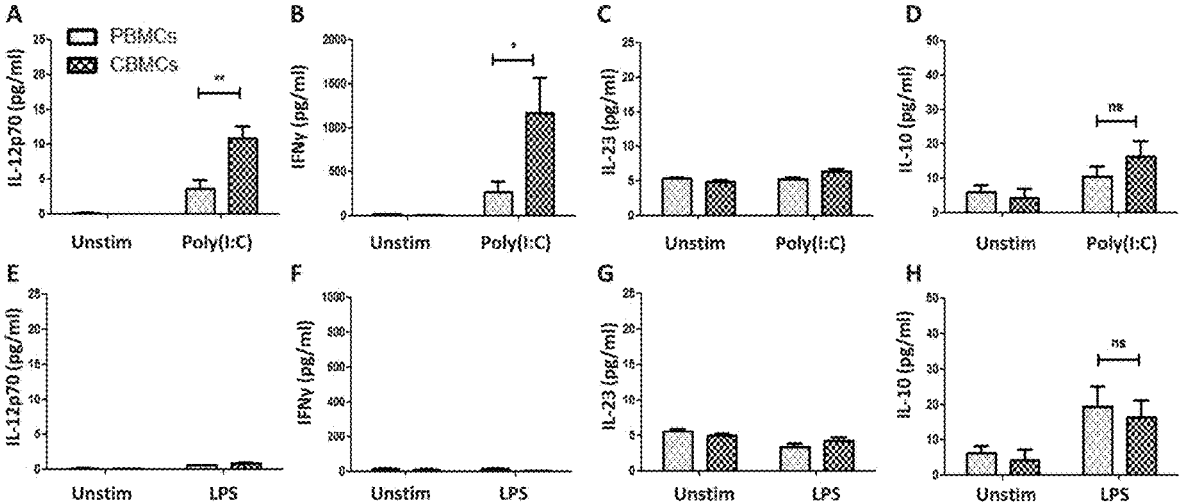
Figure 8:
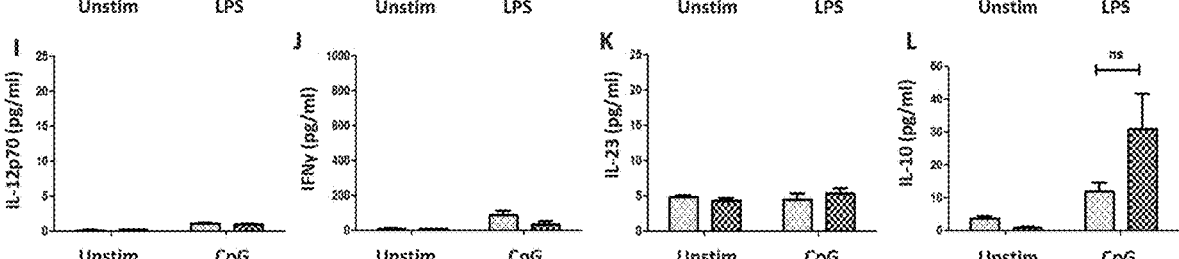

FIG. 8: Cytosolic Poly(I:C) induces Th1 polarising IL-12p70 and IFNγ in CBMCs, whereas TLR4/9 activation does not.

PBMCs or CBMCs were transfected with (A-D) Poly(I:C) for 24 h, treated with (E-H) LPS for 4 h or (I-L) CpG ODN for 24 h and BioLegend LEGENDplex™ Human Inflammation Panels were used to measure the levels of (A, E, I) IL-12p70, (B, F, J) IFN-γ, (C, G, K) IL-23 and (D, H, L) IL-10. Graphs show mean±SEM (n≥16). *P<0.05, P<0.01, *P<0.005. Kruskal-Wallis non-parametric test with Dunn's post-test was used to test for significant differences between groups.

Figure 9:
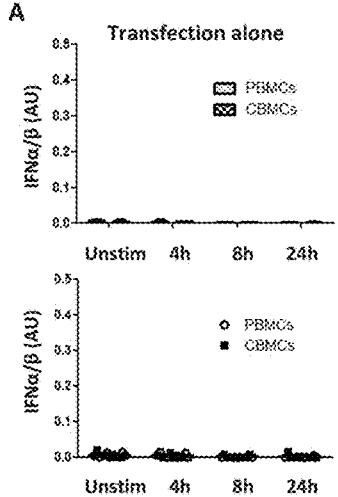
Figure 9:
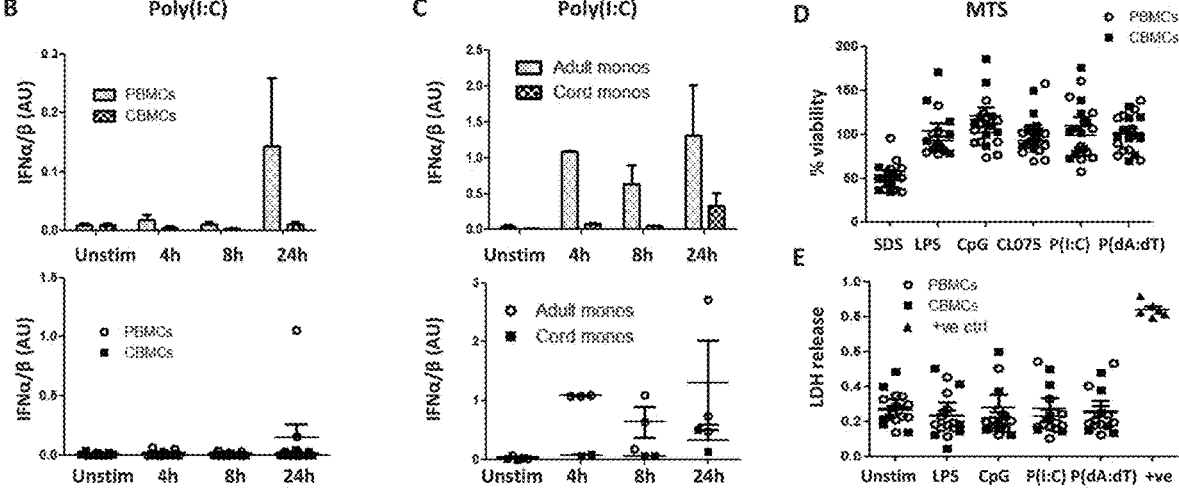

FIG. 9: Transfection alone does not induce type I IFN, while untransfected Poly(I:C) treatment induces less type I IFN in neonatal cells compared to adult cells Adult peripheral blood mononuclear cells (PBMCs) or neonatal cord blood mononuclear cells (CBMCs) (A, B, D & E) or monocytes isolated from adult or cord blood (C) were stimulated with (A) Transfection reagent alone, (B & C) untransfected Poly(I:C) for 4, 8 or 24 h or (D & E) a range of agonists. Levels of IFNα/β were assayed via HEK-Blue™ IFNα/β SEAP assay. Cell viability, following 24 h stimulation with ligands, was assayed using (D) MTS assay or (E) LDH assay. P-value was determined by Analysis of variance (ANOVA) and Bonferroni's post-test.

Figure 10:
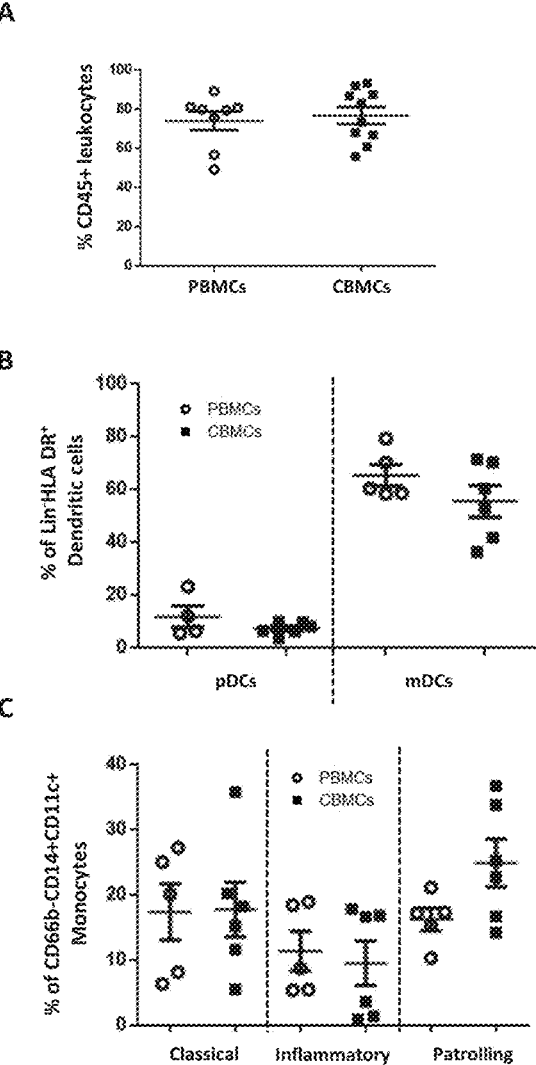
Figure 10:
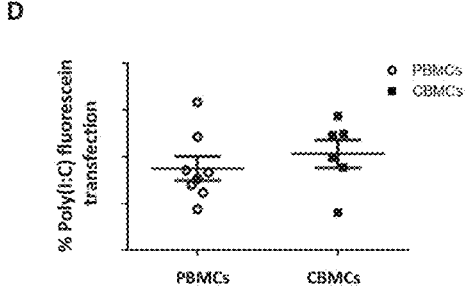
Figure 10:
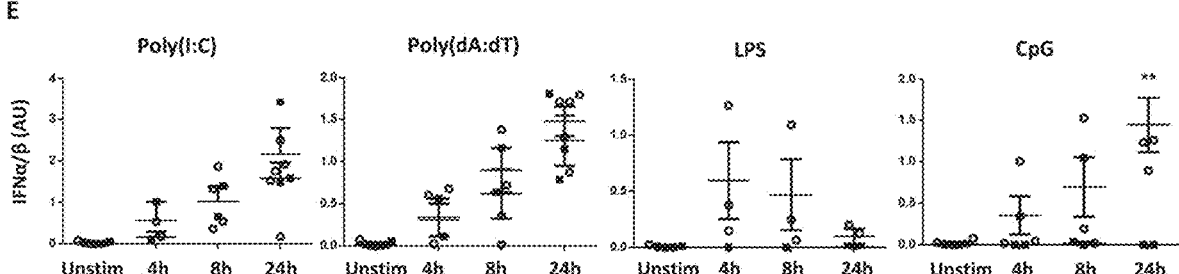

FIG. 10: Frequencies of IFN-producing leukocyte subsets are similar in adult and cord blood PBMCs or CBMCs were isolated and stained with antibodies to distinguish between cell subsets (A) Percentage leukocyte population (CD45+) was compared between PBMCs and CBMCs. (B) DCs were gated on as follows: CD45+Lin−HLA-DR+ and analysed for percentage frequency of CD11c+CD123− (cDCs) or CD11c−CD123+

(pDCs). (C) Monocytes were gated on as follows: CD45+ CD66b−CD11c+ and analysed for percentage frequency of CD14+CD16− (classical monocytes), CD14 intermediate CD16+ (patrolling monocytes) or CD14+CD16+ (inflammatory monocytes) (D) PBMCs or CBMCs were transfected with Poly(I:C) Fluorescein. Following 24 h incubation the percentage of Fluorescein+cells was analysed. (E) Monocytes, isolated from adult or cord blood, were transfected with Poly(I:C) or Poly(dA:dT), or treated with LPS or CpG as indicated. Levels of IFNα/β were assayed via HEK-Blue™ IFNα/β SEAP assay. **P<0.01. (A)-(D) Student's t-test was used to test for significant difference between groups. (E) P-value was determined by Analysis of variance (ANOVA) and Bonferroni's post-test.

Figure 11:
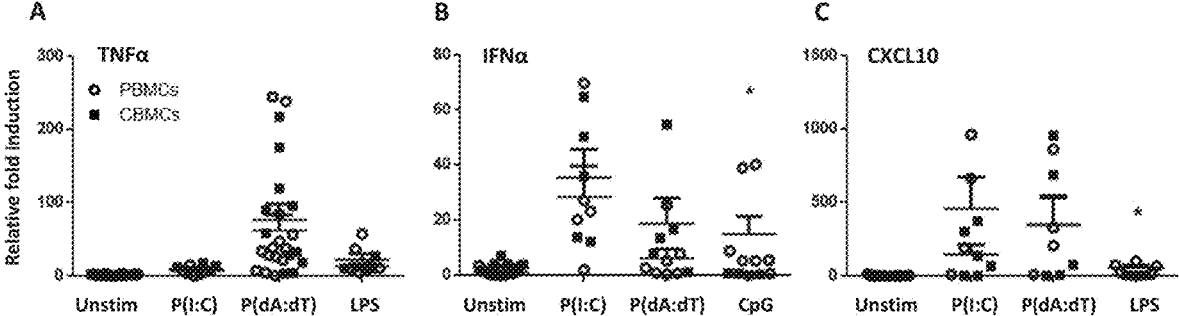
Figure 11:
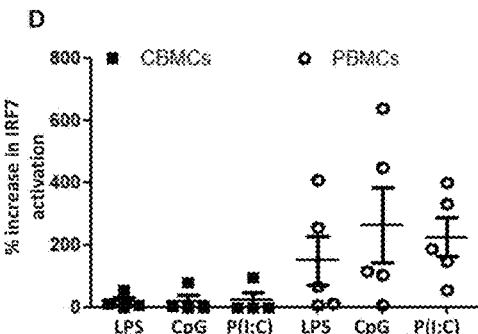
Figure 11:
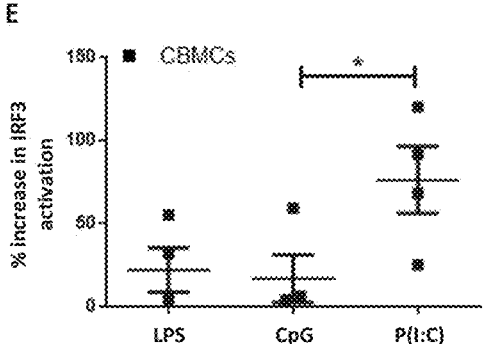
Figure 11:
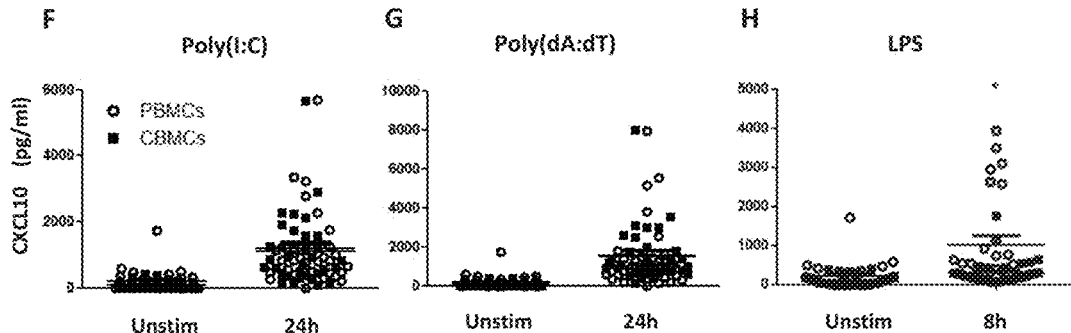

FIG. 11: Impaired TLR-induced IRF3 activation in CBMCs leads to attenuated IFN and ISG responses not observed in response to cytosolic nucleic acid.

PBMCs or CBMCs were transfected with Poly(I:C) or Poly(dA:dT) for 4 h, (A&C), or 24 h (B), or treated with LPS for 2 h (A) or 4 h (C), or CpG ODN for 24 h (B). Following stimulation, (A) TNF-α, (B) IFN-α and (C) CXCL10 mRNA expression was assayed by qRT-PCR, normalized to β-actin and presented relative to untreated, unstimulated adult PBMCs. (D, E) PBMCs or CBMCs were treated with LPS for 15 min, CpG for 1 h or transfected with Poly(I:C) for 1 h, nuclear extracts were harvested and assayed for IRF7 or IRF3 activation via TransAM assays. (F-H) Cells were stimulated with Poly(I:C) or Poly(dA:dT) transfection or LPS, as indicated, and protein levels of CXCL10 were measured by ELISA. *P<0.05. P-value was determined by Student's t-test or Kruskal-Wallis with Dunn's post-test.

Figure 12:
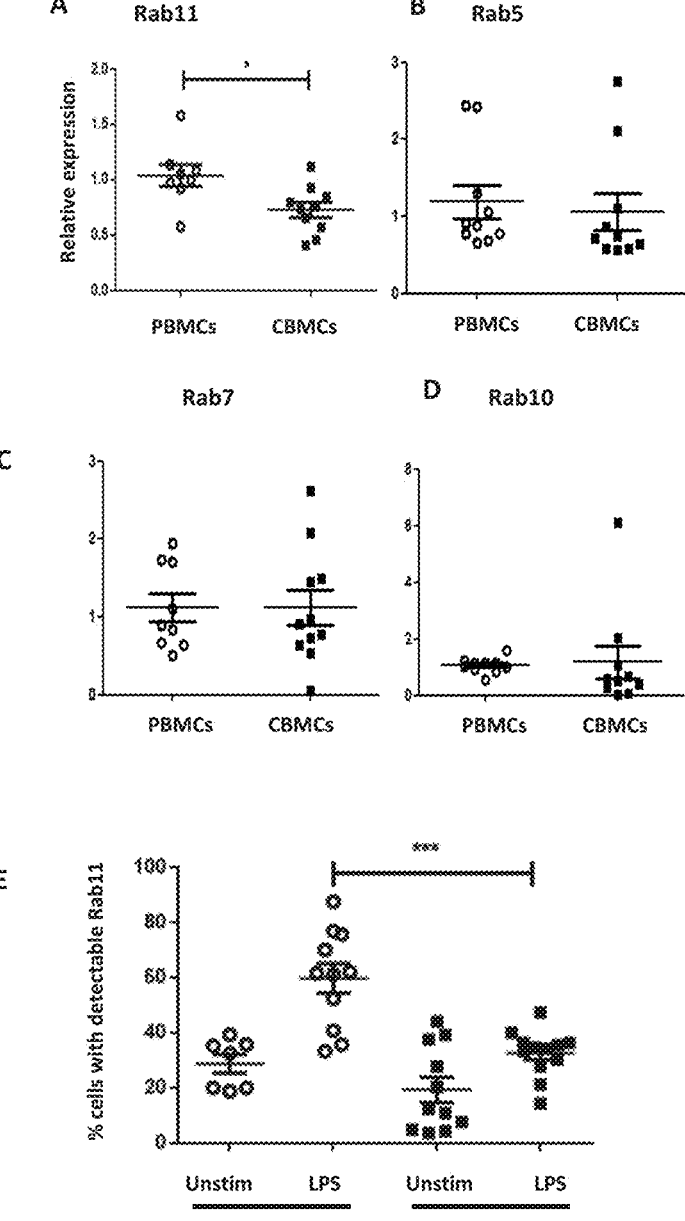
Figure 13:
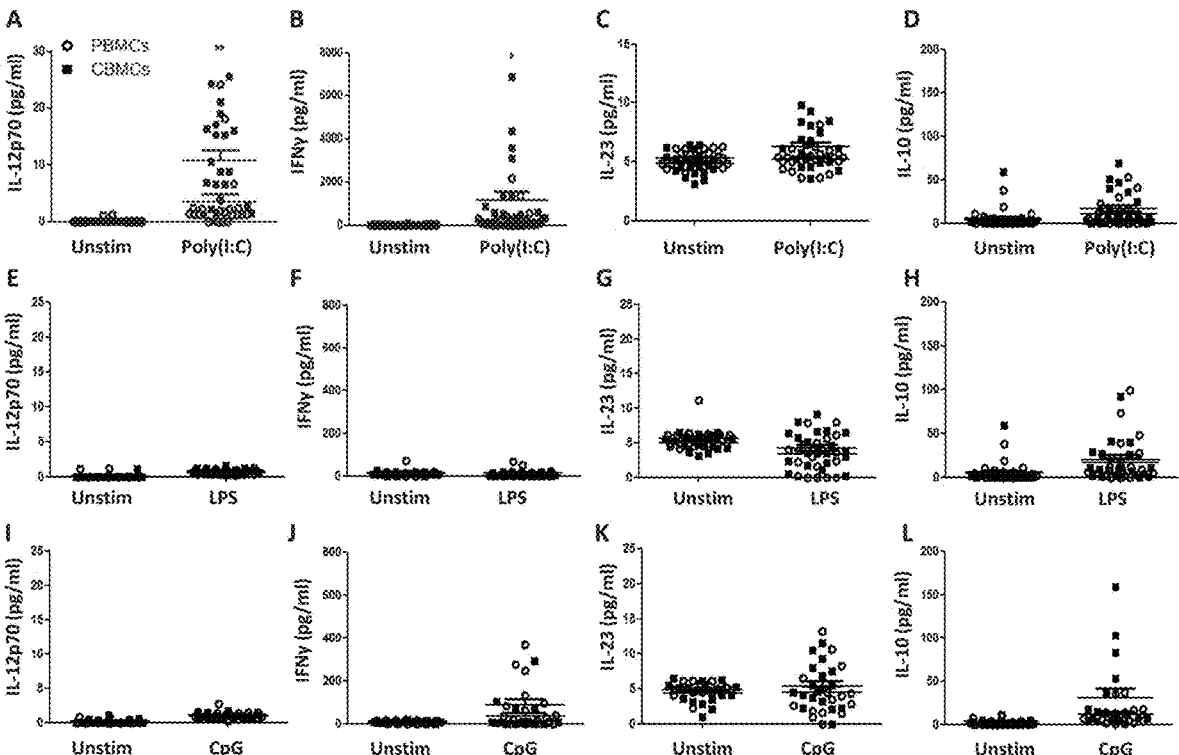

FIG. 12: Rab11 expression is decreased in response to TLR activation in neonatal cells, while Poly(I:C) induction of Th1 polarising IL-12p70 and IFNγ is increased in CBMCs compared to PBMCs.

Expression of (A) Rab11, (B) Rab5, (C) Rab7 or (D) Rab10 mRNA in PBMCs vs CBMCs was assayed by quantitative RT-PCR, normalized to β-actin and presented relative to adult PBMCs. (E) CD14 positive cells were isolated from adult PBMCs or neonatal CBMCs and left unstimulated or treated with 1 μg/ml LPS for 1 h. Cells were stained for Rab11 expression and DAPI. Cells expressing detectable levels of Rab11 were counted and presented as a percentage of total cells (using >200 cells).

FIG. 13(A)-(L): PBMCs or CBMCs were transfected with (A-D) Poly(I:C) for 24 h, treated with (E-H) LPS for 4 h or (I-L) CpG ODN for 24 h and BioLegend LEGENDplex™ Human Inflammation Panels were used to measure the levels of (A, E, I) IL-12p70, (, F, J) IFN-γ, (C, G, K) IL-23 and (D, H, L) IL-10. *P<0.05, P<0.01, *P 21 0.005. P-value was determined by unpaired Student's t-test (A)-(D) or Analysis of variance (ANOVA) and Bonferroni's post-test (E).

(F)-(Q) Kruskal-Wallis non-parametric test with Dunn's post-test was used to test for significant differences between groups.

Figure 14:
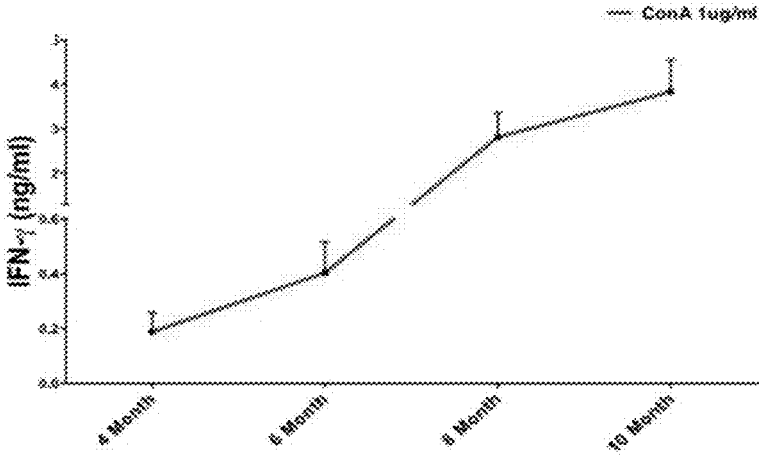

FIG. 14: ConA stimulated PBMCs from neonatal calves secrete low concentrations of IFN-γ. PBMCs from calves aged 4-10 months were incubated with 1 μg/ml of ConA at 37° C. in T cell media for 72 hours. Supernatants were collected and tested for IFN-γ.

Figure 15:
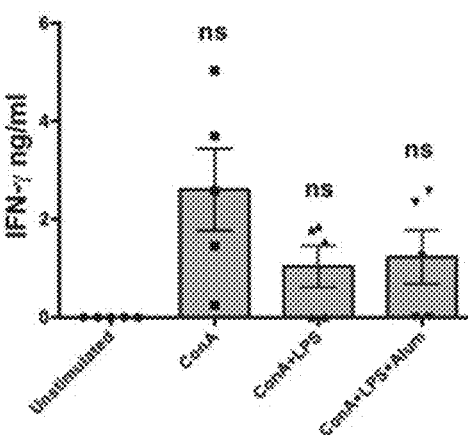

FIG. 15: Alum fails to enhance IFN-γ in ConA stimulated PBMCs. PBMCs from calves aged 8-10 months were incubated with 1 μg/ml of ConA alone or in addition to 100 pg/ml of LPS with or without 50 μg/ml of alum. The cells were incubated at 37° C. for 72 hours after which time supernatants were collected and tested for IFN-γ.

Figure 16:
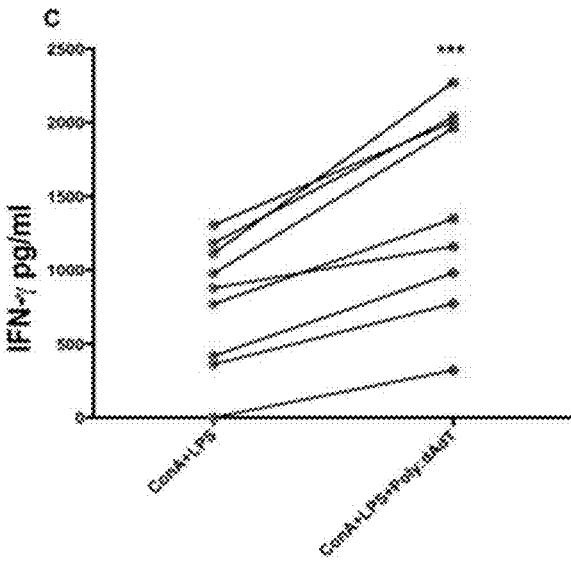

FIG. 16: Bovine IFN-γ secretion is increased in response to polydA:dT. PBMCs from 9 calves aged <1 year old were incubated with 1 μg/ml of ConA and 100 pg/ml LPS alone or in addition to 1 μg/ml of polydA:dT. The cells were incubated at 37° C. for 72 hours and supernatants were tested for the presence of IFN-γ.

Figure 17:
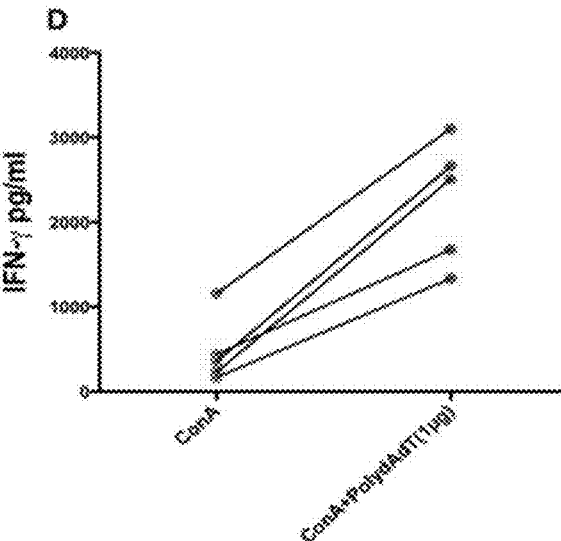

FIG. 17: PolydA:dT drives enhanced IFN-γ secretion in calves aged <1 year old. PBMCs from 5 calves aged 2 months were incubated with 1 μpg/ml of ConA alone or in addition to 1 μg/ml of polydA:dT. The cells were incubated at 37° C. for 72 hours and supernatants were tested for IFN-γ

Figure 18:
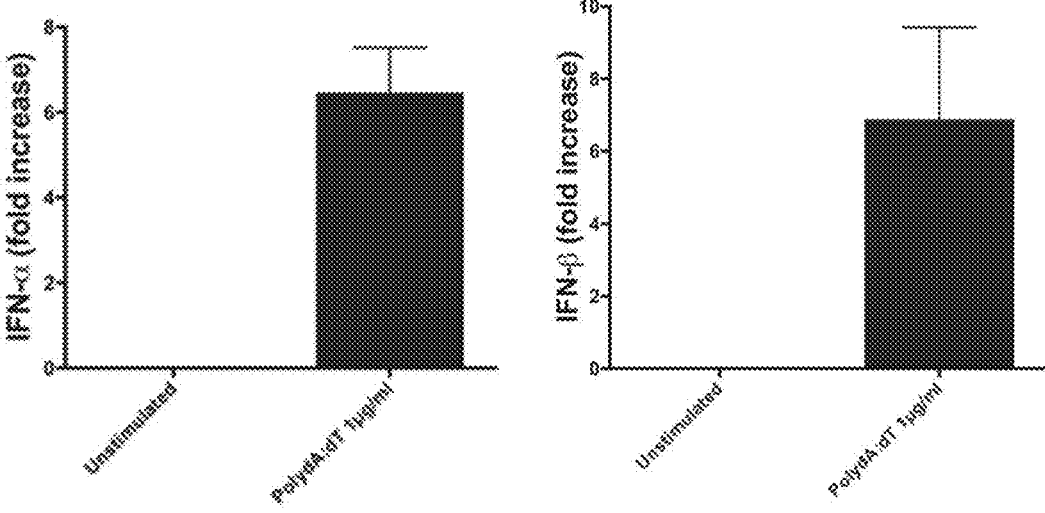

FIG. 18: PolydA:dT increases type I IFN expression by bovine PBMCs. PBMCs from calves aged 8-10 months were incubated with 1 μg/ml of polydA:dT or media as a control. The cells were incubated at 37° C. for 6 hours. The cells were then lysed and RNA was acquired for real-time PCR analysis. Primers specific for IFN-α and IFNβ were used.

Figure 19:
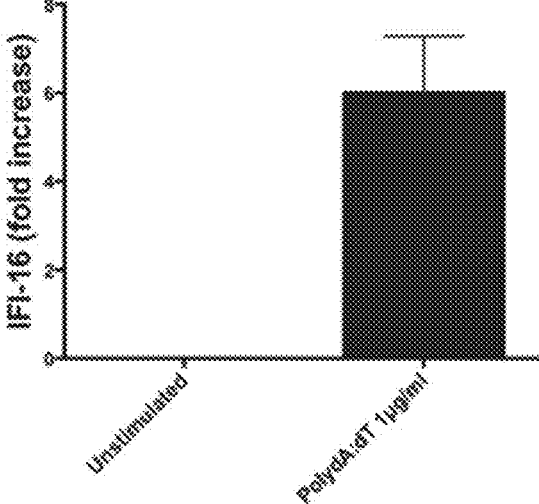

FIG. 19: IFI-16 expression in bovine PBMCs is enhanced in response to polydA:dT. PolydA:dT (1 μg/ml) was transfected into bovine PBMCs which were incubated for 12 hours. The cells were then lysed and RNA was acquired for real-time PCR analysis.

Figure 20:
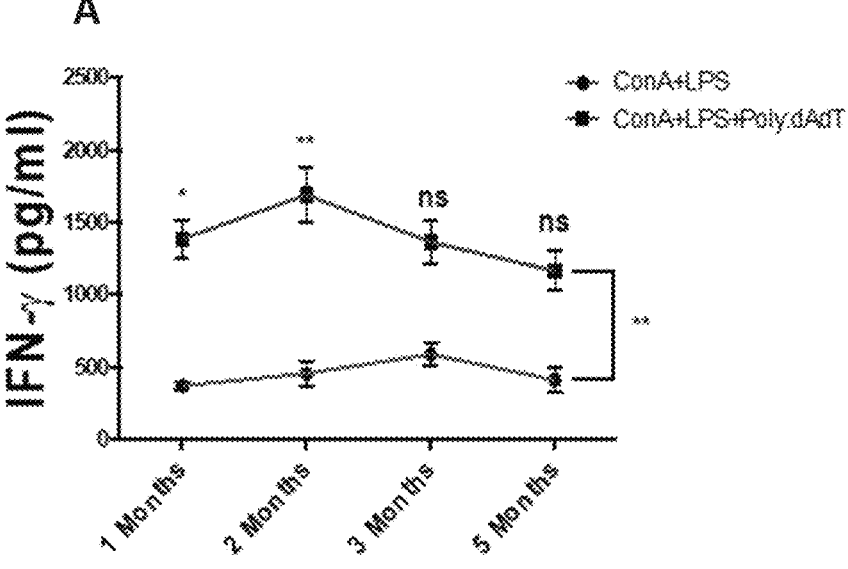
Figure 20:
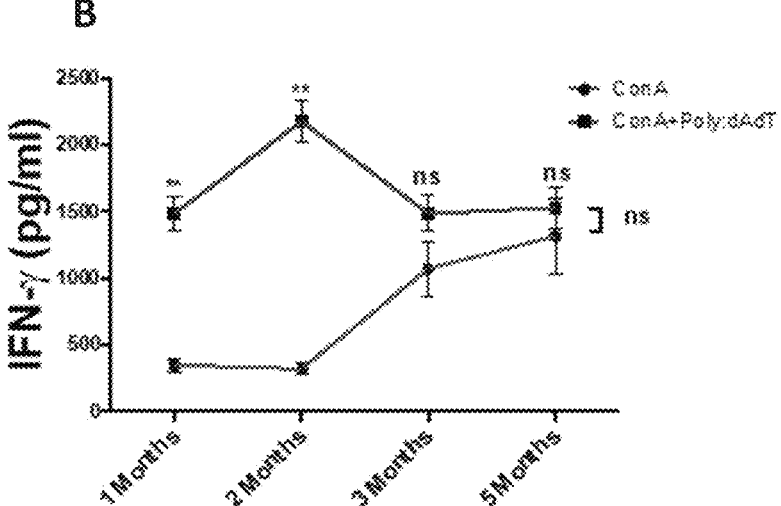

FIG. 20: PolydA:dT drives enhanced IFN-γ by cells from neonatal calves. PBMCs from the same 5 calves were isolated over a time course of 5 months beginning when the calves were aged 1 month old. The cells were stimulated with 1 μg/ml of ConA with (A) or without (B) 100 pg/ml LPS alone or in addition to 1 μg/ml of polydA:dT. Supernatants were harvested after 72 hours and IFN-γ was measured by ELISA.

Figure 21:
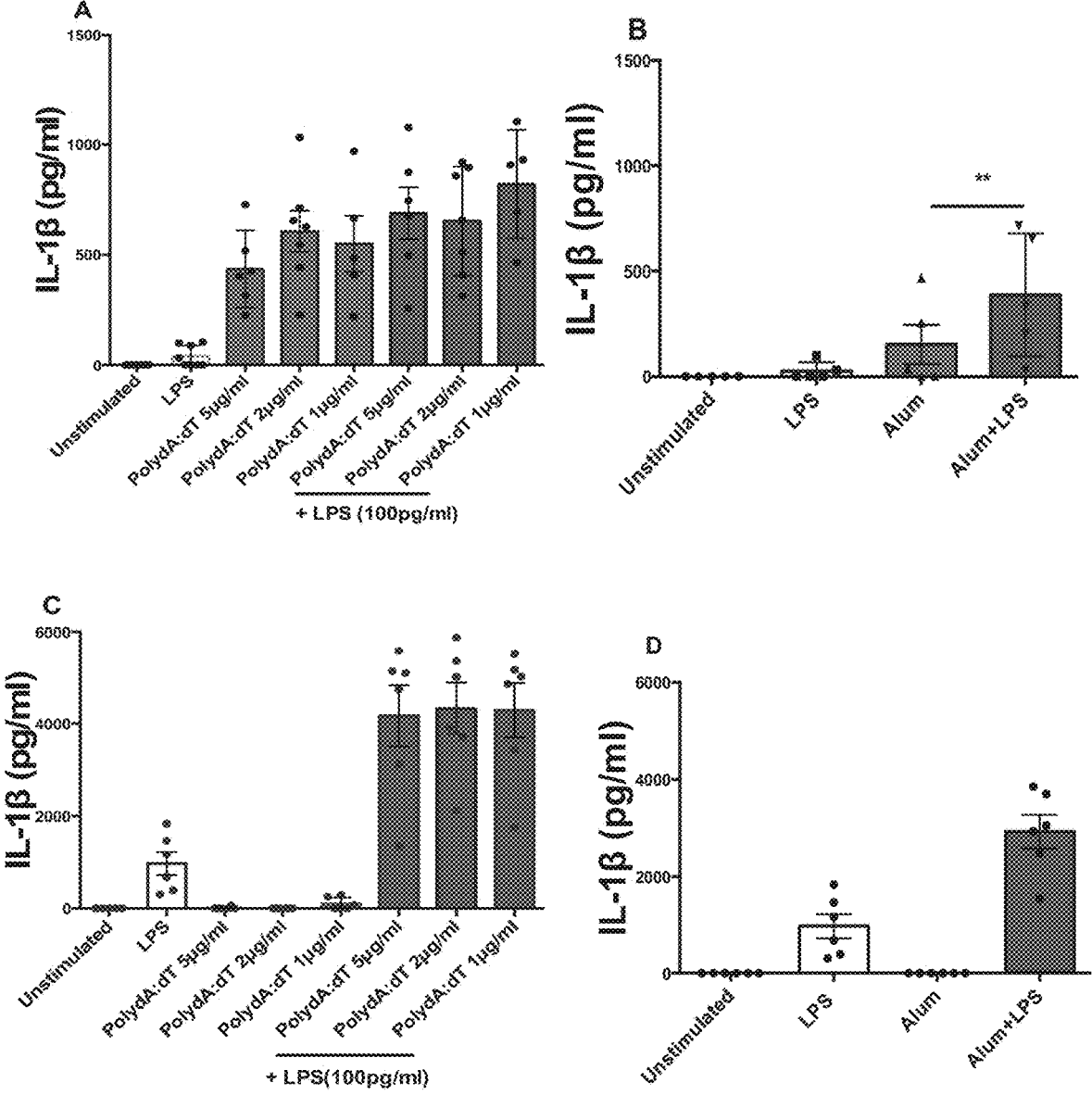
Figure 21:
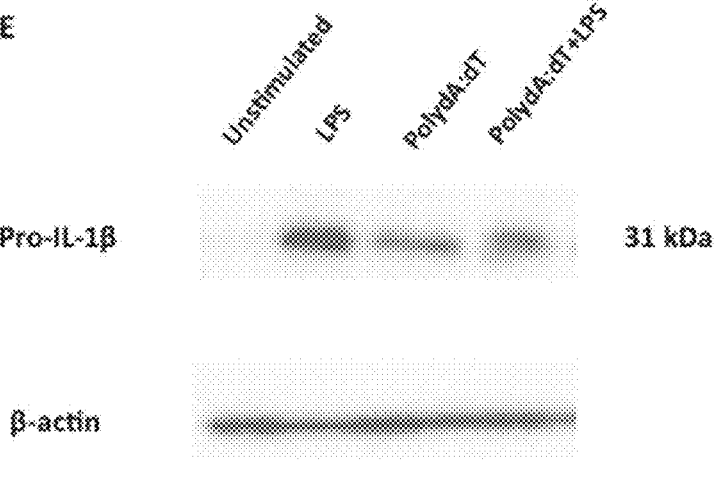
Figure 21:
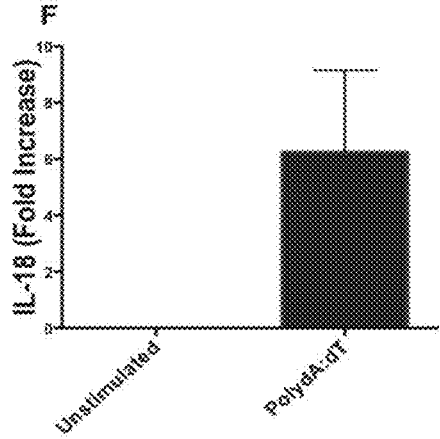

FIG. 21: Bovine IL-1β secretion and IL-18 expression is enhanced by polydA:dT: Bovine PBMCs were cultured for 24 hours with polydA:dT (5 μg/ml, 2 μg/ml or 1 μg/ml) or alum (50 μg/ml) in the presence or absence of LPS (100 pg/ml) (A & B). Supernatants were collected after 24 hours and IL-1β was detected by ELISA. Human PBMCs were stimulated for 24 hours with polydA:dT (5 μg/ml, 2 μg/ml or 1 μg/ml) or alum (50 μg/ml) alone or with LPS (100 pg/ml) (C & D). Supernatants were collected and IL-1β was detected by ELISA. Bovine PBMCs were cultured with polydA:dT (1 μg/ml) with or without LPS (100 pg/ml) for 16 hours (E). Cell lysates were harvested and pro-IL-1β was detected by western blot. PBMCs were stimulated with media or polydA:dT (1 μg/ml) for 6 hours. Cells were lysed and RNA was harvested and used for analysis by RT-PCR (F). Results are mean+/− SEM for 6 calves tested individually in triplicate. For human analysis, results are mean+/− SEM for 6 humans tested individually in triplicate The PPIA gene was used for normalization of gene expression.

Figure 22:
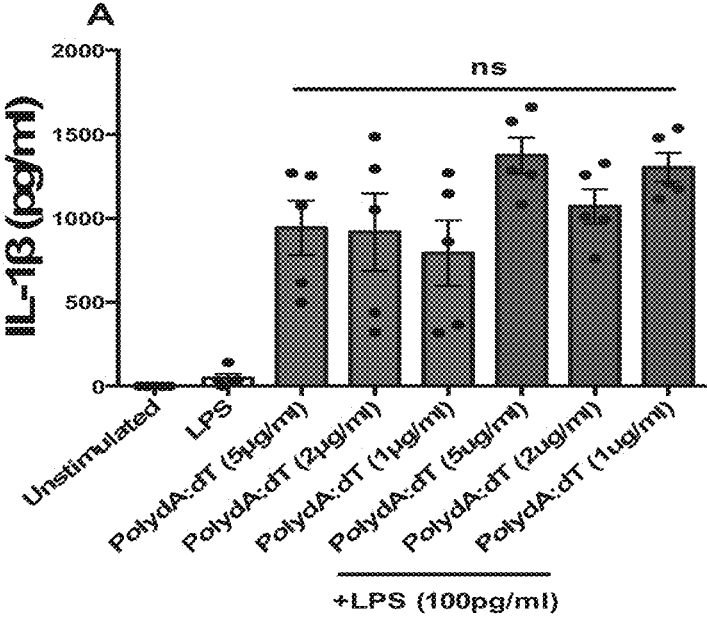
Figure 22:
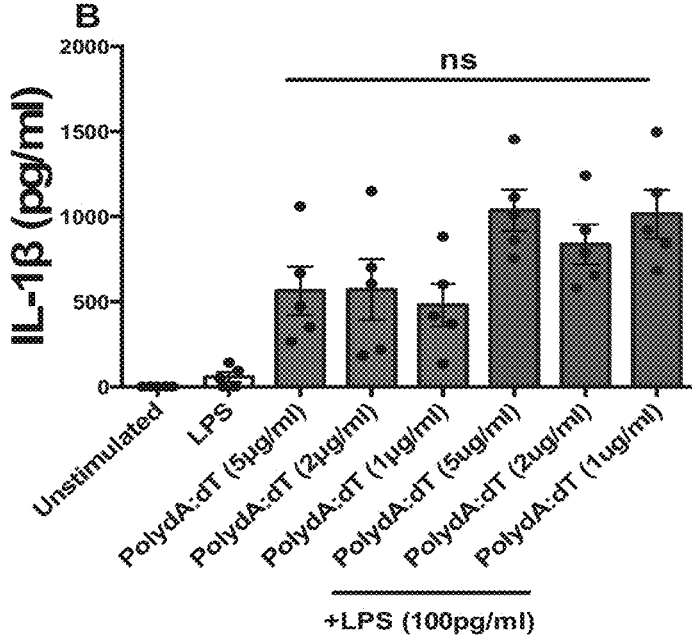
Figure 23:
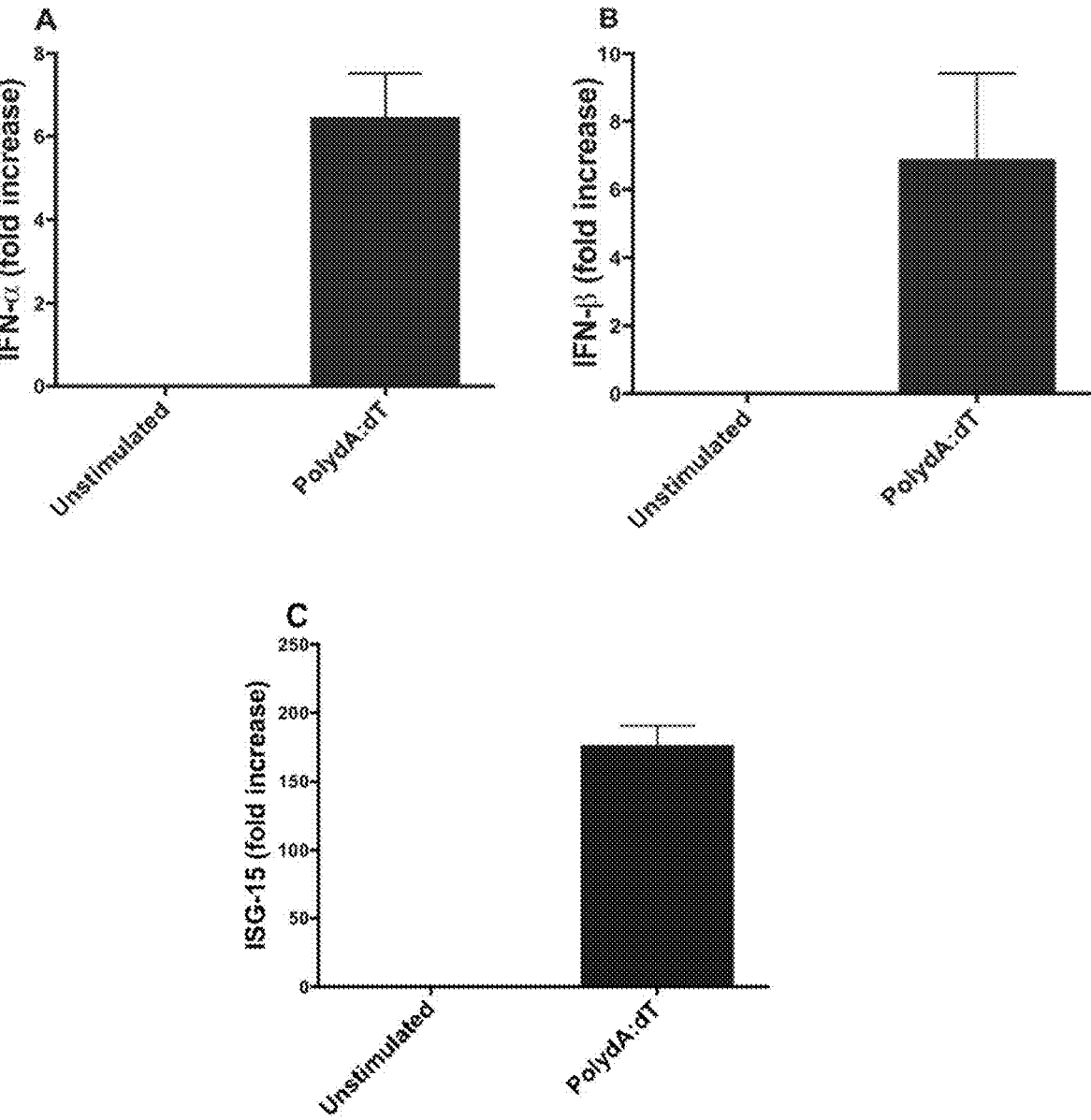

FIG. 22: PBMCs from neonatal cattle can secrete IL-1β in response to polydA:dT without LPS priming. PBMCs from 5 calves were primed with LPS or media 3 hours before polydA:dT stimulation (5 μg/ml, 2 μg/ml or 1 μg/ml). Supernatants were collected after 24 hours and IL-1β was measured by ELISA at 1 month (A) and 2 months (B) of age. Results are mean+/− SEM for 5 calves tested individually in triplicate FIG. 23: PolydA:dT enhanced IFN-α, IFN-β and ISG-15 expression by bovine PBMCs. PBMCs from Friesian calves aged 6-12 months were stimulated with polydA:dT (1 μg/ml) for 6 hours at 37° C. The cells were lysed and RNA was harvested for analysis by RT-PCR. Primers were designed and used to measure amplification of genes coding for IFN-α (A), IFN-β (B) and ISG-15 (C). The PPIA (Peptidylprolyl isomerase A) gene was used for normalization of gene expression. Error bars on graph indicate mean+/− SEM for 4 calves tested individually in duplicate.

Figure 24:
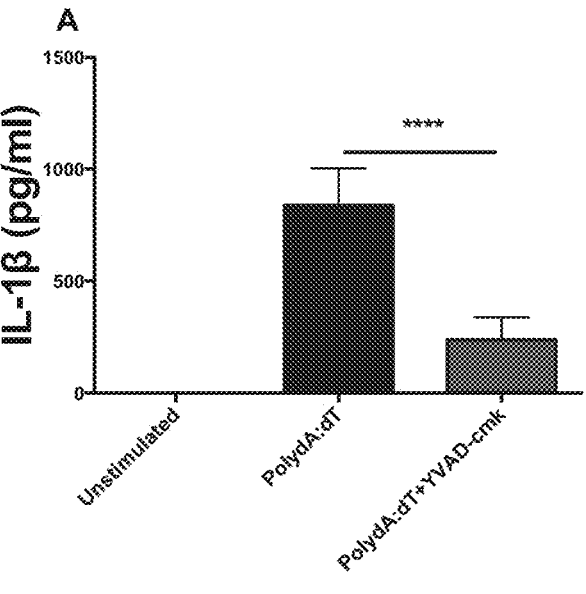
Figure 24:
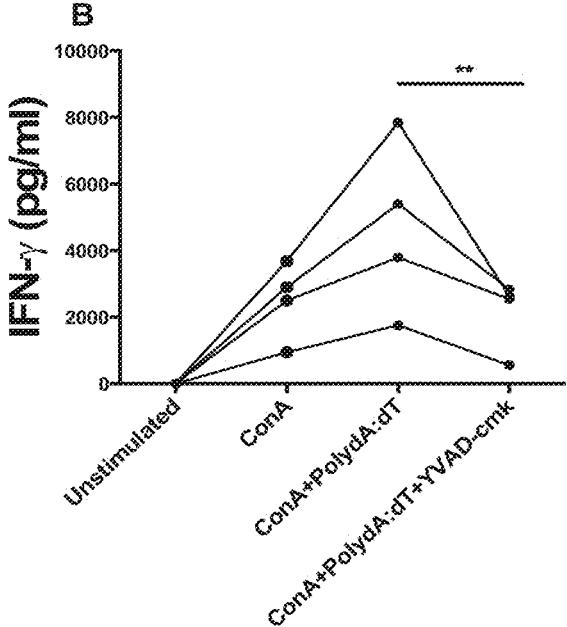

FIG. 24: Caspase-1 plays an important role in polydA:dT induced IL-1β and IFN-γ secretion. PBMCs from Friesian calves aged <6 months were stimulated with YVAD-cmk (10 μm/ml ) for 1 hour prior to stimulation with polydA:dT (1 μg/ml) for 24 hours (A). Supernatants were harvested and analysed for IL-1β by ELISA. Similarly, PBMCs from Friesian calves aged <6 months were incubated with YVAD-cmk (10 μm/ml) for 1 hour prior to stimulation with polydA:dT (1 μg/ml) and ConA (1 μg/ml) (B). Cells were incubated at 37° C. for 72 hours and IFN-γ was detected in supernatants by ELISA. Results are mean+/− SEM for 4 calves tested individually in triplicate. * p<0.05, p<0.01, *p<0.001 were calculated using an ANOVA test on GraphPad.

Figure 25:
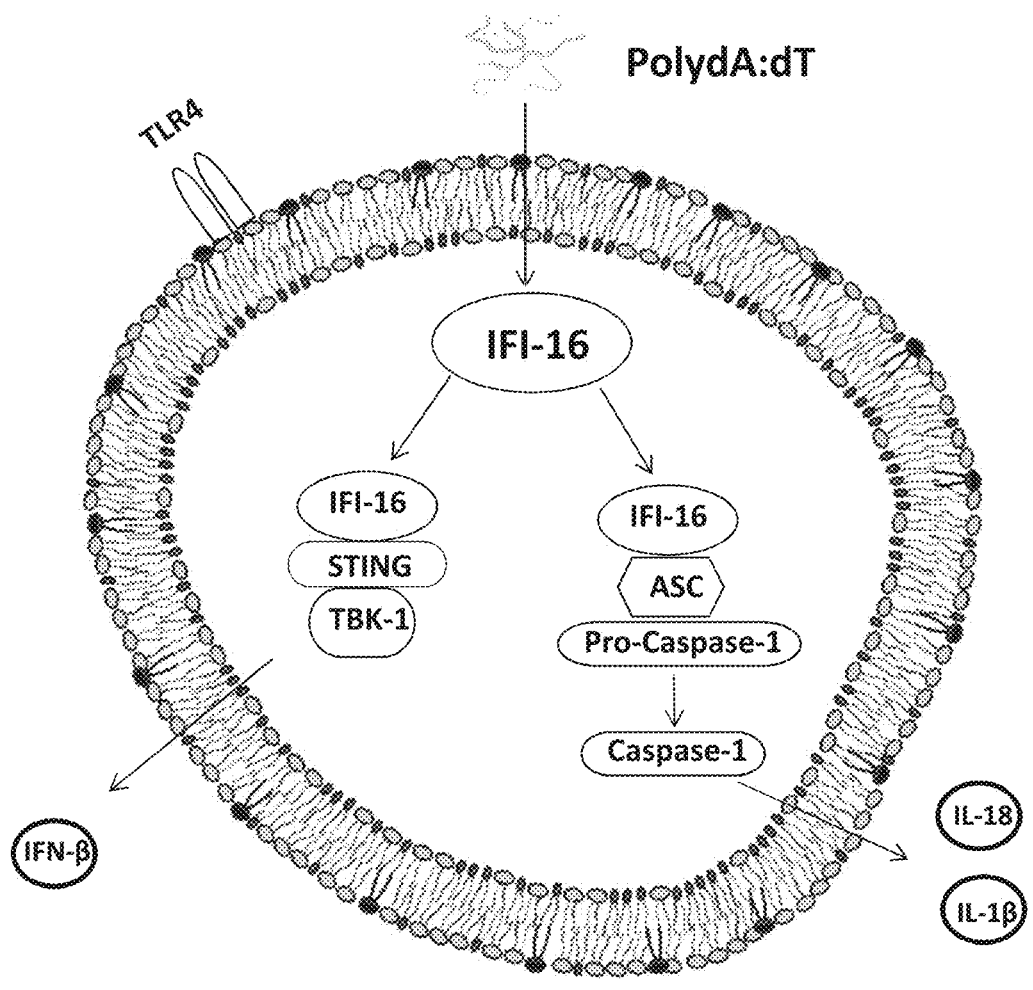

FIG. 25: is a schematic figure showing that polydA:dT drives innate cytokine secretion and expression. PolydA:dT mediates IL-1β secretion through caspase-1. PolydA:dT can also drive enhanced expression of inflammasome derived IL-18. Type I IFN expression is also increased in response to polydA:dT.

EXAMPLES 1 AND 2

1.0 Example 1

Materials

Umbilical cord blood samples were obtained from term births following normal pregnancy, labour and delivery at National Maternity Hospital (NMH), Holles St, Dublin 2. All infants had an uncomplicated postnatal course and Apgar scores of 9 at 5 minutes. Venous blood from infants, children and adolescents of various ages was collected during elective surgical procedures where no indication of infection was present (such as hydrocele repair, umbilical hernia repair, onychocryptosis, orchipexy repair) in Our Lady's Children's Hospital Crumlin (OLCHC), Dublin 12. In all cases children had an extra 1-10 ml of blood drawn post-anaesthetic, thus avoiding extra venupuncture. Volumes drawn were age and weight dependent, according to standard, approved guidelines. Ethics approval was obtained from the Ethics Committees of NMH and OLCHC and informed consent was obtained from each subject or their parent/guardian. Adult blood samples were from healthy adults, supplied by the Irish Blood Transfusion Service.

Poly(I:C), Poly(dA:dT) and cGAMP were obtained from Invivogen

Poly (dA:dT) is a repetitive synthetic double-stranded DNA sequence of poly(dA-dT)-poly(dT-dA) http://www.invivopen.com/poly-dadt-naked Poly (I:C) comprises long strands of inosine poly(I) homopolymer annealed to strands of cytidine poly(C) homopolymer http://www.invivogen.com/polyic-hmw.

cGAMP is cyclic [G(2',5')pA(3',5')p]; Formula: $C_{20}H_{22}N_{10}P_{13}P_2$, 2Na Methodology Isolation of mononuclear cells and monocytes—Primary PBMCs or CBMCs were isolated from healthy human blood or cord blood. Monocytes were isolated by negative selection using Monocyte Isolation Kit II (Miltenyi). Monocyte purity was assessed using CD14 staining and was routinely 85-95%. Cells were cultured at 37° C., 5% CO2, 95% air in RPMI-1640, with stable 2.5 mM L-glutamine and 0.5 mM sodium pyruvate with 10% FBS (all from Sigma-Aldrich).

Stimulation of PBMCs and CBMCs—LPS (lipopolysaccharide) (100 ng/ml) (Enzo), CL075 (5 μg/ml) and CpG ODN 2395 (synthetic oligodeoxynucleotides) (1 μM) (both from Invivogen) were used to activate TLR4, 8 and 9 respectively. Poly(I:C) (5 µg/ml) (Invivogen), Poly(dA:dT) (5 µg/ml) (Sigma-Aldrich), 2'3' cGAMP (10 µg/ml), 5' triphosphate double stranded RNA (5' ppp dsRNA) (2.5 µg/ml) and HSV-60 (2 µg/ml) (all from Invivogen) were transfected into PBMCs or CBMCs using TransIT-X2 (Mirus).

Measurement of cytokines—HEK Blue TNFα/IFNα/β Assays were performed as per the manufacturer's (Invivogen) instructions using Quanti-Blue Detection Reagent. SEAP levels were determined using a spectrophotometer plate reader at 630 nm. IFNα (3425-1H-6, Mabtech) and IP-10 (DY266, R&D Systems) were detected by sandwich ELISA. IFNα ELISA used pan specific IFNα antibodies, which allows detection of IFNα subtypes 1/13, 2, 4, 5, 6, 7, 8, 10, 14, 16 and 17. BioLegend LEGENDplex™ Human Inflammation Panel (13-plex) was carried out as per manufacturer's (Biolegend) instructions to determine levels of IFNγ, IL-10, IL-12p70 and IL-23. A BD LSR Fortessa cell analyser was used to acquire samples and BioLegend LEGENDplex™ software was used for analysis.

IRF3/7 activation—Active Motif TransAM™ IRF3 and IRF7 assays were carried out on nuclear extracts from PBMCs or CBMCs, harvested as per manufacturer's (Active Motif) instructions, to detect and quantify IRF3 or IRF7 activation.

Cell Viability—An LDH cytotoxicity assay kit (Pierce) was used to measure cell death in response to stimulation as per manufacturer's instructions. The absorbance was read at 490 nm and background (absorbance at 680 nm) was subtracted. A CellTiter 96®Aqueous Non-Radioactive Cell Proliferation Assay (MTS assay) (Promega) was also used to measure cell viability through assaying mitochondrial function, according to manufacturer's instructions. Absorbance was read at 490 nm on a 96 well plate spectrophotometer.

Quantitative RT-PCR—Total RNA from PBMCs or CBMCs was extracted using trizol extraction as previously described (16) and was reverse transcribed using MMLV Reverse Transcriptase (Promega) according to the manufacturer's protocol. This cDNA served as template for amplification of target genes, along with the 'housekeeping' gene βActin, by real-time PCR with SensiFast SYBR Green (Bioline) to determine the relative amounts of CXCL10, IFNα and TNFα mRNA. The ABI 7900HT system (Applied Biosystems) was used for real-time PCR, and the cycling threshold method ($2^{-(\Delta\Delta Ct)}$) was used for relative quantification by comparative method after normalization to βActin expression.

The primers used are outlined in Table 1 below.

TABLE 1

| Primer sequences | |
| --- | --- |
| CXCL10 | |
| forward | 5'-AGCAGAGGAACCTCCAGTCT-3';<br>(SEQ ID No. 9) |
| reverse | 5'-ATGCAGGTACAGCGTACAGT-3';<br>(SEQ ID No. 10) |
| IFNα | |
| forward | 5'-TGAAGGACAGACATGACTTTGG-3';<br>(SEQ ID No.11) |
| reverse | 5'-TCCTTTGTGCTGAAGAGATTGA-3';<br>(SEQ ID No. 12) |

20

TABLE 1-continued

| Primer sequences | |
| --- | --- |
| Rab5 | |
| forward | 5'-ACGGGCCAAATACGGGAAAT-3',<br>(SEQ ID No. 13) |
| reverse | 5'-AGAAAAGCAGCCCCAATGGT-3';<br>(SEQ ID No. 14) |
| Rab7 | |
| forward | 5'-CAGACAAGTGGCCACAAAGC-3',<br>(SEQ ID No. 15) |
| reverse | 5'-AAGTGCATTCCGTGCAATCG-3'<br>(SEQ ID No. 16) |
| Rab10 | |
| forward | 5'-CCTCAGAAAGCCCGAGTGAG-3',<br>(SEQ ID No. 17) |
| reverse | 5'-GTCGTACGTCTTCTTCGCCA-3';<br>(SEQ ID No. 18) |
| Rab11 | |
| forward | 5'-CTTCGGCCCTAGACTCTACA-3',<br>(SEQ ID No. 19) |
| reverse | 5'-CACTGCACCTTTGGCTTGTT-3'<br>(SEQ ID No. 20) |
| TNFα | |
| forward | 5'-CTGGGCAGGTCTACTTTGGG-3',<br>(SEQ ID No. 21) |
| reverse | 5'-CTGGAGGCCCCAGTTTGAAT-3'.<br>(SEQ ID No. 22) |

IFNα primers were designed to detect IFNα subtypes 2, 5, 6, 8, 14, 16, 17 and 21.

Flow cytometry—PBMCs or CBMCs were labelled for the investigation of DC or monocyte subsets with the following fluorochrome-labelled antibodies: CD45 (2D1), CD16 (3G8), CD14 (M5E2), CD66b (G10F5), CD11c (3.9), Lineage (CD3, CD14, CD16, CD19, CD20, CD56), HLA-DR (L243) and CD123 (6H6) (All from Biolegend). Each staining well contained $4 \times 10^5$ cells, cells were stained with LIVE/DEAD™ Aqua (Molecular Probes), followed by staining for 20 m on ice, washed and analysed by flow cytometry immediately. Gating during analysis was based on FMO controls. For transfection efficiency investigation, PBMCs or CBMCs were transfected with Poly(I:C) Fluorescein (5 µg/ml) (Invivogen) for 24 h and analysed for percentage fluorescein expression as a measure of transfection efficiency. Flow cytometry was carried out on a BD LSR Fortessa cell analyser and analysed using FlowJo software (TreeStar).

Confocal imaging—CD14⁺ monocytes, negatively selected from PBMCs or CBMCs, were seeded on Nunc® Lab-Tek® II Chamber Slide™ system. LPS was sonicated for 30 s and pre-incubated in serum-containing medium at 37° C. for 5 m before being added to cells. Cells were stimulated with LPS (1 µg/ml) for 1 h. Cells were fixed in 2% PFA, permeabilised in 0.05% Triton X-100, stained with goat anti-human Rab11 (K-15) (Santa Cruz) at 10 µg/ml and anti-goat AlexaFluor647 at 4 µg/ml or for co-staining, rabbit anti-human Rab11 (ab3612) and mouse anti-human TLR4 (ab22048), and anti-rabbit AlexaFluor 488 and anti-mouse AlexaFluor 647. Cells were mounted using ProLong® Gold Antifade Mountant with DAPI. Images were captured using an Axio Observer Z1 inverted microscope equipped with a Zeiss LSM 700 T-PMT scanning unit and a 40× plan apochromat objective. Image analysis was carried out using LSM ImageBrowser.

Statistical analyses—Data was analysed with GraphPad Prism software. Normality testing was carried out using Shapir-Wilk, Kolmogorov-Smirnov, and D'Agostino & Pearson omnibus normality testing. When datasets were found to follow a non-normal distribution a Kruskal-Wallis with Dunn's multiple comparison test or Mann Whitney U test was carried out. Statistical analysis on normal datasets was performed with Student's t-test, when two individual experimental groups were analysed. For multiple comparisons, ANOVA was used with a Bonferroni post-test. Two-tailed tests were used throughout, and the statistical approaches were all deemed to be valid for each individual experiment.

Results

Figure 1:
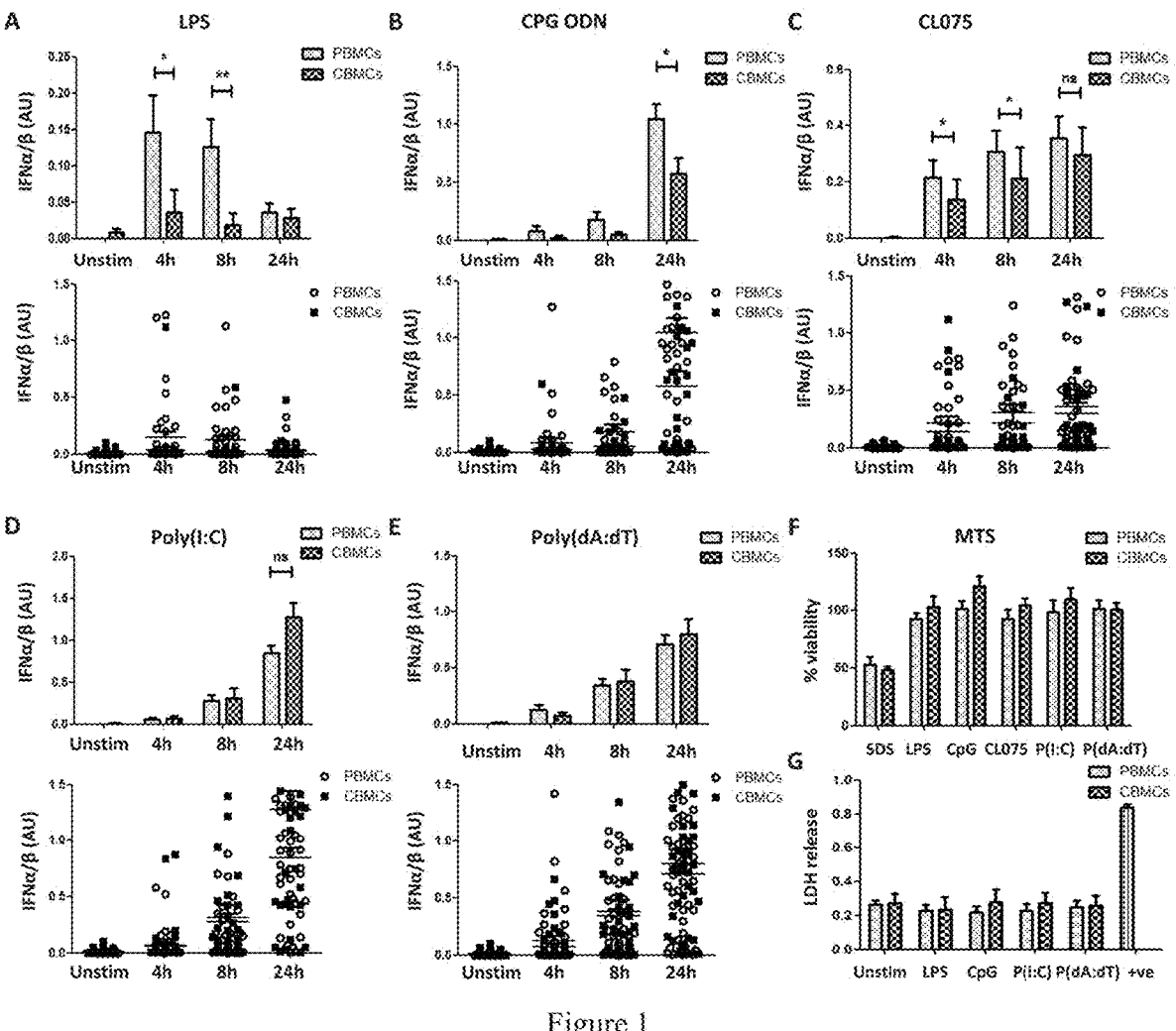
FIG. 1: Differential regulation of neonatal IFNα/β secretion between membrane bound TLRs and cytosolic nucleic acid sensors.

Previous studies have reported that LPS- and CpG-induced type I IFN production is decreased in neonatal cells in comparison to adult cells. Using HEK-Blue-IFNα/β reporter cells we confirmed this observation in PBMCs and CBMCs (n≥30) (FIG. 1A, B). CL075, a TLR7/8 agonist also induced significantly lower levels of IFNα/β production from CBMCs compared with PBMCs (n=35) albeit in a less marked manner (FIG. 1C). In contrast, mimicking viral infection through activation of cytosolic RLRs/dsDNA sensors with transfected Poly(I:C) and Poly(dA:dT), showed no inhibition of type I IFN production in CBMCs when compared to PBMCs (n≥39) (FIG. 1D, E). Transfection only controls were also carried out (FIG. 9A). Untransfected Poly(I:C), as a TLR3 agonist, was also used to stimulate PBMCs and CBMCs or isolated monocytes from adult and cord blood, and as expected from the literature, type I IFN responses were decreased in neonatal cells (FIGS. 9B & 9C). MTS and lactate dehydrogenase (LDH) assays were performed on stimulated PBMCs and CBMCs to assess whether cell death occurred in either cell type in response to TLR, RLR or dsDNA sensor ligation that might skew the results, however, no differences were observed between cell types (FIG. 1F, G). Dot plots for MTS and LDH assays are shown in FIGS. 9D & E.

In order to ensure we were comparing like with like, we assessed the sub-populations of mononuclear cells in our neonatal cord blood mononuclear cell preparations and our adult mononuclear cell preparations. Leukocyte percentages in PBMCs and CBMCs were measured via flow cytometry and based on CD45+ staining, no significant difference in leukocyte percentage frequency was found between adult and neonatal mononuclear cells (FIG. 2A). Dendritic cell (DC) populations were also measured, as plasmacytoid DCs (pDCs) are excellent producers of Type I IFN. Lineage-HLA-DR+ DC cells were analysed for expression of CD123 and CD11c, markers of pDCs and conventional DCs (cDCs), respectively. No significant difference in the populations of either pDCs or cDCs that might account for differences in cytokine production was observed when comparing adult and neonatal cells (FIG. 2B). Potential differences in monocyte populations between adult and cord blood were also investigated. Total monocytes were characterised as CD66b-CD14+CD11c+ and, based on their expression of CD16 and level of expression of CD14 were further characterised as classical (CD14+CD16-), patrolling (CD14intermediateCD16+) or inflammatory (CD14+CD16+) monocytes. No significant differences in any of these monocytes populations was observed when comparing mononuclear cells isolated from adult and cord blood (FIG. 2C). We next investigated whether there was any differential transfection efficiency between neonatal and adult mononuclear cells. Fluorescein-labelled Poly(I:C) was transfected into cells and fluorescein uptake was measured via flow cytometry. No significant difference was noticed in transfection efficiency of adult versus neonatal cells (FIG. 2D). Monocytes were isolated through negative selection from PBMCs or CBMCS to a purity of >85%. As observed in FIG. 2E, monocytes showed similar trends of IFN production as those observed from total adult and neonatal mixed mononuclear cell populations. Dotplots are shown in FIG. 10. We were unable to isolate sufficient numbers of pDCs from our preparations to check pDC responses by ELISA and flow cytometric analysis of type I IFN was unfeasible. Our data indicated that differences observed between neonatal and adult responses to ligands of TLRs and similarities observed between neonatal and adult responses to ligands of CNA sensors were a result of differences in intracellular signalling pathways and not due to alterations in cell population, viability or transfection efficiency.

Next, we performed IFNα ELISAs on cells supernatants from adult or neonatal mononuclear cells treated with LPS, CpG ODN, transfected Poly(I:C) or transfected Poly(dA:dT) (n≥23). Similar trends and significant differences were seen for the IFNα ELISA as had been observed in the IFNα/β SEAP assays, with significantly decreased TLR4/9-induced IFNα responses but equivalent or enhanced CNA sensor responses in neonates compared to adults (FIG. 3A-D). Alternative preparations of nucleic acid, eg. 5' ppp dsRNA and HSV60 are suggested to specifically activate RIG-I and IFI16 respectively, similarly 2'3' cGAMP is the direct ligand for STING. These agonists were tested for their ability to induce IFNα from adult and neonatal cells (n≥18). In all cases the levels of IFNα produced in response to these ligands was lower than that in response to either Poly(I:C) or Poly(dA:dT), nevertheless CBMCs responded equally well or with enhanced IFNα-production when compared with PBMCs (FIG. 3E-G). To ensure that this increase in neonatal IFNα production was not linked to an increase in cell death, cell viability was assayed via MTS assay in cells treated with CNA agonists and compared to unstimulated controls. No difference in cell viability was observed between PBMCs and CBMCs, following nucleic acid stimulation (FIG. 3H).

IFNα is an antiviral cytokine particularly relevant for host defence against intracellular pathogens as it promotes a Th1 type immune response. TNFα also promotes a Th1-type response. TNFα has previously been studied in the neonatal setting in response to TLR agonists but not in response to CNA sensors. Following our novel observation that CNA induced an increase in production of IFNα in neonatal compared to adult mononuclear cells, TNFα production in response to CNA was investigated in more detail. TNFα was measured in supernatant of PBMCs and CBMCs treated with Poly(I:C)-, Poly(dA:dT)-, dsRNA-, cGAMP-, HSV60-transfection, LPS, CL075 or CPG ODN for 4, 8 or 24 hours (n≥29). Interestingly, all CNAs tested induced significantly more TNFα production from neonatal cells than from adult cells (FIG. 4A-E). In contrast, no significant difference in TNFα production was observed from CBMCs and PBMCs treated with TLR agonists LPS or CL075 (FIG. 4F, G). CpG ODN did not induce any production of TNFα from either PBMCs or CBMCs (FIG. 4H).

Thus far, we had observed differential regulation of IFNα that was broadly delineated between responses to cytosolic receptors versus responses to membrane-bound receptors, with type I IFN responses intact or enhanced in neonates in response to CNA but attenuated in response to TLR-4/7/8/9 activation. The ability of neonatal cells to induce equal levels of TNFα as adult PBMCs in response to TLR activation (FIG. 4F, G) indicated that cell signalling from these receptors to NFκB is fully intact. Furthermore, the ability of neonatal cells to secrete IFNα in response to CNA indicates the process of type I IFN secretion is not affected. The implication is that factors specific for the signalling pathway to IFNα/13-induction downstream of TLRs (but not CNA sensors) are inhibited in some manner. To verify this, real-time qPCR was used to measure levels of mRNA expression of TNFα, IFNα and CXCL10 in response to Poly(I:C), Poly(dA:dT), LPS or CpG ODN (n≥4). There was no significant difference in TNFα levels in response to either CNA transfection or LPS stimulation between PBMCs or CBMCs (FIG. 5A, dotplots shown in FIG. 11A). In contrast, gene expression levels of IFNα and CXCL10, an IFN-inducible gene, were inhibited in CBMCs in response to CpG and LPS respectively when compared to the PBMC response. Whereas, there was no inhibition of transcription of either IFNα or CXCL10 in CBMCs in response to CNA stimulation (FIG. 5B, C & FIG. 11B, C). Together, this data indicates the TLR-induced signalling pathway to IFN gene expression is inhibited in a manner that does not affect the signal transduction pathway utilized by CNA sensors to induce gene expression of IFN.

IRFs-3 and -7 are implicated as transcription factors activated downstream of PRR ligation to induce type I IFN. IRF7 in particular is thought to be important for the induction of IFNαWe hypothesised that IRF7 activation would be enhanced in CBMCs in response to Poly(I:C) transfection when compared to IRF7 activated by TLR4 or TLR9 ligation. Intriguingly we found that IRF7 was not significantly activated by LPS, CpG or Poly(I:C) transfection in the CBMCs (n=4), by striking contrast LPS, CpG and Poly(I:C) all activated IRF7 in adult PBMCs (n=5), with percentage increases in activation over basal IRF7 between 150%-250% (FIG. 5D, & FIG. 11D). Aksoy et al (2007) Interferon regulatory factor 3-dependent responses to lipopolysaccharide are selectively blunted in cord blood cells. Blood 109, 2887-2893 have previously shown that impaired IRF-3 DNA binding and CBP interaction in neonatal DCs exposed to LPS is associated with impaired expression of IFNβ and IFN-inducible genes. As mentioned, both IRF3 and IRF7 are implicated as transcription factors for both IFNα and IFNβ, we next investigated whether in contrast to LPS-induced impaired IRF3 activation in neonates, Poly(I:C)-transfection might promote activation of IRF3 DNA binding. We observed an approximate 20% increase in IRF3 activation above basal levels in response to either LPS or CpG stimulation in CBMCs, indicating significant, but low levels of IRF3 activation (n=4). On the other hand, Poly(I:C) transfection resulted in ~80% increase in IRF3 activation above basal levels in CBMCs (n=4) (FIG. 5E & FIG. 11E).

Together these results indicate that IRF7, although expressed, may not be activated in neonates and that the signalling pathway to activate IRF3 to induce IFNα transcription is muted in CBMCs in response to LPS and CpG when compared to the efficient response to CNA. In support of this observation, we assessed the production of CXCL10 from PBMCs and CBMCs in response to CNA transfection or LPS stimulation (n≥29). There was no significant difference in the CXCL10 response between PBMCs or CBMCs to either Poly(I:C) or Poly(dA:dT) transfection (FIG. 5F, G & FIG. 11F, G), however LPS-induced CXCL10 secretion was significantly decreased in CBMCs compared to PBMCs (FIG. 5H & FIG. 11H). This observation highlights that induction of IFNα transcription and the subsequent IFN-response appears fully functional downstream of CNA transfection in CBMCs, in direct contrast to TLR stimulation of CBMCs where transcription of IFNα appears to be significantly inhibited with consequent subduing of the IFN-response.

A key difference between TLR-induction of IFNα/β and CNA-induction of IFNα/β is TLR-dependence on endosomal localisation to engage with TRAF3 and the IRFs. Several Rab GTPases have been reported to be involved in trafficking TLRs to endosomes. Of particular interest, in the absence of Rab11a, IFNα/β production in response to E. coli is significantly decreased whereas TNFα induction is unchanged. Therefore, we investigated the expression and function of Rab11a in PBMCs versus CBMCs. Realtime qPCR was used to investigate basal levels of Rab GTPase mRNA in PBMCs and CBMCs. Rab11a levels were found to be significantly lower in CBMCs compared to PBMCs (FIG. 6A) Strikingly, Rab11a was the only Rab GTPase with an expression profile that was significantly different between CBMCs and PBMCs, Rab5, Rab7 and Rab10 all showed comparable mRNA expression between CBMCs and PBMCs (n≥19) (FIG. 6B-D & FIG. 12B-D). We next investigated if Rab11+ve endosome formation was impaired in neonatal monocytes when compared to adult monocytes. CD14+ve monocytes were isolated from CBMCs and PBMCs (n=3). Adult monocytes showed abundant accumulation of Rab11+ve endosomes in response to LPS stimulation (FIG. 6E, upper panels). Rab11+ve endosomes were not observed to the same extent in neonatal monocytes in response to LPS (FIG. 6E, lower panels). FIG. 6F (& FIG. 12E) depicts the significant difference between the percentage of adult and neonatal cells with detectable Rab11 following LPS treatment. There is a clear inhibition of Rab11+ve endosome formation in neonatal monocytes in response to LPS stimulation when compared with adult monocytes (p=0.00011). To further support our findings, we investigated whether LPS induced TLR4 co-localisation with Rab11a would be less evident in neonatal monocytes. Accumulation of Rab11+ve endosomes in response to LPS stimulation was observed in adult monocytes, with co-localisation with TLR4 indicated by white arrowheads (FIG. 6G, left hand side panels). Again, Rab11+ve endosomes were difficult to observe in neonatal monocytes in response to LPS and are indicated by red arrow heads and did not appear to colocalise with TLR4 (FIG. 6G, right hand side panels). Given the literature on the reliance of LPS-induced type I IFN on Rab11a it seems likely that this is one mechanism by which neonatal cells constrain the immune response to gram negative bacteria.

In order to assess if CNA-induced IFNα and TNFα was a peculiarity of neonatal cord blood or whether these responses were maintained into infancy and early childhood, blood samples from healthy children in various age groups (4-24 months; 2-5 years; 6-11 years) undergoing elective surgery were collected and assayed for their ability to produce both type I IFN (n≥17) and TNFα (n≥16). As can be seen in FIGS. 7A & B, the production of type I IFN in response to Poly(I:C) and Poly(dA:dT) was maintained throughout childhood. This maintenance of cord blood responsiveness to CNA was also observed for both Poly(I:C) and Poly(dA:dT)-induced TNFα production to the age of 24 months (FIG. 7C, D).

Given the potential of Poly(I:C) transfection to induce substantial IFNα and TNFα production in neonates and infants and consequently give rise to a Th1-type immune response, desirable in vaccine-induced adaptive immunity, we sought to explore the polarising ability of Poly(I:C) transfection on IL-12p70, an important mediator of such responses (n=21)(27-31). IL-12p70 levels were low, as expected in a mixed population of cells, however, despite this, a similar significantly enhanced response to Poly(I:C) transfection was found in CBMCs compared to PBMCs (FIG. 8A). IL-12p70 was measured in a multiplex assay which included the analyte IFNγIFNγ is the primary cytokine that defines Th1 cells and is produced predominantly by CD4+ Th1 and CD8+ cytotoxic T cells creating a positive feedback loop causing naive CD4+ cells to differentiate into Th1 cells. To our great surprise, Poly(I:C)-transfection induced striking levels of IFNγ which was also significantly increased in CBMCs compared to PBMCs (FIG. 8B), despite the lack of a T cell activator (eg. anti-CD3). IFNγ is secreted at low concentrations by macrophages, NK and NKT cells as part of the innate immune response, is an important activator of both macrophages and NK cells and induces expression of major histocompatibility complex (MHC) class I and II (33). Levels of Th17-supporting cytokine IL-23 and anti-inflammatory IL-10 production were low but detectable, with no significant difference between adult and cord blood cells noted (FIG. 8C, D). The source of the observed IFNγ secreted by CBMCs in response to Poly(I:C) transfection remains to be identified in future experiments, however the high levels of IFNγ and enhanced IL-12p70 secretion implies that the environment created through activation of CNA sensors, in a mixed blood cell population, would be tailored towards promoting a Th1-mediated cellular immune response. In order to determine whether Poly(I:C) transfection might present a better adjuvant option for paediatric vaccine design than LPS and CpG analogues currently in use or in development, IL-12p70, IFNγ, IL-10 and IL-23 were also measured in CBMCs in response to LPS (n=20) or CpG (n≥16). In direct contrast to the cytokine profile observed in CBMCs transfected with Poly(I:C), neither LPS nor CpG activation of PBMCs or CBMCs resulted in detectable IL-12p70 (FIG. 8E, I), or secretion of IFNγ (FIG. 8F, J). Again, IL-23 and IL-10 levels were low with no significant difference between adult and neonatal mononuclear cells noted in response to LPS or CpG (FIG. 8G, K, L). Dotplots are shown in FIG. 13F-Q.

CONCLUSION

Noting the disparity in neonatal and paediatric morbidity between bacterial and viral infections in ICU admissions we speculated that infants were better equipped to fight viral infection than bacterial infection. Viruses and bacteria are both recognised by a variety of PRRs, however, as viruses produce dsRNA in the cytosol in order to replicate, CNA-sensors are highly adapted to generate a robust anti-viral response including the induction of type I IFNs and cellular immunity. We were interested to assess the ability of CNA to induce a type I IFN response in neonates and children. Here we report for the first time that stimulating CBMCs with a variety of dsRNA or dsDNA mimics results in strong induction of type I IFN comparable with responses in adults. A previous report by Renneson et al (2009) IL-12 and type I IFN response of neonatal myeloid DC to human CMV infection. *Eur J Immunol* 39, 2789-2799 showed that CMV-infected moDCs produce high levels of IFNα but lower levels of IL12 and IFNb. Interestingly, we found no evidence of IFNβ production in our system in response to CNA activation (data not shown) and, similar to CMV infection, the type I IFN produced in response to CNA activation was predominantly IFNα. We also confirm published reports that neonatal TLR4 and TLR9 are less able to induce a pro-inflammatory response when compared with adult PBMCs. Of note, human genetic studies have identified that host defence against two viruses that induce more serious disease in infants than adults; Herpes Simplex Virus (HSV) and Respiratory Syncytial Virus (RSV), do not depend on CNA signalling. Defence against HSV is dependent on TLR3 signalling, a further TLR shown to be impaired in children. While effective host defence targeting RSV has been shown to require type III IFN (IL-29) signalling and not type I IFN suggesting that induction of type III IFN might be impaired in children.

Several studies have reported conflicting data on the subpopulations of various cell types and total cell numbers in adult versus cord blood. Of particular interest, Drohan et al (2004) Selective developmental defects of cord blood antigen-presenting cell subsets. *Hum Immunol* 65, 1356-1369 have reported increased frequency of pDCs in cord blood, although several recent studies observed similar frequencies of pDCs between adult and cord blood. Due to the ability of pDCs to produce high amounts of Type I IFN (18), it was important to characterise the DC subsets in our cohort. Following isolation of mononuclear cells we found no differences in leukocyte percentages and no differences in DC subsets between adult and cord blood. We also found that classical and inflammatory monocyte subsets are the same between cord and adult mononuclear cells, an observation previously reported in the literature but in conflict with another report that suggested that decreased populations of monocytes could be responsible for observed hyporesponsiveness to LPS seen in neonates. Importantly, within our cohort, we found that monocytes isolated from either adult or neonate, stimulated with CNA or TLR ligands mirrored the IFN response observed in the PBMC/CBMC system. Unfortunately, we were unable to isolate sufficient numbers of DCs from our samples to check their responses by ELISA and at this time we cannot rule in or out the role of pDCs.

It appears that in our system, altered cell subsets are unlikely to play a role in the divergent regulation of IFN in response to CNA or TLR ligands. In fact, our data demonstrating parity in cell signalling downstream of TLR-4/-7/-8/-9 to TNFα induction in both neonates and adults highlighted the striking disparity in cell signalling to IFN induction downstream of TLR-4/-7/-8/-9 and the CNA sensors. The signalling pathways leading to the production of IFNα are largely shared between the various receptors beyond adaptor level. A key difference between TLR-induced type I IFN and CNA induction is TLR-dependence on endosomal localisation to engage with TRAF3 and the IRFs. Several Rab GTPases have been reported to be involved in trafficking TLRs. Of particular interest, in response to LPS stimulation or *E. coli* infection, type I IFN production relies on the regulation of TLR4 transport to sorting phagosomes by Rab11a. In the absence of Rab11a, IFN production is significantly attenuated, whereas TNFα induction is unchanged. Conversely, type I IFN responses downstream of cytosolic receptors have no dependency on endosome formation due to receptor location in the cytoplasm. We therefore investigated the expression and function of Rab11a in neonatal CBMCs compared to adult PBMCs. Of four Rab GTPases tested, basal expression of Rab11 was significantly lower in cord blood monocytes than in adult monocytes. Further upon LPS stimulation, the percentage of monocytes with detectable Rab11+ endosomes was strikingly higher in adult monocytes when compared with cord blood monocytes. Given our data showing that the transcription of IFNα was inhibited in CBMCs in response to LPS it seems plausible that a deficiency in Rab11-positive endosome formation may account for the attenuated IFNα production in response to LPS in neonates. A requirement for Rab11-positive endosome formation has not yet been attributed to TLR7/8/9 as such, the mechanism underlying the attenuation of IFNα/β induction in response to CL075 or CpG in neonates remains to be investigated.

Previously, Aksoy et al (2007) Interferon regulatory factor 3-dependent responses to lipopolysaccharide are selectively blunted in cord blood cells. *Blood* 109, 2887-2893 reported that LPS cannot induce IFNβ in neonatal moDCs due to a lack of binding of IRF3 to CBP. Efficient interaction of IRF3 with its co-activator CBP is essential for transcriptional activity of IFN genes. Our data demonstrating that type 1 IFN induction is equivalent between adult and neonatal mononuclear cells/monocytes downstream of CNA-stimulation, would strongly imply that there is no integral or inborn defect in the neonatal IRF3-CBP interaction in these cells when compared with adults. This discrepancy could potentially be due to cell type differences i.e. moDCs vs monocytes or it could be that downstream of LPS, post-translational modifications of IRF3 required for CBP binding are defective in neonates due to the attenuation of the Rab11+ endosome trafficking of IRF3; or it could be simply a limitation of the inherent variability observed between cells isolated from human blood.

To assess whether the response to CNA observed in cord blood was unique to cord blood or persisted through infancy and childhood we isolated PBMCs from children undergoing elective surgery. The enhanced production of type I IFN in response to cytosolic Poly(I:C) was maintained up to the age of two, at which point it appears to level off to match adult levels. Poly(dA:dT) induced production of type I IFN was maintained across all age groups. Interestingly, the induction of TNFα in response to CNA also remained steady up until the age of two at which point it drops to adult levels. Type I IFNs have critical roles in the induction of adaptive immunity; they promote the generation of cytotoxic T cell responses as well as a Th1-biased CD4$^+$ T cell phenotype. Type I IFNs drive cellular immunity by promoting the activation and functional maturation of DCs, facilitating antigen presentation to CD4$^+$ T cells, cross priming of CD8$^+$ T cells as well as inducing IFNγ and opsonizing antibodies. Initiating Th1 responses and cytotoxic T cells is vital in the fight against intracellular pathogens, infections neonates are most susceptible to, and are the holy grail for vaccine development. Currently, a major obstacle for improving the impaired vaccine responses observed in infants appears to be the lack of age-specific adjuvants that can safely drive potent cellular immunity against intracellular pathogens, resulting in the need for multiple booster injections and in some cases delaying the administration of a vaccine until a certain age has been reached. Aluminum salts (alum) find wide clinical application as adjuvants and promote humoral immunity and T helper type 2 (Th2) cell responses. However, a major disadvantage of alum is its limited ability to efficiently drive Th1 responses, motivating the search for targeted neonatal and paediatric vaccine adjuvants, an unmet need recently highlighted in an EU commissioned report on vaccines. We tested the potential of cytosolic Poly(I:C) to promote a Th1 response through measuring the production of Th1-polarising IL-12p70 and induction of IFNγ in adult and cord blood mononuclear cells. We found that neonates produced significantly higher levels of both IL-12p70 and IFNγ in response to CNA than adult PBMCs. Conversely, there was no difference in levels of anti-inflammatory IL-10 or Th17-polarising IL-23 between neonates and adults basally or in response to cytosolic Poly(I:C). By comparison neither LPS nor CpG activation of CBMCs induced either IL-12p70 or IFNγ. A recent study by Borriello et al (2017) Identification and Characterization of Stimulator of Interferon Genes As a Robust Adjuvant Target for Early Life Immunization. *Front Immunol* 8, 1772 has investigated the adjuvancy potential of combining Alum with activation of STING, in mice. This study, along with our work in human neonatal cells, highlights the potential of these intracellular receptors in future vaccine development. From a physiological perspective it is interesting to speculate that infants have evolved constrained responses to bacterial infections to allow for appropriate commensal colonisation of the skin and gut without major inflammatory response while at the same time broadly conserving effective defence against inherent viral pathogenicity, by enabling CNA sensors to mount an efficient immune response against invasive infection. Together our data indicates that CNA and activators of CNA-sensors possess major potential to guide the neonatal immune response in the direction of cell-mediated immunity and that this response is active and robust in neonates and persists throughout childhood.

EXAMPLES 2A AND B

2.0 Example 2A

2.1 Materials

All materials and reagents used were bovine specific unless stated.

2.1.1. Animals

All the blood sampling was performed on research farms under the licence from the Department of Health and Children or the Health Products Regulatory Authority. All animals used in this research project were healthy calves under 1 year old (unless stated).

2.1.2. General Tissue Culture Materials

Complete RPMI 1640 culture medium (cRPMI)

Roswell Park Memorial Institute (RPMI) 1640 medium (Biosera) was enriched with 8% heat-inactivated foetal calf serum (Biosera), 2 mM L-glutamine and 50 units/ml penicillin (Gibco) and 50 µg/ml streptomycin (Gibco). For some western blot analysis, RPMI was supplemented with L-glutamine, penicillin and streptomycin but without foetal calf serum.

T Cell Medium

To a volume of 550 ml cRPMI-1640, 500 µl of 2-mercaptoethanol (Gibco), 2 ml of MEM vitamins (choline chloride, D-calcium pantothenate, folic acid, nicotinamide, pyridoxal hydrochloride, riboflavin, thiamine hydrochloride and i-inositol) and 5 ml of sodium pyruvate (Gibco) and amino acids (Gibco) were added.

PBS—Sterile phosphate buffered saline (Biosera)

TABLE 2.1

| TLR Ligands | | |
| --- | --- | --- |
| TLR ligand | Target | Supplier |
| LPS from *Escherichia coli*, Serotype R515 | TLR4 | Enzo Life Sciences |

TABLE 2.2

| Adjuvants used in-vitro | |
| --- | --- |
| Adjuvants | Supplier |
| Alhydrogel (Alum) | Brenntag Biosector, Frederikssund, Denmark |

TABLE 2.3

| List of reagents used for in-vitro stimulation of cells | |
| --- | --- |
| Reagent | Supplier |
| Concanavalin A (referred to as ConA) | Sigma-Aldrich |
| Poly dA:dT (deoxyadenylic-deoxythymidylic) acid sodium salt (referred to as polydA:dT) | Sigma-Aldrich |

2.1.3. Enzyme-Linked Immunosorbent Assay (ELISA) Materials

Sodium Carbonate-Bicarbonate Buffer 1.06 g of sodium carbonate (Sigma-Aldrich) and 1.06 g of sodium bicarbonate (Sigma-Aldrich) was diluted in 100 ml of $dH_2O$ and adjusted to pH 9.4.

PBS 10×—800 g NaCl, 116 g $NaP_2PO_4$, 20 g KCL and 20 g $KH_2PO_4$ was brought up to a volume of 10 L of $dH_2O$ and adjusted to pH 7.4.

Wash buffer—For all ELISA kits excluding IFN-γ, the wash buffer consisted of 1×PBS plus 0.05% Tween 20. The wash buffer for the IFN-γ ELISA was 0.05% Tween 80 in 1×PBS.

Substrate solution—All ELISA's were developed using Tetramethyl benzidine (TMB) (Millipore).

Stop solution—1M $H_2SO_4$

TABLE 2.5

| ELISA kits | | |
| --- | --- | --- |
| Kit | Supplier | Cytokine |
| Bovine IL-1β ELISA Kit | ThermoScientific | IL-1β |
| Bovine IFN-γ Specific ELISA Assay Kit | AbD Serotec | IFN-γ |
| Bovine IL-17 VetSet ELISA Development Kit | Kingfisher Biotec | IL-17 |

2.1.4. Quantitative Real-Time PCR (qPCR)

RNA Isolation—RNeasy Mini Kit 50 (Qiagen) as per manufacturer's instructions.

TABLE 2.6

| Reverse Transcription reagents | |
| --- | --- |
| Reagent | Supplier |
| Reverse transcriptase buffer | Promega |
| Random Primers 5'-NNNNNN-3' | MWG Biotech |
| dNTPs | Promega |
| RNaseOUT | Invitrogen |
| M-MLV Transcriptase | Promega |

Real-Time PCR Reagents—Real-Time Master Mix contained—Fast SYBR Green Master Mix (Applied Biosciences) with Rox dye, nuclease free water and primer mix.

Primers—Primers (Sigma-Aldrich) were designed to target specific genes and avoid amplification of genomic DNA.

TABLE 2.7

| Primer sequences (5'-3') | | |
| --- | --- | --- |
| IFN-α | | |
| Forward | ACCTAGAGAGCAGGTTCACAGA | (SEQ ID No. 1) |
| Reverse | CAGCTGAGCAGCAACAGGAT | (SEQ ID No. 2) |
| IFN-β | | |
| Forward | TCCAGCACATCTTCGGCATT | (SEQ ID No. 3) |
| Reverse | AAGGAGGTCCTCGATGATGG | (SEQ ID No. 4) |
| IFI-16 | | |
| Forward | GGAAGTCGTGGTTTATGGACAGCG | (SEQ ID No. 5) |
| Reverse | CCTTGGTGACCTTG-ATGAAACTATGAAT | (SEQ ID No 6) |
| PPIA | | |
| Forward | CCACCGTGTTCTTCGACAT | (SEQ ID No. 7) |
| Reverse | TCTGTGAAGCAGGAACCT | (SEQ ID No. 8) |

2.2 Method

2.2.1. PBMC Isolation

Bovine peripheral blood mononuclear cells were isolated from whole blood samples collected in 9m1 vacutainers containing Heparin anticoagulant. PBMCs were spun and separated using leucosep tubes (Cruinn) and a density gradient histopaque 1077 (Sigma-Aldrich) at a speed of 1200 g for 20 minutes. Red blood cell contamination was eliminated using sterile 0.25% sodium chloride (Baxter) as a lysis buffer. The cells were subsequently washed twice in PBS at a speed of 600 g for 10 minutes to remove impurities.

Cells were counted using a haemocytometer, microscope and trypan blue (Sigma Aldrich) and seeded at appropriate densities in tissue culture plates (Cruinn) containing media. The cells were incubated at 37° C. at 5% $CO_2$ treated within hours of plating to avoid unwanted cell death.

2.2.2. Cell Stimulations

For experiments involving the analysis of IL-1β, bovine antigen presenting cells were primed with LPS (100 pg/ml). This concentration was selected after testing effects of a range of different LPS concentrations ranging from 1 pg/ml-1 μg/ml. Adjuvant stimulation occurred 3 hours after LPS treatment. Similar to LPS, adjuvant concentrations were selected after testing multiple different doses. After stimulation, the cells were cultured for an additional 24 hours. Supernatants were harvested and stored at −20° C. for further analysis.

When analysing the effects of IL-1β on T cell activation, cells were pre-treated with 250 μg/ml of IL-1 receptor antagonist (IL-1Ra) 40 minutes before stimulation with IL-1β (25 ng/ml). Cells were subsequently stimulated with concanavalin A (1 μg/ml) 1 hour after addition of IL-1β. Similarly, when analysing the effects of polydA:dT on T cell activation, cells were stimulated with polydA:dT (1 μg/ml) 1 hour before ConA treatment (1 μg/ml). LPS (100 pg/ml) primed cells were incubated with YVAD-FMK (10 μm), an inhibitor specific for caspase-1. After 40 minutes, the cells were stimulated with alum (50 μg/ml) for 24 hours and supernatants were then harvested and analysed by ELISA for IL-1β

2.2.3. Enzyme-Linked Immunosorbent Assay (ELISA)

Measurement of Cytokine Concentrations

All cytokine concentrations were analysed using commercially available ELISA kits from Thermo Scientific, 2B Scientific, R&D systems and AbD Serotec. All antibody and standard concentrations, buffers, diluents and incubation times are outlined in Tables 2.10-2.13.

Capture antibodies (50 µl/well), diluted in the appropriate buffers, were dispensed into the wells of high binding plates (Greiner Bio-One) and incubated overnight at room temperature or 4° C. For analysis of IL-17, the ELISA plates were pre-coated with capture antibody by the manufacturing before delivery. The wells were washed with PBS/Tween 3 times and the plates were then incubated with 150 µl of blocking buffer for 1 hour at room temperature. The plates were washed again before supernatant (neat or diluted) and recombinant standards were added for 1 hour at room temperature. Following this, the plates were washed and 50 µl of detection antibody was added to the wells for a period of 1 or 2 hours at room temperature. After washing, 50 µl diluted streptavidin-HRP was added to the plate for between 30 minutes and 1 hour. After the final wash, 50 µl of 3,3'-, 5,5'-Tetramethylbenzidine (TMB) substrate was added and the plates were incubated in the dark. The reaction was stopped by addition of 1M sulphuric acid and the absorbance readings were measured at 450 nm using a microtitre plate reader. The cytokine concentrations were calculated using a linear regression standard curve from recombinant cytokines of known concentration. Skanit™ software was used to estimate values.

Thermo Scientific

Coating buffer: 0.2M Sodium bicarbonate buffer in distilled water at pH 9.4

Blocking buffer: 5% sucrose and 4% BSA in PBS

Reagent diluent: 4% BSA in PBS at pH 7.4

Capture antibody: 1/100 dilution in coating buffer

Detection antibody: 1/100 dilution in reagent diluent for 1 hour

Streptavidin-HRP: 1/400 dilution in reagent diluent for 30 mins

TABLE 2.8

|  | Thermo Scientific | | |
|  | Table 2.8. Thermo Scientific | | |
| Cytokine Concentration | Capture Antibody Concentration | Detection Antibody Concentration | Standard |
| --- | --- | --- | --- |
| IL-1β | 50 µg/ml | 50 µg/ml | 31-2000 pg/ml |

AbD Serotec

Blocking buffer: 4% BSA in PBS

Reagent diluent: 0.2M NaCl in PBS/Tween (0.05%)

Capture antibody: 1/200 dilution in PBS/Tween (0.05%)

Detection antibody: 1/100 dilution in PBS/Tween (0.05%) for 1 hour

Streptavidin-HRP: 1/400 dilution in PBS/Tween (0.05%) for 1 hour

TABLE 2.9

|  | AbD Serotec | | |
| Cytokine Concentration | Capture Antibody Concentration | Detection Antibody Concentration | Standard |
| --- | --- | --- | --- |
| IFN-γ | Not specified by manufacturer | Not specified by manufacturer | 0.025-20 ng/ml |

2.2.4. RNA Extraction and cDNA Synthesis

RNA extraction was conducted using Trizol and an RNeasy Plus Mini Kit (Qiagen Ltd). Tissue culture plates of stimulated cells were spun and supernatants were extracted while the remaining adherent cells were lysed using Trizol. Chloroform (200 µl per 1 ml of Trizol) was then added to the cell lysates and mixed vigorously before being centrifuged at 12000 g for 15 minutes at 4° C. The resulting aqueous layer of RNA was transferred to another tube containing 1 volume of ethanol. The mixture was then added to an RNeasy column and processed according to the manufacturer's instructions (Qiagen Ltd). After rigorous purification, the RNA was isolated and quantified using NanoDrop ND-1000 UV-Vis Spectrophotometer (NanoDrop Technologies Inc.). Finally the samples were stored at −80° C.

RNA was converted to cDNA using a High-Capacity cDNA Reverse transcription Kit (Applied Biosystems). Components needed for reverse transcriptase included RNA, RT 5× buffer, RNase Out, random hexamers, dNTP's and reverse transcriptase. The process was conducted under the following conditions: 25° C. for 10 minutes, 42° C. for 60 minutes, 95° C. for 3 minutes and hold at 4° C. The resulting cDNA was stored at −20° C.

Bovine genome sequences and primers were obtained and designed using Blast. To eliminate any possibility of amplifying contaminating genome DNA, primer specificity was confirmed using Primer Blast. Primers were synthesised by Sigma-Aldrich Ireland Ltd, Wicklow, Ireland. All primers were intron spanning to avoid amplifying any contaminated genomic DNA.

TABLE 2.11

|  | PCR cycle | |
| Temperature | Time |
| --- | --- |
| 25° C. | 10 minutes |
| 37° C. | 120 minutes |
| 85° C. | 5 minutes |
| 4° C. | ∞ |

2.2.5. Quantitative Real-Time PCR (qRT-PCR)

Using, SYBR Green intercalating dye (Applied Biosystems Ltd), qRT-PCR was performed using Applied Biosystems 7500 Fast Real-Time PCR System. Each well on the qRT-PCR plate was comprised of SYBR Green dye, nuclease free $H_2O$, cDNA, forward and reverse primers. Two negative controls were included to ensure no contamination was present. The cycle parameters of the process were: 95° C. for 20 seconds, 40 cycles at 95° C. for 3 seconds, 60° C. for 30 seconds followed by the dissociation steps which were: 95° C. for 15 seconds, 60° C. for 60 seconds, 95° C. for 15 seconds and 60° C. for 15 seconds. The Ct (threshold cycle) values from both the target and reference gene were used to measure the concentration of the target gene in the PCR reaction.

TABLE 2.12

| qRT-PCR cycle | | |
|---|---|---|
| Temperature | Time | Cycles |
| 95° C. | 20 seconds | 1 |
| 95° C. | 3 seconds | 40 |
| 60° C. | 30 seconds | 40 |

2.2.6. Statistical Analysis

Statistical analysis was performed using Graphpad Prism 5 software. The means for three or more groups were compared using one-way ANOVA. To identify differences between individual groups, the Tukey Multiple Comparisons test was used. The compare the means for two groups, the paired Student T-test was used. A P-value of <0.05 was taken as statistically significant.

2.3 Results & Conclusion

Th1 responses are an essential component of the immune response to many infections, particularly intracellular bacteria and viruses. Neonatal cattle are highly susceptible to a number of bacterial infections and the deficiency in producing interferon gamma is thought to underly this.

We have compared responses of peripheral blood mononuclear cells (PBMCs) taken from cattle over the first 10 months of life, to stimulation with the mitogen ConA and found that interferon gamma production is very low until 6 months of age (FIG. 14). Stimulation of cells with the toll like receptor ligand LPS does not significantly enhance interferon gamma responses. We looked at the potential of inflammasome activators to enhance IFN-γ production and found that inclusion of alum can enhance IFN-γ production to some degree (FIG. 15). Furthermore, the addition of the cytokine interleukin 1 with ConA enhanced IFN production. While alum is an activator of the NLRP3 inflammasome, poly(dA:dT) activates the AIM2 inflammasome in humans cells. Here we found that co-stimulation of bovine PBMCs with ConA and poly (dA:dT) strongly enhanced IFN-γ production by PBMCs from adult (8 months old) animals (FIG. 17). Crucially, when added with ConA to PBMCs from 2 month old animals, poly(dA:dT) strongly enhanced IFN-γ production (FIG. 18). Furthermore, transfected poly (dA:dT) enhanced type 1 interferon secretion from PBMCs, namely IFNα and IFNβ (FIG. 19). In human macrophages poly(dA:dT) induced IL-1 secretion is AIM2 dependent while its induction of type 1 IFN depends on IFI16. Indeed, we have shown that polydA:dT regulates IFI-16 expression which could possibly play a role in regulating type I IFNs (FIG. 20).

Since cattle in contrast to humans (5 members) only have a single PYHIN gene, IFI16, it is likely that polydA:dT induction of interleukin 1 and type 1 IFN is IFI16 dependent. These findings implicate IFI16 as a key target for the promotion of Th1 responses in neonatal cattle. Specifically, our discovery that polydA:dT overcomes the deficiency in interferon gamma production in neonatal cattle points to the potential of this adjuvant or derived variants in vaccines targeted to neonatal cattle for diseases including Johne's disease.

In summary, our results show that adjuvants which promote the induction of type 1 interferons can overcome the deficiency in interferon gamma production by peripheral blood mononuclear cells from animals over the first few months of life. Specifically, we found that transfection of the adjuvant Poly (deoxyadenylic-thymidylic) acid promotes type 1 interferon dependent enhancement of interferon gamma production in PBMCs. We conclude that this strategy will provide a valuable means to enhance Th1 immune responses in neonatal cattle or other animals and facilitate the generation of improved vaccines.

3.0 EXAMPLE 2B 3.1 Materials and Methodology

The potential of polydA:dT or other activators of nucleic sending pathways was addressed in bovine cells to determine if these may be potential targets for vaccine adjuvant development in calves. To determine if activating these pathways could overcome deficient IFN-γ production in young calves, the responsiveness of bovine PBMCs to polydA:dT was determined over the first 6 months of life.

The materials and methodology are as described in Example 2A.

While the PYHIN family consists of 13 and 4 different proteins in mice and humans respectively, only one functional PYHIN member has been identified in cattle.

3.2. Results 3.2.1 Calves Exhibit a Limited Capacity to Produce IFN-γ Up to 6 Months In response to ConA stimulation, IFN-γ production was low until the calves reached 6 months of age (FIG. 14). The capacity to produce IFN-γ increased with time up to 10 months of age.

3.2.2. IFN-γ Secretion is not Enhanced in Response to Alum

In response to alum, ConA stimulated bovine PBMCS display no marked increase in IFN-γ secretion (FIG. 15).

3.2.3 PolydA:dT Enhances IFN-γ Secretion by PBMCs

IFN-γ is a potent immuno-modulatory cytokine involved in conferring protection against a number of diseases in cattle including *Mycobacterium bovis* and *Mycobacterium avium* subspecies *paratuberculosis*. It has been demonstrated that polydA:dT treated dendritic cells can drive IFN-γ secretion from human CD4$^+$ T cells, although its potential to regulate bovine IFN-γ has not been addressed.

Therefore, to investigate if polydA:dT could drive enhanced IFN-γ secretion from bovine cells, PBMCs from 9 Friesian calves aged <1 year old were cultured with ConA (1 μg/ml) and polydA:dT (1 μg/ml) in the presence or absence of LPS (100 pg/ml). There was an increase in IFN-γ secretion when cells were stimulated with polydA:dT in the presence and absence of LPS (FIG. 16 & FIG. 17)

3.2.4 PolydA:dT Enhances Type I IFN and ISG-15 Expression

IFN-α and IFN-β are cytokines belonging to the type I IFN family. Since their initial discovery in 1957 by Isaacs and Lindenmann, type I IFNs have been implicated in the protection against zoonotic diseases including foot-and-mouth disease virus (FMDV). Although it has yet to be investigated in cattle, polydA:dT has been shown to enhance both murine and human type I IFNs. Furthermore, it has been shown in cattle that type I IFNs can regulate ISG-15, an ubiquitin protein involved in driving T cell responses. As a result, the ability of polydA:dT to drive type I IFNs and ISG-15 expression was investigated.

In response to polydA:dT, IFN-α and IFN-β gene expression was enhanced after 6 hours in comparison to unstimulated cells (FIG. 18). In addition, ISG-15 expression was also analysed as type I IFNs are a known driver of ISG15 in cattle. Interestingly, ISG-15 expression was also increased in response polydA:dT after 12 hours (FIG. 19).

3.2.5 PolydA:dT Drives Enhanced IFN-γ Secretion by PBMCs from Neonatal Calves

In Ireland, intracellular infections are one of the leading causes of death in cattle. IFN-γ, a cytokine that signals APCs to kill intracellular pathogens, is a key component of host defence. However, it has been documented in humans that cells from neonates have a reduced capacity to secrete IFN-γ, rendering them susceptible to infection. Similarly, Price et al demonstrated that WC1⁺ γδ T cells from calves, which can constitute up to 50% of total lymphocytes in neonatal cattle, secrete significantly low levels of IFN-γ in response to *M. bovis* in comparison to those co-cultured with DCs infected with *M. bovis*. This result demonstrates the role activated DCs can play in driving enhanced IFN-γ production in calves, who normally display a reduced capacity to secrete this cytokine.

In FIG. 14 it was shown that ConA induced IFN-γ secretion is a delayed response. However, it was demonstrated in mice that IL-1β can enhance IFN-γ secretion. Here, the ability of inflammasome activating adjuvants to increase IFN-γ secretion was investigated. PBMCs from 5 Friesian calves were isolated each month beginning when the animals were 1 month old until they reached 5 months of age. The 4 month time point was excluded due to unforeseen complications involving the isolation of PBMCs. Upon isolating the PBMCs, the cells were incubated with ConA in the presence or absence of LPS. Additionally, the ConA and/or LPS treated cells were also stimulated with or without polydA:dT.

As demonstrated previously, ConA induced IFN-γ secretion by PBMCs is limited until 3 months of age (FIG. 20B), similar to what was observed in FIG. 14. The response was similar when PMBCs were cultured in the presence of LPS and ConA (FIG. 20A). Interestingly, in the presence and absence of LPS, ConA induced IFN-γ secretion was significantly enhanced in response to polydA:dT (FIG. 20A, B). The results were most evident in the first 2 months of life after which the enhancement was not statistically significant. However, in the presence of LPS the IFN-γ driving effects of polydA:dT were more apparent although not statistically significant (FIG. 20A).

3.2.6. PolydA:dT can Promote the Secretion of IL-1β from Bovine PBMCs in the Absence of LPS Priming To generate and secrete bioactive (processed) IL-1β and IL-18, antigen-presenting cells (APCs) require two signals, most commonly in the form of a TLR agonist and an inflammasome activator. TLR agonists prime cells to generate inactive pro-IL-1β, while inflammasome activators mediate caspase-1 activation and the cleavage and secretion of processed IL-1β. It has been demonstrated in murine and human studies that polydA:dT can regulate IL-1β secretion in LPS primed macrophages and PBMCs respectively. However, there are no published reports addressing the immunological effects of polydA:dT on bovine PBMCs.

Therefore, to determine if polydA:dT could mediate innate immune responses similar to those observed in human and murine cells, PBMCs from 5 Friesian calves were isolated and stimulated with polydA:dT and LPS. When primed with LPS, PBMCs secreted IL-1β when stimulated with polydA:dT at various concentrations (FIG. 21A). Remarkably, PolydA:dT was capable of driving IL-1β secretion in the absence of priming with LPS (FIG. 21A). There was no significant difference in IL-1β concentrations between those cells stimulated in the presence or absence of LPS. To ascertain if the PBMCs contained pre-formed IL-1β cells were also stimulated with alum (which can promote NLRP3 inflammasome activation but cannot drive the generation of pro-IL-1β). Interestingly, only two of the five animals tested secreted IL-1β in response to alum indicating that some animals did not contain pre-formed IL-1β (FIG. 21B). When the process was repeated using human PBMCs, only cells primed with LPS 3 h prior to transfection with polydA:dT secreted processed IL-1β (21C). Similar to polydA:dT, alum was a weak stimulus for promoting IL-1β secretion in the absence of LPS priming (FIG. 21D). PolydA:dT was used at 1 μg/ml in all future experiments unless otherwise stated.

To investigate whether polydA:dT can regulate the synthesis of pro-IL-1β, PBMCs were cultured with polydA:dT and pro-IL-1β was probed by western blotting. Expectedly, LPS alone or in the presence of polydA:dT is capable of driving pro-IL-1β after 16 hours (FIG. 21E). However, although not present in unstimulated cells, pro-IL-1β was evidently expressed in cells stimulated with polydA:dT in the absence of LPS (FIG. 21E). Similarly, treatment of PBMCs with polydA:dT enhances pro-IL-1β expression after 6 hours (data not shown).

In addition to IL-1β, polydA:dT has been shown to enhance IL-18 secretion from murine macrophages. Thus, it was important to establish if IL-18 was expressed in bovine PBMCs in response to polydA:dT. Indeed, IL-18 expression was increased in response to polydA:dT after 6 hours (FIG. 21F).

3.2.7 PolydA:dT Induces IL-1β Secretion Independently of LPS in PBMCs from 1 Month Old Calves Having demonstrated that polydA:dT can regulate IL-1β secretion independently of LPS in PBMCs from calves aged <1 year, it was important to investigate if this was only evident in older animals or also seen in PBMCs from neonates. To test this, PBMCs from 5 Friesian neonatal calves (aged 1 month) were isolated and stimulated with varying doses of polydA:dT in the presence or absence of LPS. PBMCs from all 5 neonates secreted IL-1β in response to polydA:dT following LPS priming (FIG. 22A). Interestingly, in the absence of LPS priming, PBMCs from 1 month old calves secreted processed IL-1β following polydA:dT stimulation (FIG. 22A). One month later this experiment was repeated using the same 5 calves to assess responses at 2 months of age. Indeed, processed IL-1β was present in supernatants from cells stimulated with polydA:dT in absence or presence of LPS (FIG. 22B).

3.2.8. PolydA:dT Enhances Type I IFN and ISG-15 Expression

IFN-α and IFN-β are cytokines belonging to the type I IFN family. Since their initial discovery in 1957 by Isaacs and Lindenmann, type I IFNs have been implicated in the protection against zoonotic diseases including foot-and-mouth disease virus (FMDV). Although it has yet to be investigated in cattle, polydA:dT has been shown to enhance both murine and human type I IFNs. Furthermore, it has been shown in cattle that type I IFNs can regulate ISG-15, an ubiquitin protein involved in driving T cell responses. As a result, the ability of polydA:dT to drive type I IFNs and ISG-15 expression was investigated.

In response to polydA:dT, IFN-α and IFN-β gene expression was enhanced after 6 hours in comparison to unstimulated cells (FIG. 23A & FIG. 23B). In addition, ISG-15 expression was also analysed as type I IFNs are a known driver of ISG15 in cattle. Interestingly, ISG-15 expression was also increased in response polydA:dT after 12 hours (FIG. 23C).

3.2.9 The Ability of PolydA:dT to Enhance IL-1β and IFN-γ Secretion in Bovine PBMCs is Caspase-1 Dependent Having demonstrated that polydA:dT enhances IFN-γ secretion possibly through the regulation of type I IFNs and IL-1β, we next sought to investigate if polydA:dT-induced IFN-γ production was caspase-1 dependent. In mice, it has been established that polydA:dT promotes caspase-1 activation, which ultimately leads to the secretion of processed IL-1β. It has also been suggested that bovine herpes virus, a DNA virus affecting cattle, mediates pathogenesis through caspase-1.

To inhibit caspase-1 signaling, PBMCs from four Friesian calves <6 months old were cultured with YVAD-cmk (10 μm) 1 hour prior to polydA:dT stimulation. As polydA:dT can stimulate bovine IL-1β secretion (FIG. 21A) in the absence of TLR4 signaling, cells were not primed with LPS. Interestingly, polydA:dT induced IL-1β secretion was attenuated when caspase-1 was inhibited (FIG. 24A).

Having demonstrated that polydA:dT mediates IL-1β secretion through caspase-1, we next sought to investigate if polydA:dT induced IFN-γ secretion was also dependent on caspase-1. To test this, PBMCs from four Friesian calves aged <6 months were pre-incubated with YVAD-cmk prior to stimulation with polydA:dT and ConA. Indeed, it was shown that IFN-γ secretion in all four calves was reduced when caspase-1 was inhibited (FIG. 24B).

3.3. Discussion

For neonates, birth represents a shift from a sterile environment in utero to one where susceptibility to infection is high. However, calves have a relatively underdeveloped adaptive immune system and rely heavily on maternally derived antibodies and innate responses for immunological protection. While providing short-term protection, these responses are incapable of conferring life long immunity against complex pathogens and viruses. Therefore, incorporating adjuvants into vaccines to induce long-term adaptive immune responses could prove effective in protecting animals through this period of susceptibility.

Having demonstrated that caspase-1 activation in ConA stimulated PBMCs can enhance IFN-γ secretion in young calves, it was important to discern potential adjuvants capable of driving T cell associated cytokines. Studies have already identified adjuvant candidates capable of inducing Th1 cell responses in cattle including CAF01 (coupled with MAP antigens) and lipoarabinomannan incorporated in Freunds incomplete adjuvant. While inflammasome activating adjuvants have been investigated widely in a human and murine context, these have received less attention in cattle. Murine and human studies have shown that inflammasome stimulating nanoparticles can promote Th1 cell responses. In this study, transfected polydA:dT, a synthetic dsDNA analog, was investigated as a possible adjuvant to drive enhanced caspase-1 derived cytokines and type I IFN dependent IFN-γ. It has been established in mice and humans that polydA:dT primarily signals through the AIM2 and IFI-16 inflammasomes to mediate IL-1β secretion. AIM2 and IFI-16 belong a family of innate sensory molecules called PYHINs. Interestingly, while mice and humans have 13 and 4 different PYHINs respectively, there has been only one PYHIN member identified in cattle. However, while AIM2 is present as a pseudogene in cattle, functional IFI-16 has been identified in bovine kidney cells. Furthermore, IFI-16 and caspase-1 expression were shown to be upregulated in response to BoHV1, suggesting that this PYHIN could be involved in sensing dsDNA stimuli.

The purpose of this study was to investigate the potential of the bovine PYHIN ligand polydA:dT as an immuno-stimulator. In accordance with murine and human studies, polydA:dT enhanced IL-1β secretion from bovine cells.

Surprisingly, this response was also seen in the absence of LPS priming which contrasts with results observed in mice and humans. Indeed, through western blot analysis it was determined that polydA:dT can drive both the processing and secretion of IL-1β. In chapter 4, it was established that alum induced IL-1β secretion in the absence of LPS was evident in a subset of animals, whereas another subset of calves needed a combination of both LPS and alum to secrete processed IL-1β. In contrast, all calves secreted processed IL-1β in response to polydA:dT stimulation in the absence of LPS, even in cases where alum had no such effect thus removing the possibility that pre-formed pro-IL-1β was already present in these cells. Interestingly, it was also demonstrated that in the absence of LPS priming, human PBMCS did not secrete processed IL-1β. It was also established by RT-PCR that polydA:dT can drive enhanced IL-18 expression, a cytokine processed by caspase-1 and involved in promoting bovine IFN-γ secretion from T cells.

Having demonstrated that polydA:dT can drive IL-1β secretion and IL-18 expression, it was important to investigate if this adjuvant can enhance secretion of T cell associated cytokines by bovine PBMCs. Kis-Toth et al (Cytosolic DNA-activated human dendritic cells are potent activators of the adaptive immune response. J Immunol, 2011. 187(3): p. 1222-34.) demonstrated in humans that unprimed DCs transfected with polydA:dT could drive enhanced IFN-γ from naïve CD4+ T cells compared to DCs cultured with LPS alone or with a pro-inflammatory cocktail (TNF, IL-1β, Il-6, GM-CSF, PGE2). PBMCs from calves aged <1 year old displayed an increased capacity to secrete IFN-γ in response to polydA:dT, although the difference was only significant when cells were primed with LPS. It has been established in human and bovine studies, that IL-1β and IL-18 (respectively) drive enhanced IFN-γ when combined with IL-12, while these cytokines alone only induced minimal increases in IFN-γ in vitro. Thus, as LPS induces IL-12 secretion from bovine DCs, polydA:dT induced IL-1β and IL-18 may synergise with LPS driven IL-12 to promote IFN-γ production. The role of polydA:dT in enhancing IL-12 production remains unclear, but Katashiba et al (Interferon-alpha and interleukin-12 are induced, respectively, by double-stranded DNA and single-stranded RNA in human myeloid dendritic cells. Immunology, 2011. 132(2): p. 165-73.) demonstrated that polydA:dT is unable to drive IL-12p40 production from human myeloid DCs, thus supporting a possible role for LPS induced IL-12. However, whether or not polydA:dT can regulate IL-12 in a bovine context has not been addressed and thus requires further research.

PolydA:dT driven type I IFNs have been shown to enhance proliferation of IFN-γ secreting CD4+ T cells in mice. The current study demonstrates that polydA:dT increases IFN-α and IFN-β expression in bovine PBMCs, although the absence of a commercially available type I IFN ELISA kit prevented us from measuring the cytokines secreted into the supernatants. Coupled with the up-regulation of IL-1β secretion and IL-18 expression, enhanced expression of type I IFNs could explain the increase in IFN-γ secretion observed in bovine PMBCs in response to polydA:dT. ISG-15 is a cytoplasmic protein whose activation is dependent on type I IFN signalling. In response to polydA:dT stimulation, ISG-15 expression is increased in bovine PBMCs. In humans it has been established that ISG-15 plays a pivotal role in regulating IFN-γ secretion during myco-bacterial infection. Interestingly, Bogunovic et al (Myco-bacterial disease and impaired IFN-gamma immunity in humans with inherited ISG15 deficiency. Science, 2012. 337(6102): p. 1684-8.) also found that in addition to func-tioning as an intracellular signaling molecule, ISG-15 can act as an extracellular cytokine to drive enhanced IFN-γ. Therefore, polydA:dT induced IFN-γ secretion in bovine PBMCs could be dependent on the secretion of type I IFNs which in turn regulate ISG-15 expression.

Having demonstrated that polydA:dT drives type I IFNs, it was important to investigate if these cytokines are playing a significant role in regulating IFN-γ. It was shown by Valarcher et al, Role of alpha/beta interferons in the attenu-ation and immunogenicity of recombinant bovine respira-tory syncytial viruses lacking NS proteins. J Virol, 2003. 77(15): p. 8426-39.) that in response to BRSV, enhanced IFN-γ production correlated with an increase in IFN-α and IFN-β secretion.

It has already been demonstrated in this project that in contrast to alum, polydA:dT enhances IL-1β secretion in a NLRP3 independent manner. However, a number of other caspase-1 activating inflammasomes have been described including the AIM2 and IFI-16 inflammasomes. It has been demonstrated in cattle that caspase-1 is activated in bovine kidney cells in response in vitro stimulation with DNA virus BoHV-1. Indeed, polydA:dT induced IL-1β secretion is abrogated when caspase-1 is inhibited. This result suggests that bovine DNA sensors recognize the polydA:dT resulting in the assembly of an inflammasome complex (not NLRP3) and caspase-1 activation leading to enhanced IL-1β process-ing and secretion. It was important to investigate if inhib-iting caspase-1 would have deleterious effects on polydA:dT induced IFN-γ secretion. In addition to its enhancing effect on IL-1β processing and secretion, polydA:dT increased the expression of IL-18, a documented driver of IFN-γ in cattle. Moreover, as IL-18 secretion is also caspase-1 dependent, this could explain why inhibiting caspase-1 results in a marked decrease in IFN-γ production. Further studies will be required to formally prove that polydA:dT enhances the processing and the secretion of IL-18 in cattle.

IFI-16 represents the only functional PYHIN member that has been identified in cattle. Similar to humans and mice, the data presented here demonstrate that IFI-16 expression is enhanced by polydA:dT. Having shown that polydA:dT induced IL-1β secretion is caspase-1 dependent, polydA:dT may be sensed by IFI-16 which then recruits and activates caspase-1 leading to the cleavage and secretion of processed IL-1β and potentially IL-18. Furthermore, it has been estab-lished in humans and mice that in response to dsDNA, IFI-16 activates stimulator of interferon genes (STING) and TBK-1 to drive type I IFN secretion. Therefore, it is possible that in addition to driving IL-1β secretion through caspase-1, IFI-16 also plays a pivotal role in regulating type I IFN secretion through an alternative pathway involving STING and TBK-1. To prove that the immunological responses mediated by polydA:dT are IFI-16 dependent, future experi-ments designed at silencing IFI-16 through transfecting siRNAs are required. SiRNA transfection by electroporation was attempted during the course of this research project. However, correlating with a study conducted by Jensen et al, (Comparison of small interfering RNA (siRNA) delivery into bovine monocyte-derived macrophages by transfection and electroporation. Vet Immunol Immunopathol, 2014. 158(3-4): p. 224-32.) this method of transfection proved unsuccessful.

Neonatal calves are particularly susceptible to infection due to an underdeveloped immune system. Johne's Disease and bovine TB represent two common causes of mortality in calves. It has been established that IFN-γ plays an important role in mediating immunological protection against these diseases. ConA and polydA:dT drove enhanced IFN-γ secre-tion in neonatal PBMCs compared to ConA alone, although the response was less marked in cells when the calves were 3 and 5 months old. In contrast, the combination of ConA, LPS and polydA:dT was capable of driving enhanced IFN-γ secretion at all months although the response was only significant at 1 and 2 months of age. The addition of LPS may induce the secretion of IL-12, a cytokine known for driving enhanced IFN-γ in cattle. It is worth noting that in response to ConA and LPS, IFN-γ secretion was lower than ConA alone, alternatively suggesting that LPS may be attenuating ConA induced IFN-γ secretion possibly through driving IL-10 production. Nonetheless, polydA:dT induced a significant increase in IFN-γ secretion at 1 and 2 months in the presence or absence of LPS. Thus, polydA:dT or other adjuvants directed towards DNA sensing pathways may have the potential to enhance the effectiveness of vaccines administered to animals early in life.

This project has demonstrated that polydA:dT is a robust driver of IL-1β secretion and IL-18 expression in cattle. Moreover, as IL-18 has been shown to promote IFN-γ secretion from γδ T cells (the most predominant lymphocyte population in neonatal calves), it is possible that this cyto-kine is working in synergy with IL-1β to maximise IFN-γ secretion.

These data are the first to demonstrate that polydA:dT promotes IL-1β secretion, in addition to IL-18 and type I IFN expression in cattle. Furthermore, it is also the first study to show that polydA:dT enhances bovine IFN-γ secre-tion through caspase-1 dependent cytokines and type I IFNs. These data show that polydA:dT demonstrates the ability to drive enhanced IFN-γ from PBMCs of calves aged 1-2 months. Finally, this study identified DNA sensing mol-ecules as potential vaccine targets for IFN-γ mediated pro-tection.

The invention will now be described by the following non-limiting statements:

1. An adjuvant which promotes the induction of cytokines selected from interleukin-1 (IL-1), type 1 interferons (IFNs), such as IFNα, IFNβ, and type 2 interferons, such as IFNγ, and/or tumour necrosis factor (TNF) response, such as TNFα, for use in eliciting or enhanc-ing an immune response in a neonatal, juvenile or paediatric animal subject.

2. An adjuvant according to statement 1 for use in eliciting or enhancing a desired antigen-specific immune response.

3. An adjuvant according to statement 1 or statement 2 for use in eliciting or enhancing T helper 1 (Th1) immune response, gamma-interferon-inducible (IFI-16) gene expression, Ifi-16 protein expression, AIM2 gene expression, AIM2 protein expression, AIM-like recep-tor (ALR) gene expression or AIM-like receptor (ALR) protein expression, or enhancing an IL-1 response.

4. An adjuvant according to any of statements 1 to 3 for use in eliciting or enhancing gamma-interferon-induc-ible (IFI-16) gene expression or Ifi-16 protein expres-sion.

5. An adjuvant according to any of the preceding state-ments for use in eliciting or enhancing an immune response wherein the adjuvant is a cytosolic nucleic acid sensor agonist or synthetic analog or mimic thereof.

6. An adjuvant according to statement 5 for use in eliciting or enhancing an immune response wherein the adjuvant is selected from:

double stranded DNA (dsDNA);

double stranded RNA (dsRNA);

cyclic guanosine monophosphate-adenosine monophosphate (cGAMP); or a synthetic analog or mimic thereof.

7. An adjuvant according to any of the preceding statements for use in eliciting or enhancing an immune response wherein the adjuvant is a nucleic acid sensing receptor agonist selected from:

dsRNA mimic polyinosinic-polycytidylic acid (Poly(I: C));

dsDNA mimic poly(deoxyadenylic-thymidylic) acid (Poly(dA:dT));

5' triphosphate double stranded RNA (ppp-dsRNA); or

3'-haripin RNA (hpRNA).

8. An adjuvant according to any of the preceding statements for use in eliciting or enhancing an immune response wherein the adjuvant is Poly(deoxyadenylic-thymidylic) acid (Poly(dA:dT)).

9. An adjuvant according to any of the preceding statements for use in eliciting or enhancing an immune response wherein the adjuvant, preferably Poly(I:C) or Poly(dA:dT), is packaged in a delivery system, preferably a nanoparticle, cationic or polymeric delivery system, for delivery into cytoplasm of a cell.

10. An adjuvant according to any of the preceding statements for use in the prophylaxis and/or treatment of infections, such as bacterial, viral and/or parasitic infections.

11. An adjuvant according to any of the preceding statements for use in eliciting or enhancing an immune response in a non-human animal subject preferably an ungulate selected from the group consisting of porcine, ovine, bovine, and caprine; more preferably cattle under 28 days old, even more preferably neonatal cattle.

12. An adjuvant according to statement 10 for use in the prophylaxis and/or treatment of bovine tuberculosis and paratuberculosis (Johnes disease) in cattle and sheep.

13. An adjuvant according to any of statement 1 to 9 for use in eliciting or enhancing an immune response in a neonatal, juvenile and/or paediatric human subject up to 11 years, preferably up to 2 years, more preferably up to 24 months; optionally from 6 to 11 years, from 2 to 5 years, or from 4 months to 24 months.

14. An immunogenic pharmaceutical composition comprising an adjuvant which promotes the induction of interleukin-1 (IL-1), type 1 interferons (IFNs), such as IFN$\alpha$ and IFN$\beta$, type 2 interferons, such as IFN$\gamma$, and/or TNF response, such as TNF$\alpha$; and a pharmaceutically acceptable carrier or excipient.

15. A vaccine composition comprising an antigen and an adjuvant which promotes the induction of type 1 interferons (IFNs), such as IFN$\alpha$, IFN$\gamma$ and IFN$\beta$, and/or TNF response, such as TNF$\alpha$.

The words comprises/comprising when used in this specification are to specify the presence of stated features, integers, steps or components but does not preclude the presence or addition of one or more other features, integers, steps, components or groups thereof.

---

The invention claimed is:

1. A method of eliciting or enhancing an immune response, in a neonatal human or neonatal ungulate subject, the method comprising administering to the neonatal human or neonatal ungulate subject an adjuvant comprising an effective amount of a cytosolic nucleic acid sensor agonist which promotes the induction of IFNα, IFNβ, and/or -IFNγ, and wherein the adjuvant is selected from:

a double stranded DNA (dsDNA);

a double stranded RNA (dsRNA); or cyclic guanosine monophosphate-adenosine monophosphate (cGAMP)

and wherein the adjuvant is packaged in a delivery system for delivery into cytoplasm of a cell.

2. The method of claim 1 wherein the immune response is an antigen-specific immune response.

3. The method of claim 1 wherein the adjuvant is a nucleic acid sensing receptor agonist selected from:

dsRNA mimic polyinosinic-polycytidylic acid (Poly(I:C));

dsDNA mimic poly(deoxyadenylic-thymidylic) acid (Poly(dA:dT));

a 5' triphosphate double stranded RNA (ppp-dsRNA); or a 3'-hairpin RNA (hpRNA).

4. The method of claim 3 wherein the adjuvant is Poly (I:C) or Poly(dA:dT) and the delivery system is a nanoparticle, cationic or polymeric delivery system.

5. The method of claim 3 wherein the neonatal human or neonatal ungulate subject is in need of prophylaxis and/or treatment of bacterial, viral and/or parasitic infections.

6. The method of claim 3 wherein the subject is a neonatal human subject.

7. The method of claim 3, wherein the adjuvant is administered by injection into muscle or skin.

8. The method of claim 1, wherein the delivery system is a polymeric delivery system selected from polymer based nucleic acid nanocarriers or cationic polymers.

9. The method of claim 1, wherein the cytosolic nucleic acid sensor agonist is a TLR3 agonist.

10. The method of claim 3, wherein the adjuvant is administered by a mucosal route.

11. The method of claim 10, wherein the adjuvant is administered to nasal mucosa.

12. The method of claim 10, wherein the adjuvant is administered to oral mucosa.

13. The method of claim 12, wherein the adjuvant is administered sublingually.

* * * * *